(12) United States Patent
Chau et al.

(10) Patent No.: US 12,011,353 B2
(45) Date of Patent: *Jun. 18, 2024

(54) HEART VALVE SEALING DEVICES AND DELIVERY DEVICES THEREFOR

(71) Applicant: Edwards Lifesciences Corporation, Irvine, CA (US)

(72) Inventors: Mark Chau, Aliso Viejo, CA (US); David M. Taylor, Lake Forest, CA (US); Alexander J. Siegel, Irvine, CA (US); Christopher J. Olson, Lake Forest, CA (US); Sergio Delgado, Irvine, CA (US); Alexander H. Cooper, Costa Mesa, CA (US); Lauren R. Freschauf, Mission Viejo, CA (US); Asher L. Metchik, Hawthorne, CA (US); Matthew T. Winston, Aliso Viejo, CA (US); Cristobal R. Hernandez, Santa Ana, CA (US); Emil Karapetian, Huntington Beach, CA (US); Bao Khuu, Irvine, CA (US); Eric Robert Dixon, Villa Park, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 431 days.

This patent is subject to a terminal disclaimer.

(21) Appl. No.: 16/522,605

(22) Filed: Jul. 25, 2019

(65) Prior Publication Data
US 2019/0343624 A1    Nov. 14, 2019

Related U.S. Application Data

(63) Continuation of application No. 15/154,578, filed on May 13, 2016, now Pat. No. 10,517,726.
(Continued)

(51) Int. Cl.
*A61F 2/24*    (2006.01)

(52) U.S. Cl.
CPC ............ *A61F 2/246* (2013.01); *A61F 2/2454* (2013.01); *A61F 2/2463* (2013.01);
(Continued)

(58) Field of Classification Search
CPC ...... A61F 2/246; A61F 2/2463; A61F 2/2466; A61F 2/2454; A61F 2220/0016; A61F 2310/00023
See application file for complete search history.

(56) References Cited

U.S. PATENT DOCUMENTS

| 3,570,014 | A | * | 3/1971 | Hancock | ............... A61F 2/2418 623/2.18 |
| 3,874,388 | A |   | 4/1975 | King et al. | |

(Continued)

FOREIGN PATENT DOCUMENTS

| CN | 1142351 A | 2/1997 |
| CN | 106175845 A | 12/2016 |

(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

(Continued)

*Primary Examiner* — Thomas McEvoy
(74) *Attorney, Agent, or Firm* — Anya Adams

(57) ABSTRACT

In one representative embodiment, an implantable prosthetic device comprises a spacer body portion configured to be disposed between native leaflets of a heart, and an anchor portion configured to secure the native leaflets against the spacer body portion. The prosthetic device can be movable between multiple configurations. The spacer body can be configured to extend radially outwardly as the spacer body (Continued)

extends away from the distal end toward the proximal end. A delivery apparatus can have a first shaft and a second shaft, wherein movement of the first shaft relative to the second shaft moves the anchor portion relative to the spacer body.

18 Claims, 62 Drawing Sheets

Related U.S. Application Data

(60) Provisional application No. 62/161,688, filed on May 14, 2015.

(52) U.S. Cl.
CPC .... *A61F 2/2466* (2013.01); *A61F 2220/0016* (2013.01); *A61F 2310/00023* (2013.01)

(56) References Cited

U.S. PATENT DOCUMENTS

| | | | |
|---|---|---|---|
| 4,340,091 A | 7/1982 | Skelton et al. |
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,632,241 B1 * | 10/2003 | Hancock .......... A61B 17/12022 128/898 |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,875,224 B2 | 4/2005 | Grimes |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,618,449 B2 | 11/2009 | Tremulis et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,923 B2 | 7/2010 | St. Goar et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,811,296 B2 | 10/2010 | Goldfarb et al. |
| 7,824,443 B2 | 11/2010 | Salahieh et al. |
| 7,981,123 B2 | 7/2011 | Seguin |
| 7,988,724 B2 | 8/2011 | Salahieh et al. |
| 7,998,151 B2 | 8/2011 | St. Goar et al. |
| 8,029,518 B2 | 10/2011 | Goldfarb et al. |
| 8,052,592 B2 | 11/2011 | Goldfarb et al. |
| 8,052,749 B2 | 11/2011 | Salahieh et al. |
| 8,052,750 B2 | 11/2011 | Tuval et al. |
| 8,057,493 B2 | 11/2011 | Goldfarb et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,123,703 B2 | 2/2012 | Martin et al. |
| 8,133,239 B2 | 3/2012 | Oz et al. |
| 8,147,542 B2 | 4/2012 | Maisano et al. |
| 8,172,856 B2 | 5/2012 | Eigler et al. |
| 8,187,299 B2 | 5/2012 | Goldfarb et al. |

(56) References Cited

U.S. PATENT DOCUMENTS

| | | |
|---|---|---|
| 8,206,437 B2 | 6/2012 | Bonhoeffer et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,409,273 B2 | 4/2013 | Thornton et al. |
| 8,414,643 B2 | 4/2013 | Tuval et al. |
| 8,416,643 B2 | 4/2013 | Magee |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,500,761 B2 | 8/2013 | Goldfarb et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,764,774 B2 | 7/2014 | Sigmon, Jr. |
| 8,771,345 B2 | 7/2014 | Tuval et al. |
| 8,771,346 B2 | 7/2014 | Tuval et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,926,691 B2 | 1/2015 | Chau et al. |
| 8,945,177 B2 | 2/2015 | Dell et al. |
| 9,011,468 B2 | 4/2015 | Ketai et al. |
| 9,034,032 B2 | 5/2015 | McLean et al. |
| 9,044,246 B2 | 6/2015 | Goldfarb et al. |
| 9,138,312 B2 | 9/2015 | Tuval et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,414,918 B2 | 8/2016 | Chau et al. |
| 9,427,237 B2 | 8/2016 | Oz et al. |
| 9,427,327 B2 | 8/2016 | Parrish |
| 9,439,763 B2 | 9/2016 | Geist et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,188,392 B2 | 1/2019 | Wei |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,537,348 B2 | 1/2020 | Rodriguez-Navarro et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0069593 A1 | 4/2003 | Tremulis et al. |
| 2003/0130731 A1 | 7/2003 | Vidlund et al. |
| 2003/0144573 A1 | 7/2003 | Heilman et al. |
| 2003/0167071 A1 | 9/2003 | Martin et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0039435 A1 | 2/2004 | Hancock et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0167539 A1 | 8/2004 | Kuehn et al. |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0033446 A1 | 2/2005 | Deem et al. |
| 2005/0049618 A1 | 3/2005 | Masuda et al. |
| 2005/0070926 A1 | 3/2005 | Ortiz |
| 2005/0137688 A1 | 6/2005 | Salahieh et al. |
| 2005/0137690 A1 | 6/2005 | Salahieh et al. |
| 2005/0137698 A1 | 6/2005 | Salahieh et al. |
| 2005/0143767 A1 | 6/2005 | Kimura et al. |
| 2005/0154443 A1* | 7/2005 | Linder ............ A61F 2/97 623/1.11 |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0058871 A1* | 3/2006 | Zakay ............ A61F 2/246 623/2.18 |
| 2006/0058872 A1 | 3/2006 | Salahieh et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0173524 A1 | 8/2006 | Salahieh et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0038293 A1 | 2/2007 | St.Goar et al. |
| 2007/0093857 A1 | 4/2007 | Rogers et al. |
| 2007/0093890 A1 | 4/2007 | Eliasen et al. |
| 2007/0100356 A1 | 5/2007 | Lucatero et al. |
| 2007/0129737 A1 | 6/2007 | Goldfarb et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |

(56) References Cited

U.S. PATENT DOCUMENTS

| | | |
|---|---|---|
| 2007/0198038 A1 | 8/2007 | Cohen et al. |
| 2007/0203503 A1 | 8/2007 | Salahieh et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0167714 A1 | 7/2008 | St. Goar et al. |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0288061 A1 | 11/2008 | Maurer et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0048668 A1 | 2/2009 | Wilson et al. |
| 2009/0076598 A1 | 3/2009 | Salahieh et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121433 A1 | 5/2010 | Bolling et al. |
| 2010/0121434 A1 | 5/2010 | Paul et al. |
| 2010/0217283 A1 | 8/2010 | St. Goar et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137397 A1 | 6/2011 | Chau et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2011/0307055 A1 | 12/2011 | Goldfarb et al. |
| 2012/0010461 A1 | 1/2012 | Goldfarb et al. |
| 2012/0022633 A1 | 1/2012 | Olson et al. |
| 2012/0046741 A1 | 2/2012 | Tuval et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0282114 A1* | 10/2013 | Schweich, Jr. ....... A61F 2/2445 623/2.38 |
| 2013/0304197 A1 | 11/2013 | Buchbinder et al. |
| 2013/0304200 A1* | 11/2013 | McLean ................ A61F 2/2412 623/2.18 |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236187 A1 | 8/2014 | Seguin |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0296878 A1 | 10/2014 | Oz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105804 A1 | 4/2015 | Dell et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0182223 A1 | 7/2015 | Ketai et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0302920 A1* | 10/2016 | Al-Jilaihawi ......... A61F 2/2433 |
| 2016/0317290 A1 | 11/2016 | Chau et al. |
| 2016/0324634 A1 | 11/2016 | Gabbay |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |

(56) References Cited

U.S. PATENT DOCUMENTS

| | | |
|---|---|---|
| 2017/0100236 A1 | 4/2017 | Robertson et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0000582 A1 | 1/2018 | Tuval et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008638 A1 | 1/2019 | Siegel et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053803 A1 | 2/2019 | Ketai et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| EP | 1281375 A2 | 2/2003 |
| EP | 0879069 B1 | 8/2003 |
| EP | 1301235 B1 | 10/2004 |
| EP | 1583577 B1 | 5/2007 |
| EP | 1408850 B1 | 9/2009 |
| EP | 0930845 B1 | 10/2009 |
| EP | 1624810 B1 | 3/2011 |
| EP | 1804686 B1 | 9/2015 |
| EP | 2428169 B1 | 10/2016 |
| EP | 2266503 B1 | 1/2017 |
| EP | 2266504 B1 | 3/2017 |

(56) References Cited

FOREIGN PATENT DOCUMENTS

| | | |
|---|---|---|
| FR | 2146050 A5 | 2/1973 |
| FR | 2768324 A1 | 3/1999 |
| JP | 2014000417 A | 1/2014 |
| WO | 9802103 A1 | 1/1998 |
| WO | 9900059 A1 | 1/1999 |
| WO | 9913777 A1 | 3/1999 |
| WO | 0060995 A2 | 10/2000 |
| WO | 03001893 A2 | 1/2003 |
| WO | 2004103162 A2 | 12/2004 |
| WO | 2004103434 A2 | 12/2004 |
| WO | 2005112792 A2 | 12/2005 |
| WO | 2006115875 A2 | 11/2006 |
| WO | 2006116558 A2 | 11/2006 |
| WO | 2006138173 A2 | 12/2006 |
| WO | 2006047709 A3 | 7/2007 |
| WO | 2008147964 A1 | 12/2008 |
| WO | 2008150529 A1 | 12/2008 |
| WO | 2009024859 | 2/2009 |
| WO | 2009053952 A2 | 4/2009 |
| WO | 2009108942 A1 | 9/2009 |
| WO | 2009116041 | 9/2009 |
| WO | 2010098804 A1 | 9/2010 |
| WO | 2010128502 A1 | 11/2010 |
| WO | 2011034628 A1 | 3/2011 |
| WO | 2013016618 A2 | 1/2013 |
| WO | 2013059747 A1 | 4/2013 |
| WO | 2013173587 A1 | 11/2013 |
| WO | 2014064694 A2 | 5/2014 |
| WO | 2016110760 A1 | 7/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Michael D., et al., Transluminal Placement of Endovascular Stent-Grafts for the Treatment of Descending Thoracic Aortic Aneurysms, New Engl.J.Med., 1994; 331:1729-34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, <http://www.nytimes.com/1991/01/03/health/device-that-opens-clogged-arteries-gets-a-faili>. . ., Jul. 29, 2009, 2 pages.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der VerschluB des Ductus Arteriosus Persistens ohne Thorakotomie," Thoraxchirurgie Vaskulare Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rosch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Medécine et Hygiéne, Genève, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21,227-230.

Wheatley, M.D., David J., "Valve Prostheses," Rob & Smith's Operative Surgery, Fourth Edition, pp. 415-424, Butterworths 1986.

Batista RJ et al., "Partial left ventriculectomy to treat end-stage heart disease", Ann Thorac Surg., vol. 64, Issue-3, pp. 634-638, Sep. 1997.

Beall AC Jr. et al.,"Clinical experience with a dacron velour-covered teflon-disc mitral-valve prosthesis", Ann Thorac Surg., vol. 5, Issue 5, pp. 402-410, May 1968.

(56) References Cited

OTHER PUBLICATIONS

Fucci et al., "Improved results with mitral valve repair using new surgical techniques", Eur J Cardiothorac Surg. 1995;Issue9, vol. 11, pp. 621-626.
Maisano F et al., 'The edge-to-edge technique: a simplified method to correct mitral insufficiency', Eur J Cardiothorac Surg., vol. 13, Issue-3, pp. 240-245, Mar. 1998.
Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.
Reul RM et al., "Mitral valve reconstruction for mitral insufficiency", Prog Cardiovasc Dis., vol. 39, Issue-6, May-Jun. 1997.
Umaña JP et al., "Bow-tie'mitral valve repair: an adjuvant technique for ischemic mitral regurgitation', Ann Thorac Surg., vol. 66, Issue-6, pp. 1640-1646, Nov. 1998.
Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

\* cited by examiner

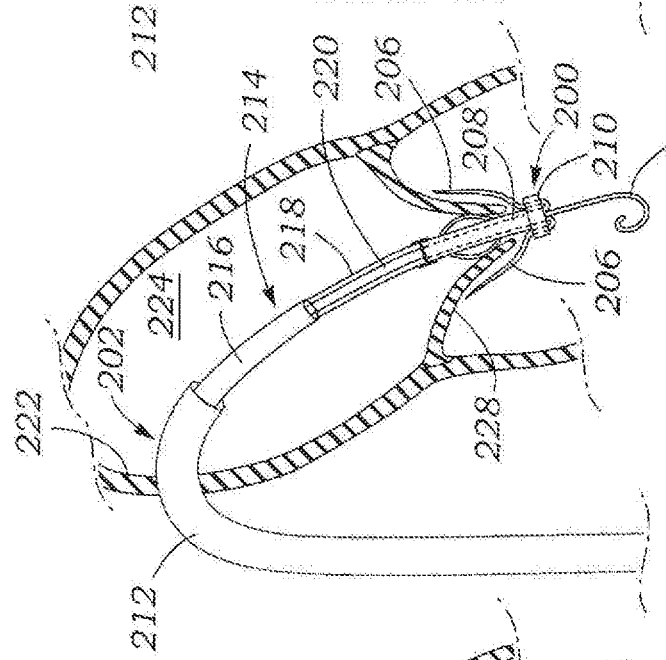
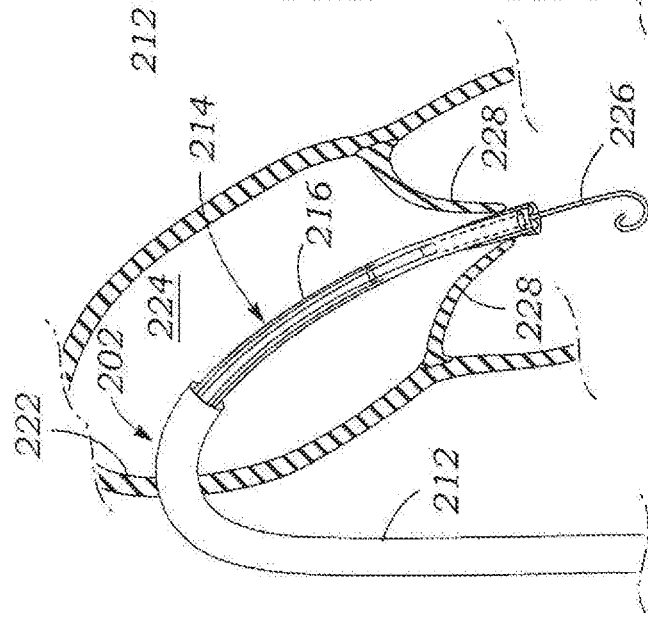

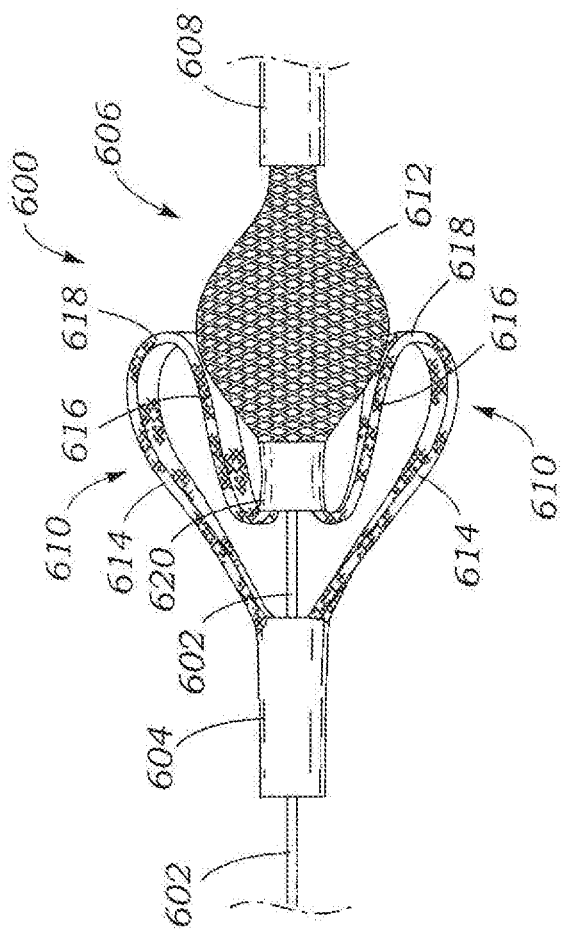
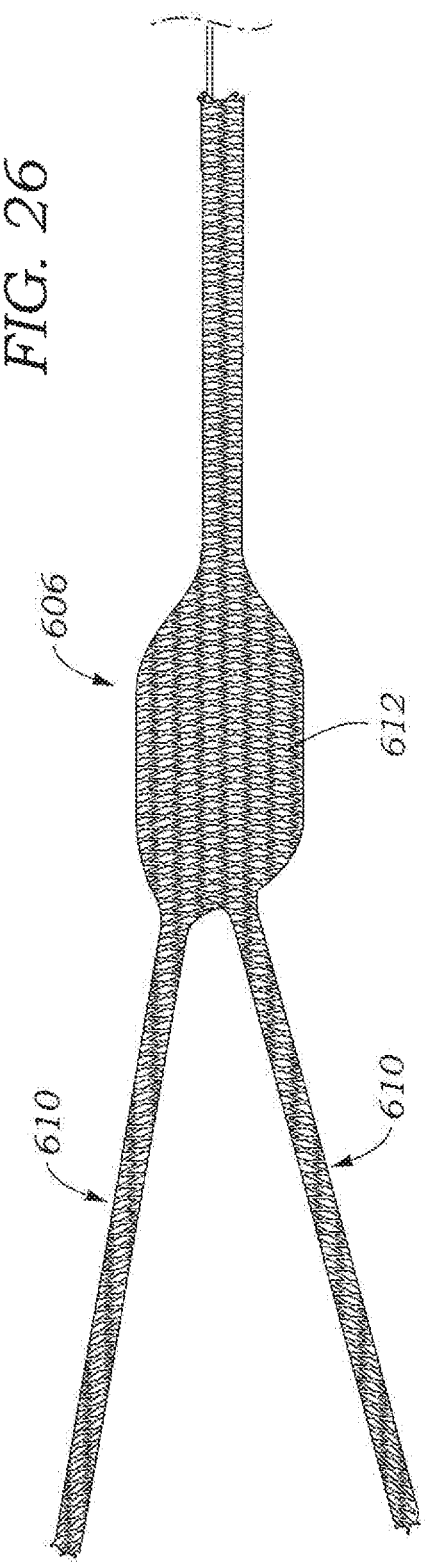

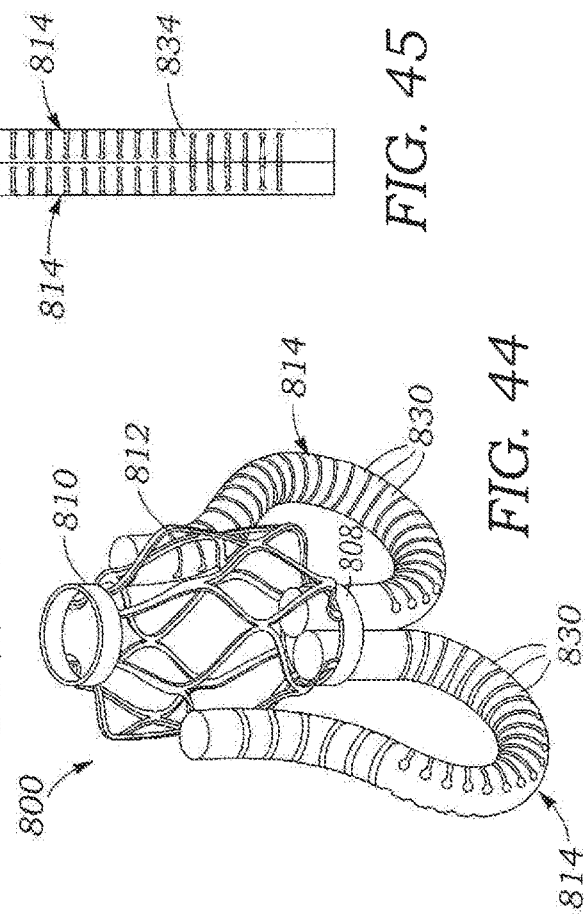
FIG. 45
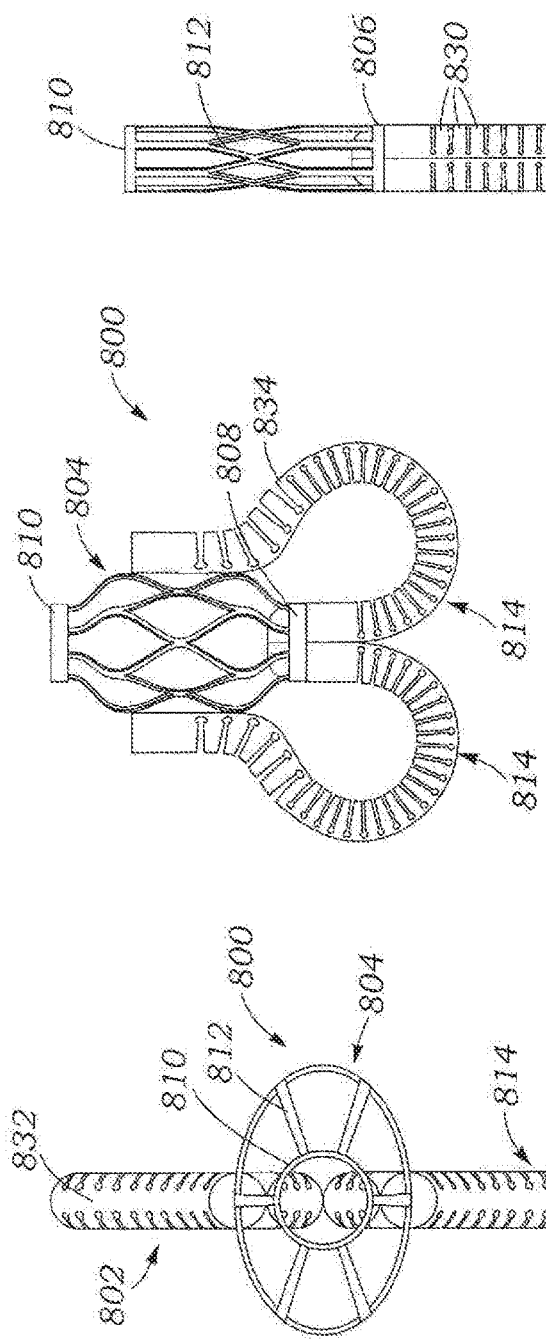
FIG. 42
FIG. 44
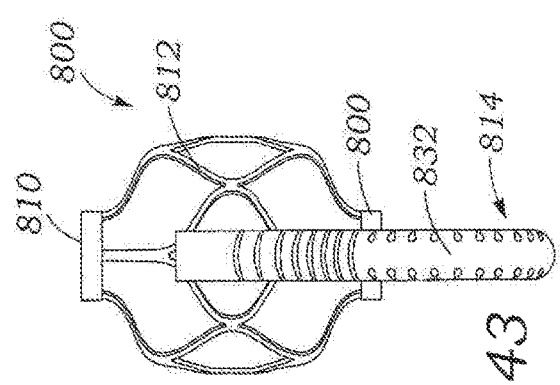
FIG. 41
FIG. 43

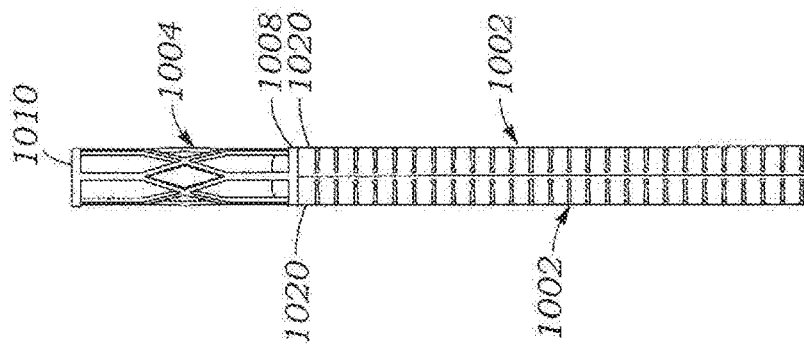
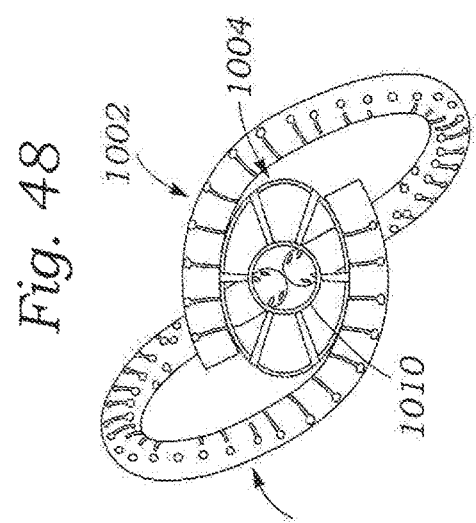
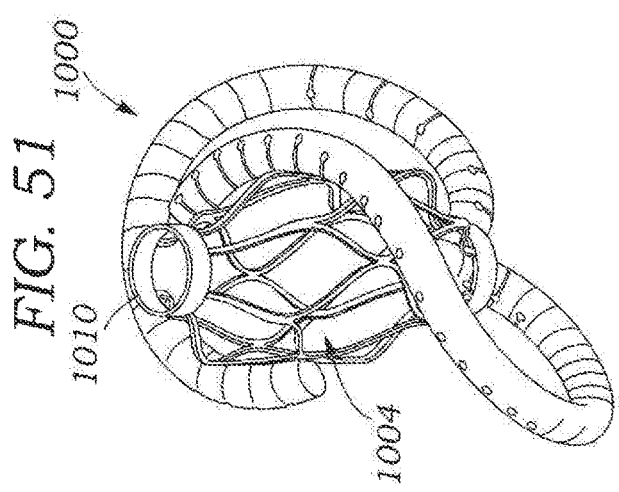

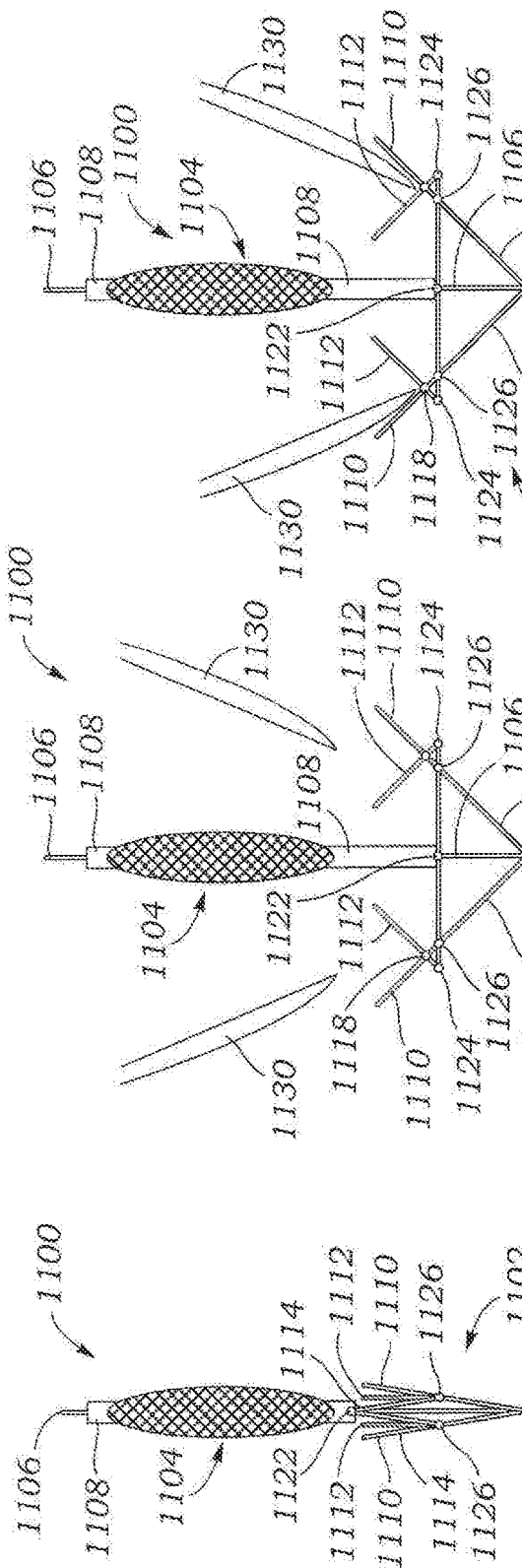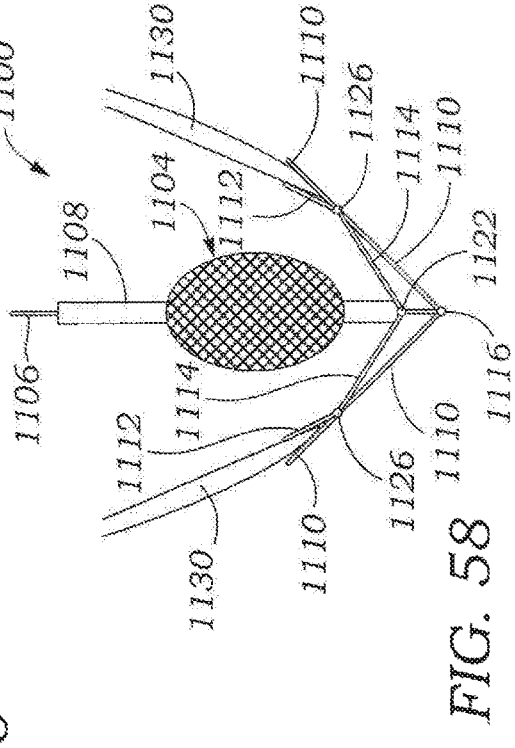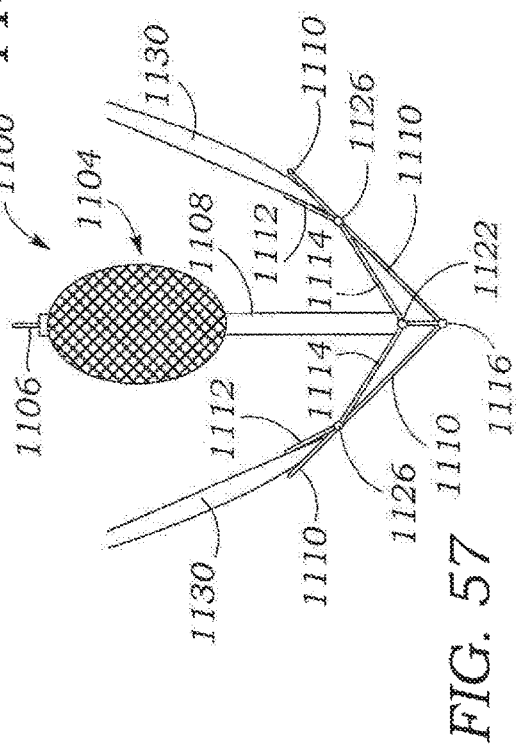

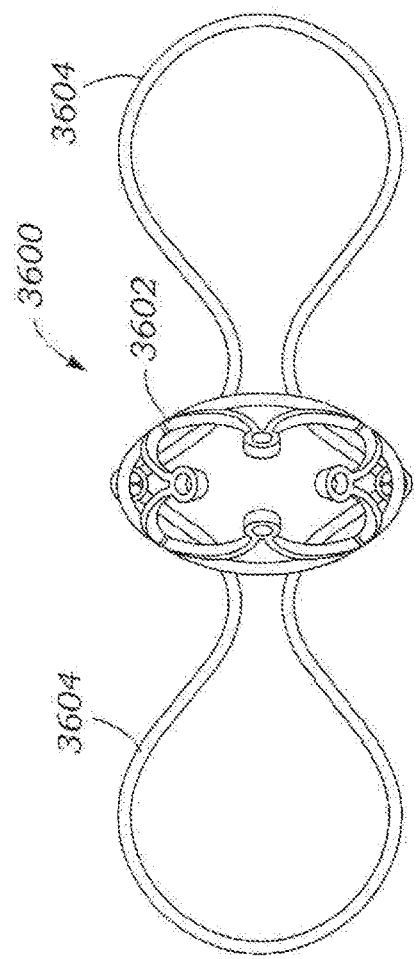
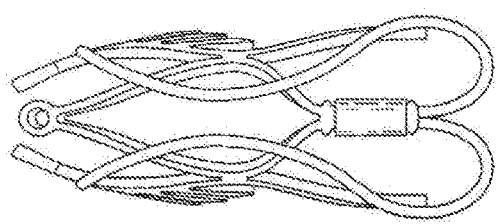
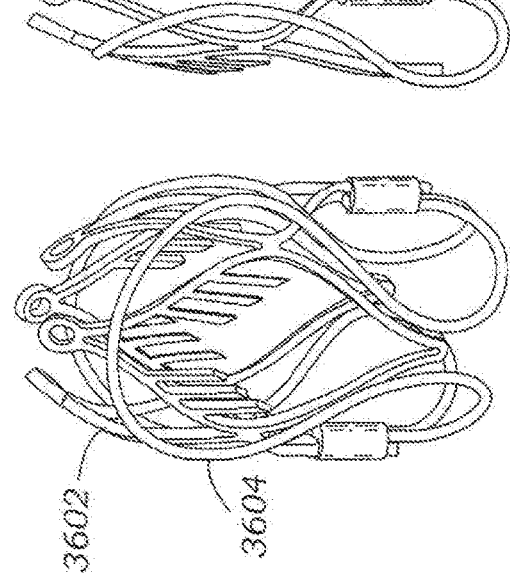
FIG. 119A
FIG. 119B
FIG. 119C
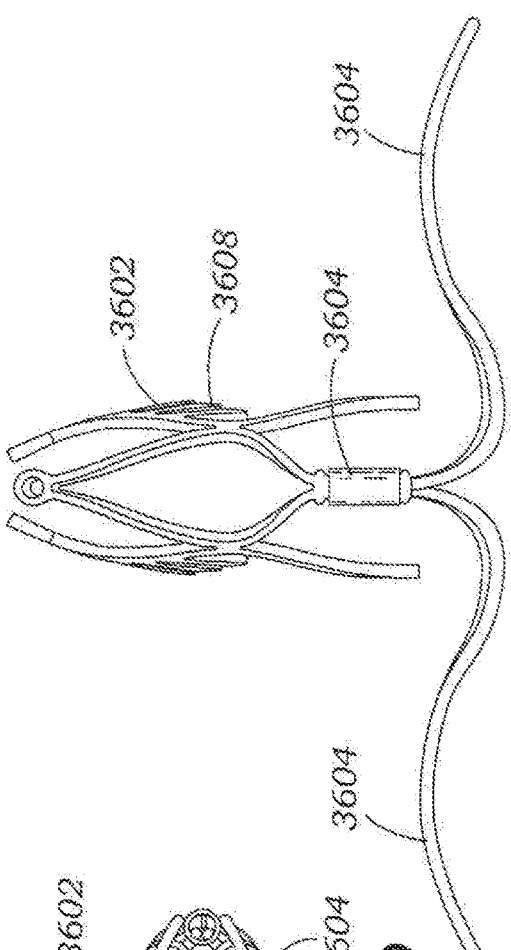
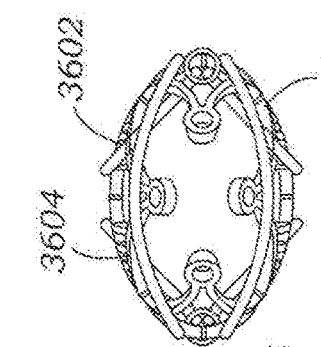
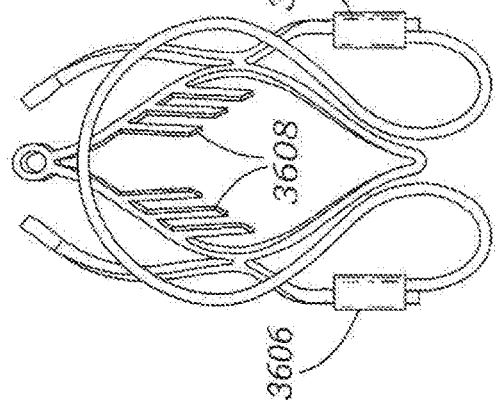
FIG. 119E
FIG. 119D
FIG. 119F

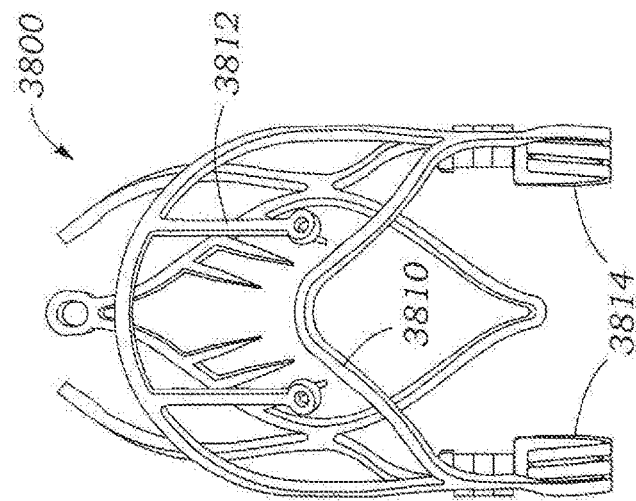
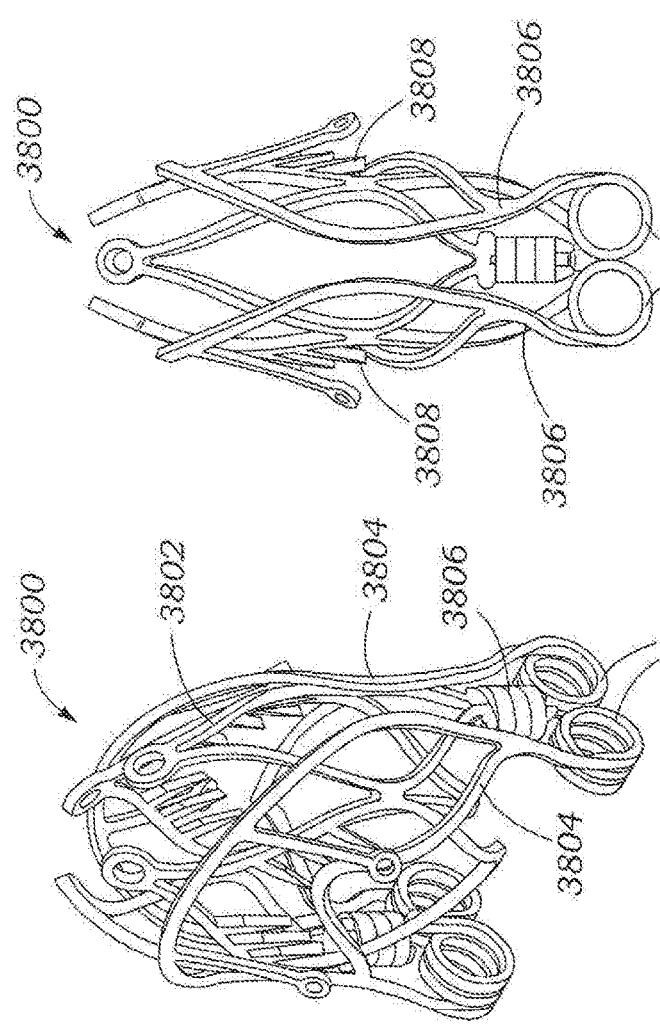
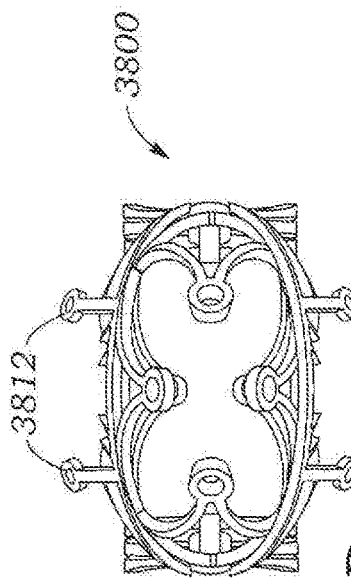
FIG. 121A   FIG. 121B   FIG. 121C
FIG. 121D

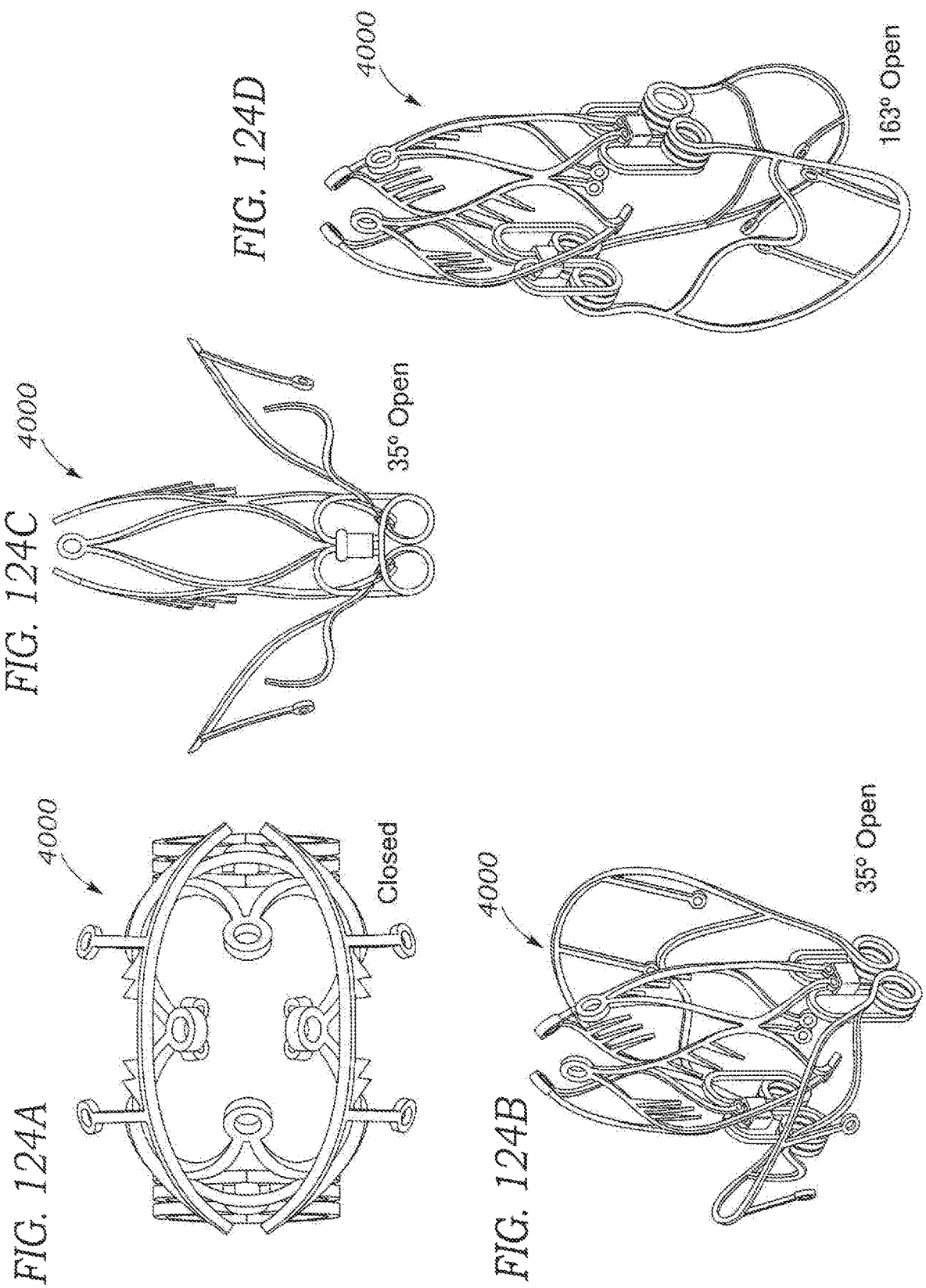

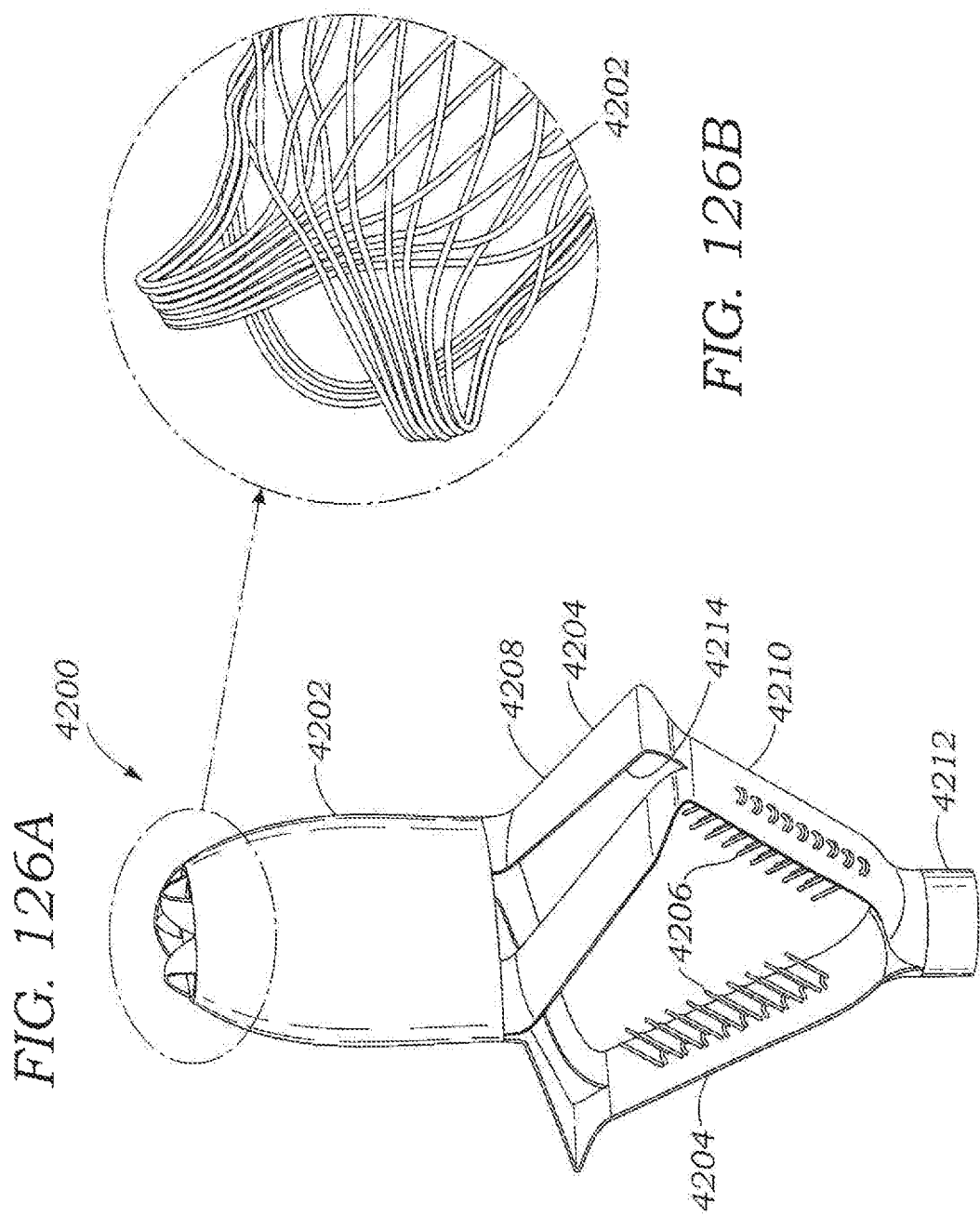

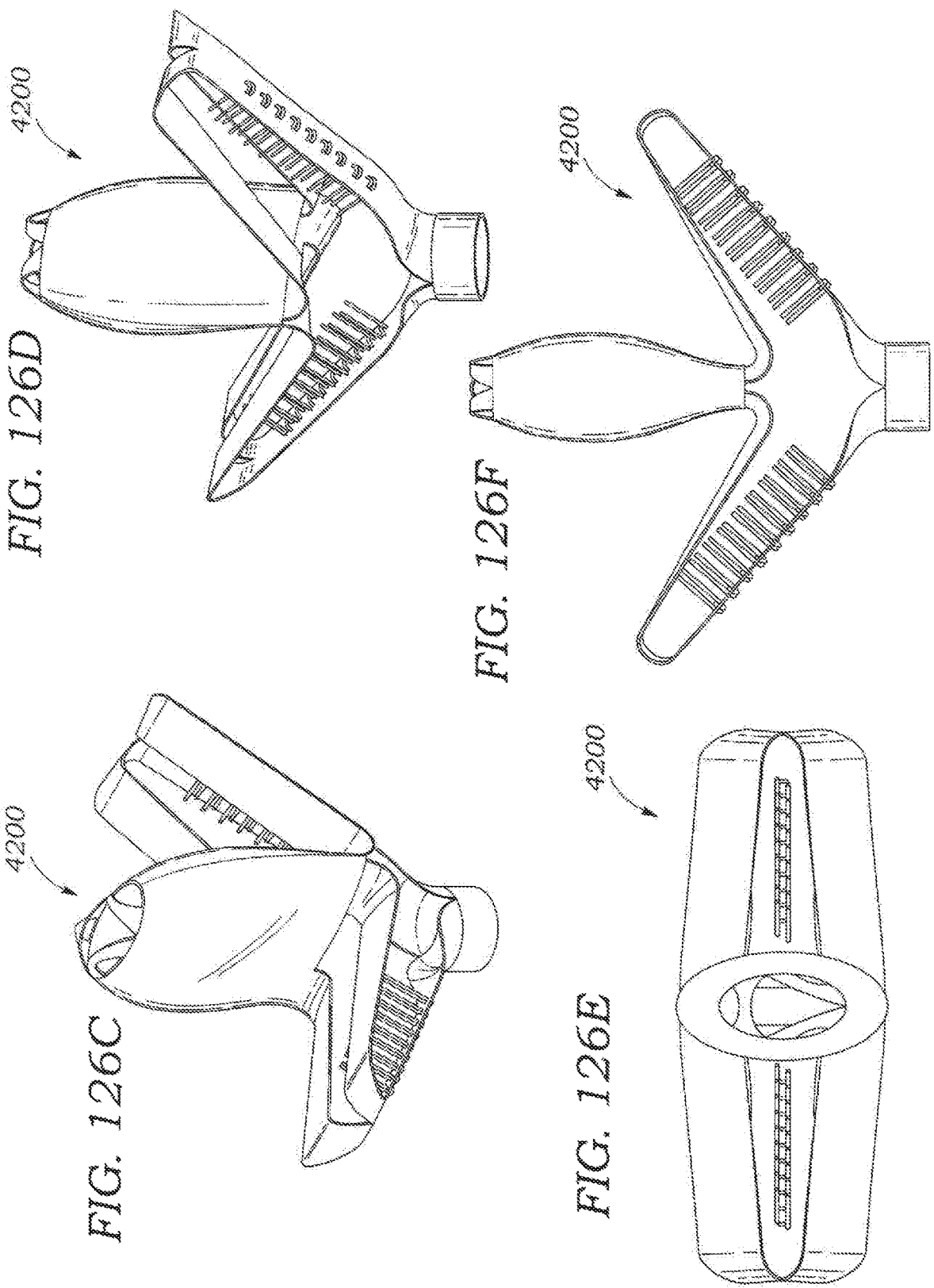

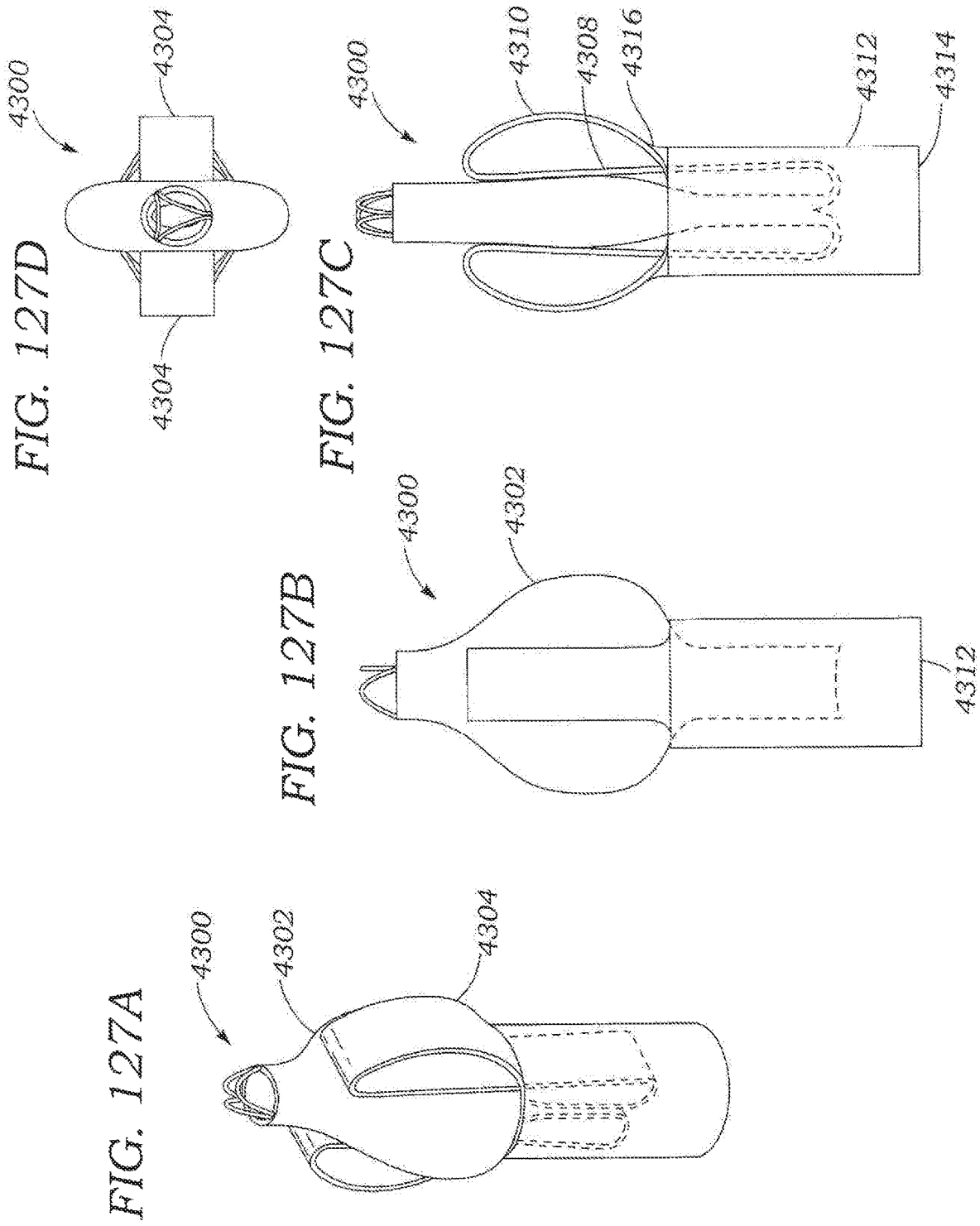

HEART VALVE SEALING DEVICES AND DELIVERY DEVICES THEREFOR

CROSS REFERENCE TO RELATED APPLICATIONS

This application claims the benefit of U.S. patent application Ser. No. 15/154,578, filed May 13, 2016, and U.S. Provisional Application No. 62/161,688, filed May 14, 2015, which is incorporated herein by reference.

FIELD

This disclosure pertains generally to prosthetic devices and related methods for helping to seal native heart valves and prevent or reduce regurgitation therethrough, as well as devices and related methods for implanting such prosthetic devices.

BACKGROUND

The native heart valves (i.e., the aortic, pulmonary, tricuspid and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another. Other prior techniques include the use of a spacer implanted between the native mitral valve leaflets. Despite these prior techniques, there is a continuing need for improved devices and methods for treating mitral valve regurgitation.

SUMMARY

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native mitral valve.

In one representative embodiment, an implantable prosthetic device comprises a spacer body portion configured to be disposed between native leaflets of a heart, and an anchor portion configured to secure the native leaflets against the spacer body portion, wherein the prosthetic device is movable between a compressed configuration, in which the spacer body portion is radially compressed and is axially spaced relative to the anchor portion, and an expanded configuration, in which the spacer body portion expands radially outwardly relative to the compressed configuration and overlaps at least a portion of the anchor portion.

In some embodiments, the anchor portion includes a plurality of anchor members, and the anchor members are each configured to secure a respective native leaflet against the spacer body portion. In some of those embodiments, the anchor members each have a first portion, a second portion, and a joint portion disposed between the first portion and the second portion, and wherein the first portions are spaced relative to the second portions in the compressed configuration and overlap with the second portions in the expanded configuration.

In some embodiments, the prosthetic device further comprising an end member axially spaced from and movable relative to the spacer body portion, wherein the first portions of the anchor members are pivotably coupled to an end portion of the spacer body portion, the second portions of the anchor members are pivotably coupled to the end member, and the anchor members are configured to be foldable at the joint portions when the spacer body portion is moved relative to the end member. In some embodiments, the anchor members are configured to fold at the joint portions from the compressed configuration to the expanded configuration when the spacer body portion is moved relatively closer to the end member, and the anchor members are configured to unfold at the joint portions from the expanded configuration to the compressed configuration when the spacer body portion is moved relatively farther from the end member.

In some embodiments, the prosthetic device further comprises a securing member having barbs coupled to one of the anchor members, wherein the securing member is configured to engage native leaflet tissue and to secure the native leaflet tissue to the one of the anchor members. In some of those embodiments, the securing member is pivotably coupled to the spacer body portion and the anchor portion.

In some embodiments, the anchor members are movable relative to each other. In some embodiments, the spacer body portion and the anchor portion are formed from a single, unitary piece of braided material. In some embodiments, the braided material comprises Nitinol. In some embodiments, the spacer body portion and the anchor portion are self-expandable. In some embodiments, the prosthetic device is configured for implantation in a native mitral valve and to reduce mitral regurgitation.

In another representative embodiment, an assembly is provided. The assembly comprises an implantable prosthetic device having a spacer body and a plurality of anchors, wherein first end portions of the anchors are coupled to a first end portion of the spacer body, and a delivery apparatus having a first shaft and a second shaft, wherein the first shaft and the second shaft are moveable relative to each other, wherein second end portions of the anchors are releasably coupled to the first shaft, and a second end portion of the spacer body is releasably coupled to the second shaft, wherein delivery apparatus is configured such that moving the first shaft and the second shaft relative to each moves the prosthetic device between a first configuration, in which the spacer body is radially compressed and is axially spaced relative to the anchors, and a second configuration, in which the spacer body expands radially outwardly relative to the compressed configuration and the anchors at least partially overlap the spacer body to capture native leaflets between the anchors and the spacer body.

In some embodiments, the first shaft of the delivery apparatus extends through the second shaft of the delivery apparatus and the spacer body of the prosthetic device, and the first shaft is axially movable relative to the spacer body. In some embodiments, the first shaft of the delivery apparatus is a plurality of anchor shafts, and each of the anchor shafts is releasably coupled to a respective anchor of the prosthetic device and is movable relative to other ones of the anchor shafts.

In some embodiments, the anchors each have a first portion, a second portion, and a joint portion disposed between the first portion and the second portion, and the first portion is spaced relative to the second portion in the first configuration and overlaps with the second portion in the second configuration. In some embodiments, the prosthetic device further comprises an end member spaced from and movable relative to the spacer body, wherein the first portions of the anchors are pivotably coupled to an end portion of the spacer body, the second portions of the anchors are pivotably coupled to the end member, and the anchors fold at the joint portions when the spacer body is moved relative to the end member. In some embodiments, the anchors fold at the joint portions from the compressed configuration to the expanded configuration when the spacer body moves relatively closer to the end member, and the anchors unfold at the joint portions from the expanded configuration to the compressed configuration when the spacer body portion moves relatively farther from the end member.

In some embodiments, the prosthetic device further comprises securing members having barbs coupled to the anchors and configured to engage native leaflet tissue to secure the anchors to native leaflets.

In another representative embodiment, a method of implanting a prosthetic device is provided. The method comprises advancing a prosthetic device in a compressed configuration to an implantation location using a delivery apparatus, wherein the prosthetic device comprises a spacer body, a first anchor, and a second anchor, radially expanding the prosthetic device from the compressed configuration to an expanded configuration, capturing a first native leaflet between two surfaces of the first anchor, capturing a second native leaflet between two surfaces of the second anchor, securing the first native leaflet and the second native leaflet against the spacer body of the prosthetic device, and releasing the prosthetic device from the delivery apparatus.

In some embodiments, the act of capturing the first native leaflet occurs prior to the act of capturing the second native leaflet, and the act of capturing the second native leaflet occurs prior to the act of securing the first native leaflet and the second native leaflet against the spacer body of the prosthetic device. In some embodiments, the act of capturing the first native leaflet occurs by actuating a first member of the delivery apparatus, and the act of capturing the second native leaflet occurs by actuating a second member of the delivery apparatus. In some embodiments, the first native leaflet and the second native leaflet are secured against the spacer body of the prosthetic device by moving a first shaft of the delivery apparatus relative to the second shaft of the delivery apparatus.

The foregoing and other objects, features, and advantages of the invention will become more apparent from the following detailed description, which proceeds with reference to the accompanying figures.

BRIEF DESCRIPTION OF THE DRAWINGS

FIGS. 6-8 show an implantable prosthetic device being delivered and implanted within the native mitral valve, according to one embodiment.

FIGS. 25-26 are side views of another embodiment of an implantable prosthetic device.

FIGS. 37-47 show various views of another embodiment of an implantable prosthetic device.

FIGS. 48-52 show various views of another embodiment of an implantable prosthetic device.

FIGS. 54-58 show the prosthetic device of FIG. 53 at various stages of deployment within the native mitral valve.

FIGS. 119A-119F show another exemplary embodiment of an implantable prosthetic device.

FIGS. 121A-121D show another exemplary embodiment of an implantable prosthetic device.

FIGS. 124A-124F show the prosthetic device of FIGS. 123A-123D in various stages of deployment.

FIGS. 126A-126J show another exemplary embodiment of an implantable prosthetic device.

FIGS. 127A-127F show another exemplary embodiment of an implantable prosthetic device.

DETAILED DESCRIPTION

Figure 1:
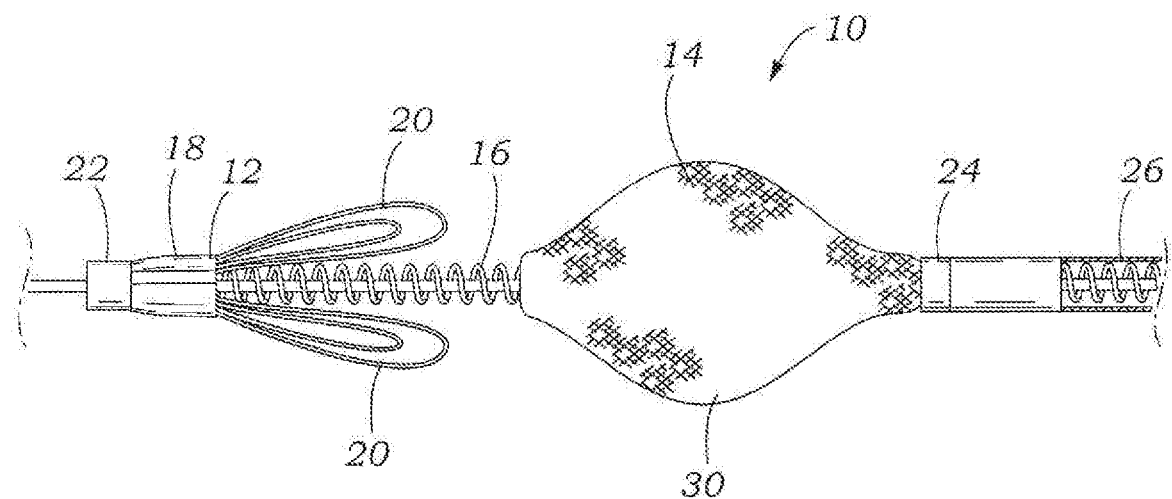
FIGS. 1-3 show an implantable prosthetic device, according to one embodiment, in various stages of deployment.

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native mitral valve. The disclosed embodiments should not be construed as limiting in any way. Instead, the present disclosure is directed toward all novel and nonobvious features and aspects of the various disclosed embodiments, alone and in various combinations and sub-combinations with one another.

Prosthetic Spacers

A prosthetic spacer device comprises a spacer body and at least one anchor. The body is configured to be positioned within the native mitral valve orifice to help create a more effective seal between the native leaflets to prevent or minimize mitral regurgitation. The body can comprise a structure that is impervious to blood and that allows the native leaflets to close around the sides of the body during ventricular systole to block blood from flowing from the left ventricle back into the left atrium. The body is sometimes referred to herein as a spacer because the body can fill a space between improperly functioning native mitral leaflets that do not naturally close completely.

The body can have various shapes. In some embodiments, the body can have an elongated cylindrical shape having a round cross-sectional shape. In other embodiments, the body can have an ovular cross-sectional shape, a crescent cross-sectional shape, or various other non-cylindrical shapes. The body can have an atrial or upper end positioned in or adjacent to the left atrium, a ventricular or lower end positioned in or adjacent to the left ventricle, and an annular side surface that extends between the native mitral leaflets.

The anchor can be configured to secure the device to one or both of the native mitral leaflets such that the body is positioned between the two native leaflets. In some embodiments, the anchor can attach to the body at a location adjacent the ventricular end of the body. In some embodiments, the anchor can attach to a shaft, to which the body is also attached. In some embodiments, the anchor and the body can be positioned independently with respect to each by separately moving each the anchor and the body along the longitudinal axis of the shaft. In some embodiments, the anchor and the body can be positioned simultaneously by moving the anchor and the body together along the longitudinal axis of the shaft. The anchor can be configured to be positioned behind a native leaflet when implanted such that the leaflet is captured between the anchor and the body.

The prosthetic device can be configured to be implanted via a delivery sheath. The body and the anchor can be compressible to a radially compressed state and can be self-expandable to a radially expanded state when compressive pressure is released. The device can be configured to allow the anchor to self-expand radially away from the still-compressed body initially in order to create a gap between the body and the anchor. A native leaflet can then be positioned in the gap. The body can then be allowed to self-expand radially, closing the gap between the body and the anchor and capturing the leaflet between the body and the anchor. The implantation methods for various embodiments can be different, and are more fully discussed below with respect to each embodiment. Additional information regarding these and other delivery methods can be found in U.S. Pat. No. 8,449,599 and U.S. Patent Application Publication Nos. 2014/0222136, and 2014/0067052, each of which is incorporated herein by reference in its entirety.

Some embodiments disclosed herein are generally configured to be secured to both the anterior and posterior native mitral leaflets. However, other embodiments comprise only one anchor and can be configured to be secured to one of the mitral leaflets. Unless otherwise stated, any of the embodiments disclosed herein that comprise a single anchor can optionally be secured to the anterior mitral leaflet or secured to the posterior mitral leaflet, regardless of whether the particular embodiments are shown as being secured to a particular one of the leaflets.

Some of the disclosed prosthetic devices are prevented from atrial embolization by having the anchor hooked around a leaflet, utilizing the tension from native chordae tendineae to resist high systolic pressure urging the device toward the left atrium. During diastole, the devices can rely on the compressive forces exerted on the leaflet that is captured between the body and the anchor to resist embolization into the left ventricle.

Figure 2:
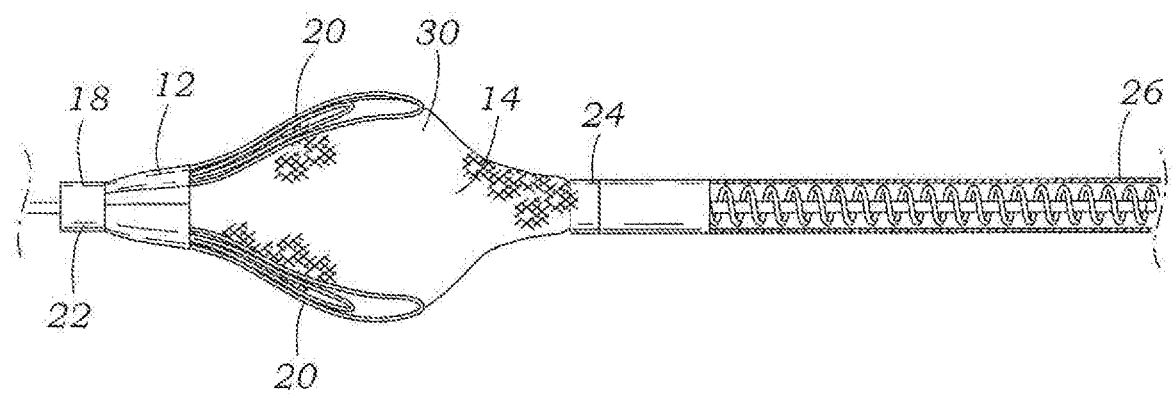
Figure 3:
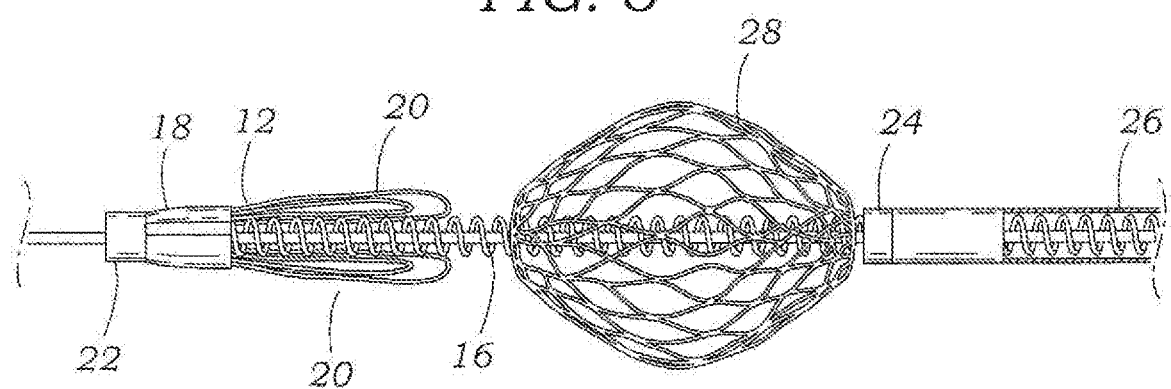

FIGS. 1-3 show an implantable prosthetic device 10, according to one embodiment. The prosthetic device 10 in the illustrated embodiment comprises a ventricular portion 12, a spacer body 14, and an inner shaft 16 on which the ventricular portion 12 and the spacer body 14 are mounted. The ventricular portion 12 includes a collar 18 disposed on the shaft 16 and one or more ventricular anchors 20 (two in the illustrated embodiment) extending from the collar 18. An end cap 22 can be mounted to the distal end of the shaft 16 to retain the ventricular portion 12 on the shaft.

The proximal end of the spacer body 14 is secured to a collar or nut 24, which is disposed on the shaft 16 proximal to the spacer body 14. Thus, the shaft 16 extends co-axially through the collar 24, the spacer body 14 and the collar 18 of the ventricular portion 12. The device 10 can further include an outer shaft or sleeve 26 that extends co-axially over a proximal end portion of the inner shaft 16 and is attached at its distal end to the collar 24. The inner shaft 16 is rotatable relative to the outer shaft 26 and the spacer body 14 to effect axial movement of the spacer body along the inner shaft 16 toward and away from the ventricular portion 12, as further described below.

The spacer body 14 can comprise an annular metal frame 28 (FIG. 3) covered with a blood-impervious fabric 30 (FIGS. 1 and 2). FIG. 3 shows the spacer body 14 without the blood-impervious fabric 30 covering the frame 28. The frame 24 can comprise a mesh-like structure comprising a plurality of interconnected metal struts, like a conventional radially compressible and expandable stent. In the illustrated configuration, the frame 28 has a generally spherical shape, although the frame can have various other shapes in other alternative embodiments (e.g., cylindrical, conical, etc.). In other embodiments, the body can comprise a solid block of material, such as flexible, sponge-like and/or elastomeric block of material formed, for example, from a biocompatible polymer, such silicone.

The frame 24 can be formed from a self-expandable material, such as Nitinol. When formed from a self-expandable material, the frame 24 can be radially compressed to a delivery configuration and can be retained in the delivery configuration by placing the device in the sheath of a delivery apparatus. When deployed from the sheath, the frame 24 can self-expand to its functional size. In other embodiments, the frame can be formed from a plastically expandable material, such as stainless steel or a cobalt chromium alloy. When formed from a plastically expandable material, the prosthetic device can be crimped onto a delivery apparatus and radially expanded to its functional size by an inflatable balloon or an equivalent expansion mechanism. It should be noted that any of the embodiments disclosed herein can comprise a self-expandable main body or a plastically expandable main body.

The inner shaft 16 can, for example, comprise a screw having external threads or a helical coil (as shown in FIGS. 1-3). The collar 24 has internal threads that engage the individual turns of the coil or in the case where the shaft comprises a screw, the external threads of the screw. Thus, rotation of the inner shaft 16 relative to the outer shaft 26 is effective to move the collar 24, and thus the spacer body 14, along the length of the shaft 16. Rotation of the inner shaft 16 relative to the outer shaft 26 can be accomplished by rotating a rotatable torque shaft of a delivery apparatus (such as shown in FIGS. 6-8) that is releasably connected to the inner shaft 16. The delivery apparatus can have a respective outer shaft that is releasably connected to the outer shaft 26 and configured to restrict rotation of the outer shaft 26 while the inner shaft 16 is rotated by the torque shaft.

The device 10 can be delivered percutaneously to a native heart valve (e.g., the mitral valve) with a delivery apparatus. FIG. 1 shows the spacer body 14 in a pre-anchored, proximal position spaced from the ventricular portion 12 prior to being mounted to the native leaflets of the mitral valve (the native leaflets are not shown in FIGS. 1-3). The anchors 20 are positioned in the left ventricle behind the native leaflets (e.g., desirably at the A2 and P2 regions of the leaflets, as identified by Carpentier nomenclature). The spacer body 14 is then moved toward the ventricular portion 12 (such as by rotating the torque shaft of the delivery apparatus) to the position shown in FIG. 2 such that the leaflets are captured between anchors 20 and the spacer body 14.

When the device 10 is secured to both of the leaflets, it brings them closer together around the spacer body 14. By so doing, the device 10 decreases the overall area of the mitral valve orifice and divides the mitral valve orifice into two orifices during diastole. Thus, the area through which mitral regurgitation can occur is reduced, leaflet coaptation can be initiated at the location of the body 14, and the leaflets can fully coapt more easily, thereby preventing or minimizing mitral regurgitation.

Due to the flexible nature of the body 14, the circumference and/or width/diameter of the spacer body 14 can be further expanded by urging the spacer body 14 against the ventricular portion 12 by rotation of the inner shaft 16. This action compresses the end portions of the body 14 between the anchors collar 24 and the collar 12, thereby causing the body 14 to foreshorten axially and the middle portion of the body 14 to expand radially. Conversely, moving the body 14 away from the ventricular portion 12 allows the body to contract radially.

The adjustability of device 10 provides several advantages over prior devices. For example, the device 10 can advantageously be used for varying degrees of mitral regurgitation because the device 10 can be configured to correspond to a various coaptation lines by expanding or contracting the body 14, thus reducing the need to manufacture multiple devices. Another advantage, for example, is that a physician can adjust the body 14 during the initial implant placement procedure to the desired configuration without extensive measuring and monitoring prior to the procedure. Whereas prior devices require extensive measuring prior to the placement procedure to ensure that a properly sized implant is selected, a physician can now adjust the size of the body 14 during the implant placement procedure by monitoring the procedure with an echocardiogram and adjusting the body 14 to the desired configuration and size.

The device 10 can also advantageously be adjusted subsequent to the initial placement procedure to reposition, expand, or contract the device 10 to achieve an improved result over the initial configuration. Yet another advantage of device 10 is that the anchors 12 and the body 14 can be positioned independently. This is advantageous over prior systems because it is often difficult to align the anchors and the body simultaneously due to the movement of the leaflets during diastole and systole.

The body 14 of device 10 can also be configured to address central and/or eccentric jet mitral regurgitation. Such configurations can comprise various sizes and/or geometries of the body 14.

Figure 4:
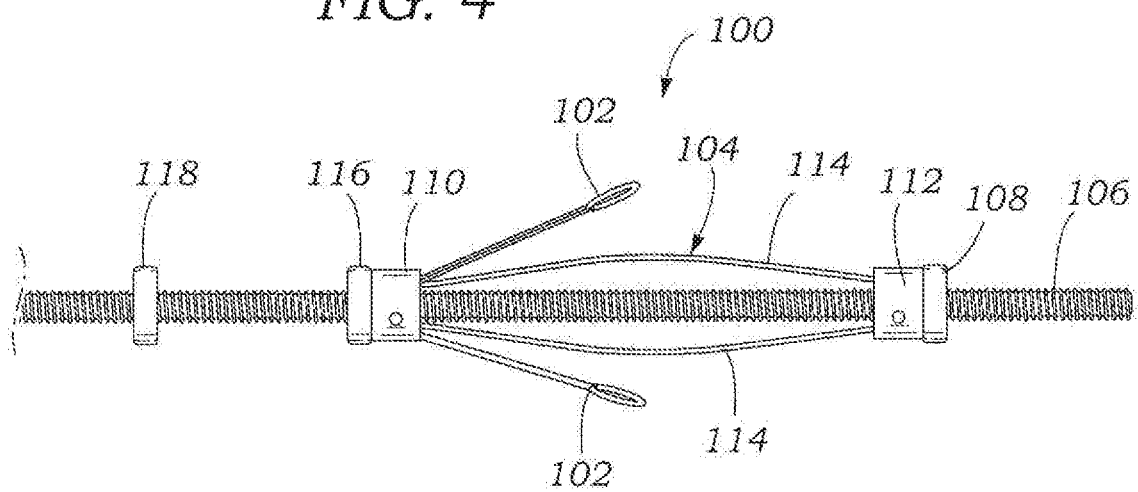
FIGS. 4-5 show an implantable prosthetic device, according to another embodiment, in various stages of deployment.
Figure 5:
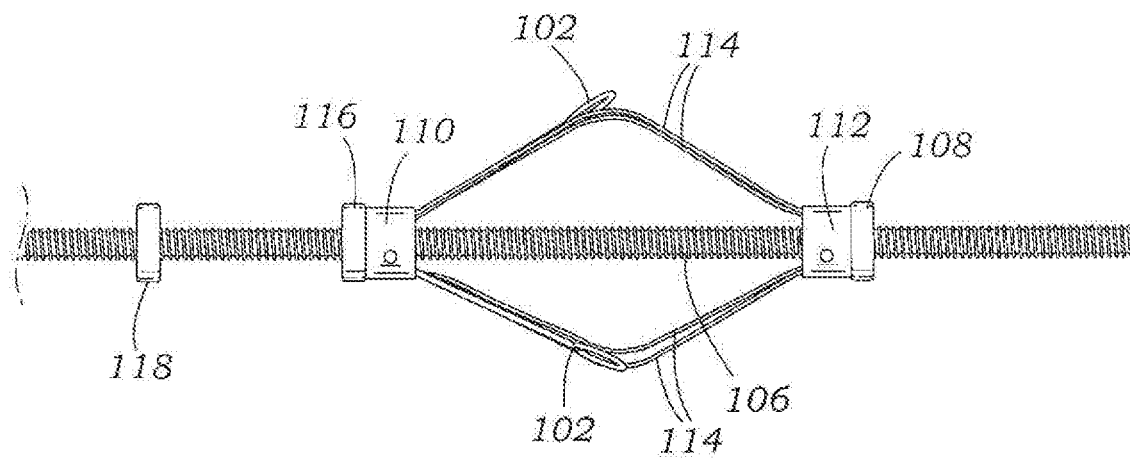

FIGS. 4 and 5 show another exemplary embodiment of an implantable prosthetic device 100. The device 100 comprises one or more ventricular anchors 102 (two in the illustrated embodiment), a spacer body 104, a threaded shaft 106, a proximal nut 108 and a distal stop 116. The shaft 106 extends co-axially through the body 104, the nut 108 and the stop 116.

The body 104 can comprise a distal, first annular collar 110 disposed around the shaft 106 and positioned towards the ventricular end of the body 104 of the device 100, a proximal, second annular collar 112 disposed around the shaft 106 and positioned towards the atrial end of the body 104 of the device 100, and a plurality of struts 114 extending between the first and second collars 110, 112.

The struts 114 can each be fixedly secured to the first collar 110 respective to first ends of the struts 114 and fixedly secured to the second collar 112 respective to second ends of the struts 114. The struts 114 can, for example, be fixedly secured to the collars 110, 112 by forming the struts 114 and the collars 110, 112 from a single, unitary piece of material (e.g., laser cutting a metal tube). In other embodiments, the struts 114 can, for example, be fixedly secured to the collars 110, 112 by an adhesive, welding, fasteners, etc. The anchors 102 are also fixedly secured to the distal collar 110, such as by welding, fasteners, an adhesive, or by forming the anchors and the collar from a single piece of material. Although not shown in FIGS. 4 and 5, the body 104 can be covered with a blood-impervious cover (e.g., a fabric), similar to the fabric 30 shown in FIGS. 1 and 2.

In the illustrated embodiment, the distal stop 116 can be fixed to the shaft 106 and functions to prevent distal movement of the distal collar 110 along the shaft 106 (to the left in FIGS. 4 and 5). The proximal collar 112 can be secured to the nut 108, which has internal threads that engage the external threads of the shaft 106. As such, rotation of the shaft 106 causes the nut 108, and therefore the proximal collar 112, to move toward and away from the distal collar 110, thereby radially expanding and contracting, respectively, the struts 114.

The anchors 102 and the struts 114 can be formed from a self-expandable material, such as Nitinol. When formed from a self-expandable material, the anchors 102 and the struts 114 can be radially compressed to a delivery configuration and can be retained in the delivery configuration by placing the device in the sheath of a delivery apparatus. When deployed from the sheath, the anchors 102 can radially expand, creating gaps between the anchors 102 and the struts 114, as shown in FIG. 4. In this configuration, the native leaflets of a heart valve can be placed in the gaps between the anchors 102 and the struts 114. The leaflets can then be secured between the anchors 102 and the struts 114 by moving the proximal collar 112 axially along the shaft toward the distal collar 110 through rotation of the shaft. As the proximal collar 112 is moved toward the distal collar 110, the struts 114 are caused to buckle or bow away from the longitudinal axis of shaft 106 toward the anchors 102 as shown in FIG. 5. The axial position of the proximal collar 112 can be adjusted until the anchors 102 and the struts 114 apply a clamping force against opposite sides of the leaflets, such that the device 100 maintains its position during diastole and systole, with respect to the leaflets.

Rotation of the shaft 106 relative to the nut 108 and the body 104 can be accomplished by rotating a rotatable torque shaft of a delivery apparatus (such as shown in FIGS. 6-8) that is releasably connected to the shaft 106. The delivery apparatus can have a respective outer shaft that is releasably connected to the nut 108 and configured to restrict rotation of the nut 108 while the shaft 106 is rotated by the torque shaft.

The shaft 106 shown in FIGS. 4 and 5 comprises a rigid bolt; however, the shaft 106 can comprise a flexible screw or a flexible helical coil similar to the shaft 16 shown in FIGS. 1-3.

In alternative embodiments, the position of the entire body 104 (including the proximal and distal collars 110, 112) can be adjusted axially along the length of the shaft 106 (in which case stop 116 is not fixed to the shaft 106). The position of the body 104 along the shaft can be accomplished by rotating the shaft 106 relative to the body, or vice versa. Once the desired position of the body 104 along the shaft 106 is attained, a stop member 118 can be positioned along the shaft in an abutting relationship with respect to the stop 116 (stop member 118 is shown spaced from the stop 116 in the figures) to prevent further distal movement of the body 104 along the shaft. Further rotation of the shaft 106 causes the proximal collar 112 to move toward the distal collar 110, causing the struts 114 to expand.

In another embodiment, a distal portion of the shaft 106 can be threaded in one direction and a proximal portion of the shaft 106 can be threaded in the opposite direction. The threads of the proximal portion of the shaft engage internal threads of the nut 108. The stop 116 similarly can comprise a nut having internal threads engaging the threads of the distal portion of the shaft. In this manner, rotation of the shaft relative to the body 104 in a first direction causes the distal and proximal collars 110, 112 to move toward each other, and rotation of the shaft relative to the body 104 in a second direction (opposite the first direction) causes the distal and proximal collars 110, 112 to move away from each other, similar to a turnbuckle.

FIGS. 6-8 show an implantable prosthetic device 200 according to another embodiment being deployed from a delivery apparatus 202 into the mitral valve via a transseptal technique. The prosthetic device 200 can comprise an expandable spacer body 204, one or more ventricular anchors 206 (two in the illustrated embodiment) coupled to and extending from a distal end portion of the spacer body 204, a shaft 208 extending through the spacer body 204, and a nut 210 disposed on the shaft 208. The nut 210 can have internal threads that engage external threads on the shaft 208 and can be restricted from rotational movement such that rotation of the shaft 208 causes axial movement of the nut 210 along the length of the shaft 208.

The delivery apparatus 202 can comprise an outer catheter 212 and an implant catheter 214. The implant catheter 214 can comprise a delivery sheath 216, a nut support shaft 218, and a torque shaft 220. Prior to insertion into the patient's body, the prosthetic device 200 can be connected to the nut support shaft 218 and the torque shaft 220 and loaded into the delivery sheath 216. The outer catheter 212 can be advanced through a femoral vein, the inferior vena cava, into the right atrium, across the septum 222 and into the left atrium 224 (as shown in FIG. 6). The outer catheter 212 can be advanced over a guide wire 226, which can be inserted into the patient's vasculature and used to cross the septum 222 prior to introducing the outer catheter 212 into the patient's body. As further shown in FIG. 6, the implant catheter 214, with the prosthetic device 200, can be inserted through the outer catheter 212 and into the left atrium 224. The implant catheter 214 can be advanced across the native mitral valve leaflets 228 until the anchors 206 of the prosthetic device are in the left ventricle.

As shown in FIG. 7, the delivery sheath 216 can then be retracted to expose the prosthetic device 200. The spacer body 204 can self-expand to a radially expanded state upon deployment from the delivery sheath 216. Alternatively, the spacer body 204 can be retained in a radially compressed state by the nut support shaft 218 when spacer body is deployed from the sheath 216. After deploying the prosthetic device 200 from the sheath 216, the torque shaft 220 can be rotated to open the anchors 206 to a desired position for capturing leaflets 226.

The anchors 206 can be positioned behind the leaflets 228 (e.g., desirably at the A2 and P2 positions). The leaflets 228 can then be secured between the anchors 206 and the spacer body 204 by rotating the torque shaft 220 and the shaft 208, causing the nut 210 to move axially along the anchors 206 in the proximal direction. Movement of the nut 210 is effective to urge the anchors 206 radially inwardly against the leaflets 228 (as shown in FIG. 8). Thus, the prosthetic device 200 can be secured the leaflets 228 by clamping the leaflets 228 between the anchors 206 and the body 204. Thereafter, as shown in FIG. 8, the nut support shaft 218 and the torque catheter 220 can be released from the prosthetic device and the implant catheter can be retracted into the outer catheter.

Figure 9:
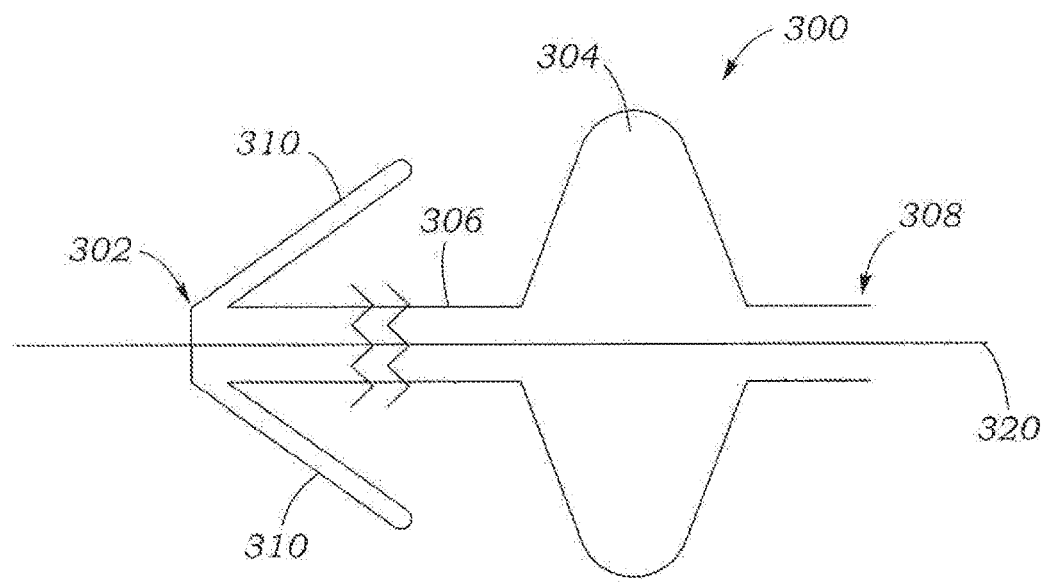
FIGS. 9-12 show various views of another embodiment of an implantable prosthetic device.

FIG. 9 shows an exemplary implantable prosthetic device 300, according to another embodiment. The prosthetic device 300 in the illustrated embodiment comprises a ventricular portion 302, a spacer body 304, a shaft 306, and a proximal end 308. The ventricular end portion 302 comprises one or more anchors 310 (two in the illustrated embodiment) extending from the ventricular end of the shaft 306. FIG. 9 also shows a guide wire 320 extending through the device 300. The guide wire 320 can be used during the device placement procedure (described below).

Figure 10:
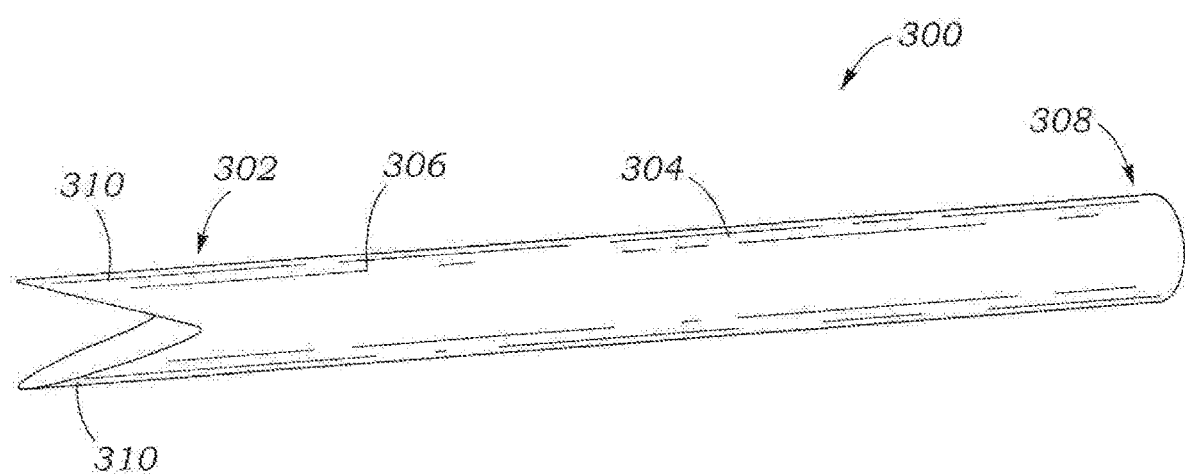

As shown in FIG. 10, the device 300 can be formed from a single, unitary piece of material. In some embodiments, the separate components of the device 300 can be formed from separate pieces of material that can be fixedly secured together by an adhesive, welding, fasteners, etc. The device 300 can be formed from a self-expandable braided material. The braided material can be formed from a metallic thread, such as Nitinol. When formed from a braided material, the device 300 can be covered with a blood-impervious cover (similar to the fabric 30 shown in FIGS. 1 and 2) or coated with a flexible sealant material, such as expanded polytetrafluoroethylene (commonly referred to as "ePTFE"), which allows the braided material to expand and/or bend while also preventing blood flow through the device 300.

In the illustrated embodiment, the body 304 of device 300 has a generally spherical shape, although the body 304 can have various other shapes in other embodiments (e.g., cylindrical, conical, etc.). The body 304 of device 300 can also be configured to address central and/or eccentric jet mitral regurgitation. Such configurations can comprise various sizes and/or geometries of the body 304. As shown, the body 304 of the device 300 can be an integral component of the device 300 formed from a single, unitary piece of self-expandable braided material, such as braided Nitinol. In other embodiments, the body 304 can be formed from a separate piece of material, including a different material such as a plastically expandable material or polymeric material (similar to those materials described in reference to spacer body 14 above).

When formed from a self-expandable braided material, the device 300 can be radially compressed to a delivery configuration (shown in FIG. 10) and can be retained in a delivery configuration by placing the device 300 in a sheath of a delivery apparatus. The device 300 can be radially compressed by axially elongating the device 300 by unfolding the anchors 310 such that the anchors 310 extend from the ventricular end of the shaft 306 away from the proximal end 308, parallel to the shaft 306, and by radially compressing the spacer body 304 to substantially the same diameter as the shaft 306, as shown in FIG. 10. With the device 300 in the delivery configuration, device 300 can be delivered percutaneously to a native heart valve (e.g., the mitral valve) with the delivery apparatus.

Figure 11:
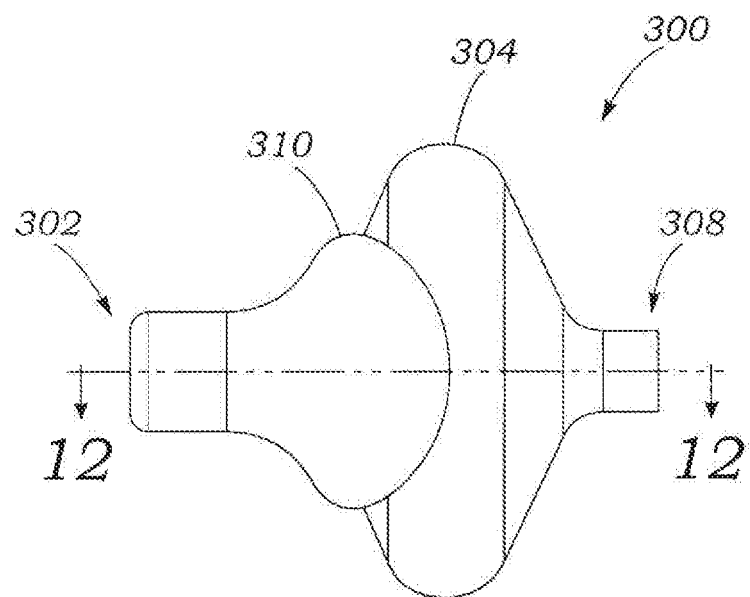
Figure 12:
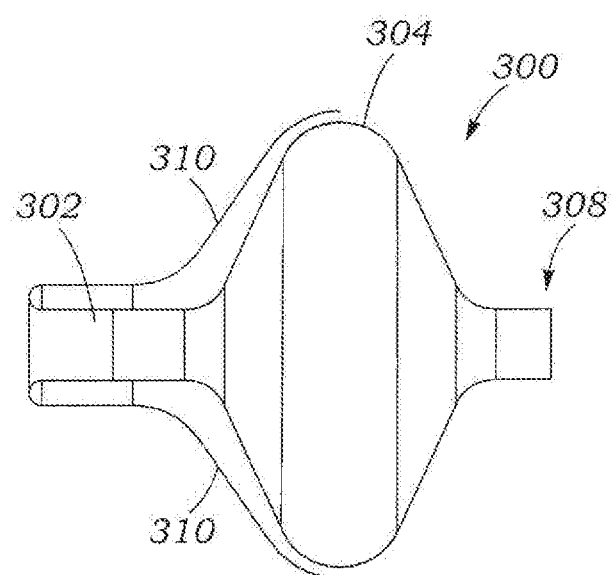

Once the device 300 is delivered percutaneously to a native heart valve with a delivery apparatus, the delivery sheath can be removed from the device 300, which allows the device 300 to fold and expand to its functional expanded state, shown in FIGS. 11 and 12. The native leaflets (not shown in FIGS. 11 and 12) are captured between anchors 310 and the spacer body 304 of the device 300, which brings them closer together around the spacer body 304. By so doing, the device 300 decreases the overall area of the mitral valve orifice and divides the mitral valve orifice into two orifices during diastole. Thus, the area through which mitral regurgitation can occur is reduced, leaflet coaptation can be initiated at the location of the body 304, and the leaflets can fully coapt more easily, thereby preventing or minimizing mitral regurgitation.

For example, FIGS. 13-17 show the device 300 being delivered to the mitral valve using a delivery apparatus 312. The delivery apparatus 312 can comprise an outer catheter (not shown) and a device catheter 314. The device catheter 314 can comprise a delivery sheath 316 and a shaft 318. Prior to insertion into the patient's body, the proximal end 308 of the device 300 can be releasably connected to the shaft 318 of the device catheter 314 and loaded into the delivery sheath 316, thus retaining the device 300 in the delivery configuration.

A guide wire 320 can be advanced through a patient's femoral vein, the inferior vena cava, into the right atrium, across the septum 322, into the left atrium 324, across the mitral valve leaflets 326, and into the left ventricle 328. The outer catheter can be advanced over the guide wire 320 and into the left atrium 324. The device catheter 314, with the device 300, can be advanced over the guide wire 320, through the outer catheter, and into to the left atrium 324. The device catheter 314 can be advanced across the mitral valve leaflets 326 until the anchors 310 of the device 300 are in the left ventricle 328.

Figure 13:
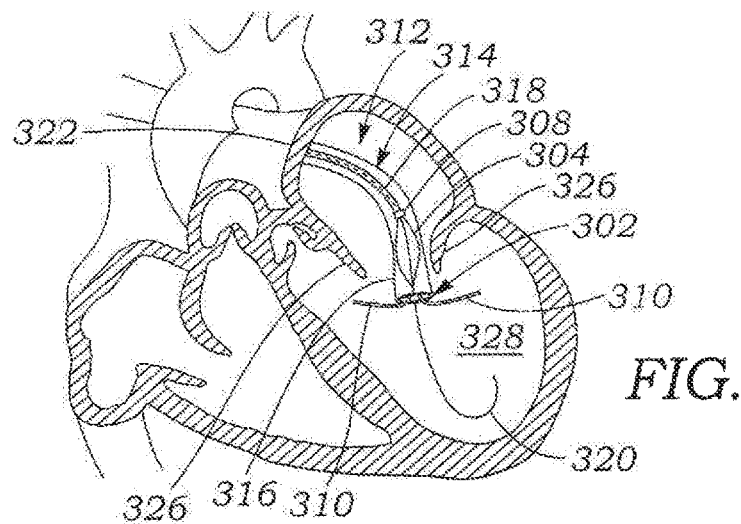
FIGS. 13-17 show the prosthetic device of FIGS. 9-12 being delivered and implanted within the native mitral valve.

As shown in FIG. 13, the delivery sheath 316 of the device catheter 314 can then be retracted to expose the anchors 310 of the device 300. Exposing the anchors 310 allows the anchors 310 to self-expand from the unfolded, radially compressed delivery configuration (shown in FIG. 10) to a folded, radially expanded configuration (shown in FIGS. 9, 11-12). With the anchors exposed, the shaft 318 of the delivery catheter 314 can be rotated to orient the anchors 310 to a desired position for capturing the leaflets 326.

Figure 14:
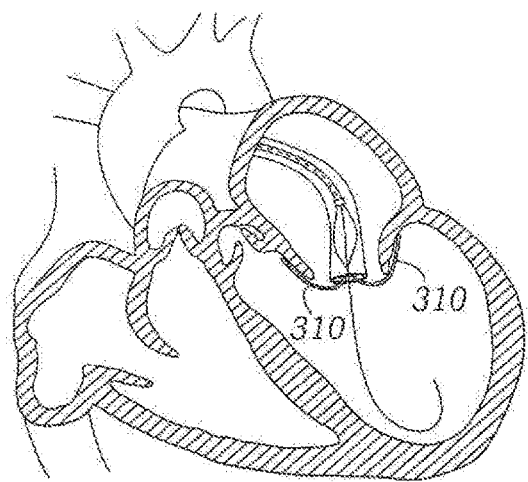
Figure 15:
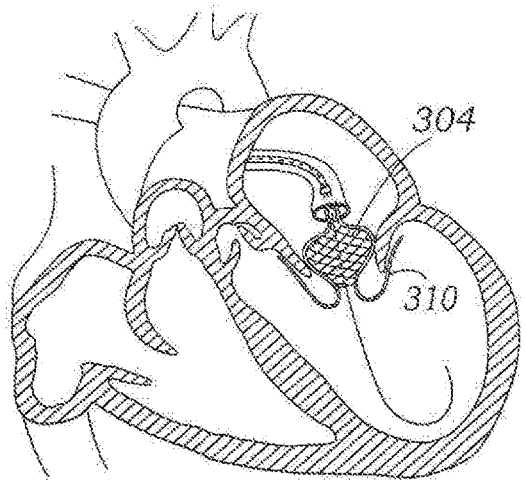

As shown in FIG. 14, the anchors can be positioned behind the ventricular portions of the leaflets 326 (e.g., desirably at the A2 and P2 positions). FIG. 15 shows that the delivery sheath 316 of the device catheter 314 can then be further retracted to expose the spacer body 304 of the device 300, allowing the body 304 to self-expand to a radially expanded configuration. In the expanded configuration, the body 300 of device 300 contacts the atrial portions of the leaflets 326. Thus, the leaflets are secured between the anchors 310 and the body 304 of the device 300 by clamping the leaflets 326 between the anchors 310 and the body 304 with the compressive forces applied by the anchors 310 and the body 304 to the ventricular and atrial portions of the leaflets 326, respectively.

Figure 16:
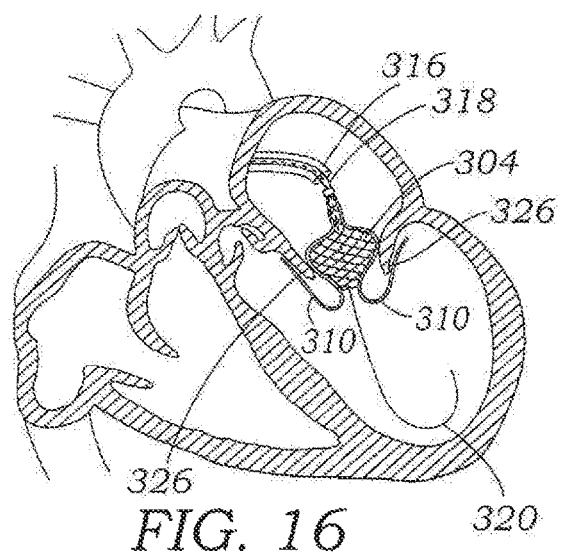
Figure 17:
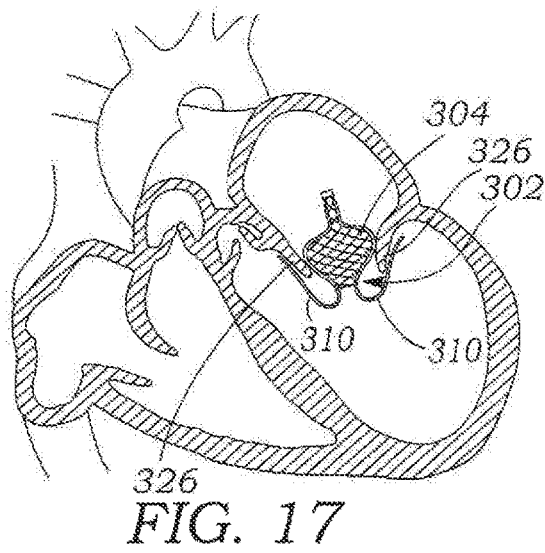

With the leaflets 326 secured between the anchors and the body, the shaft 318 of the device catheter 314 can be disconnected from the proximal end 308 of the device 300 (as shown in FIG. 16), and the device catheter 312 can be retracted into the outer catheter. The outer catheter and the guide wire 320 can then each be retracted and removed from the patient, as shown in FIG. 17. The device 300 can have an inner foam core such that when the guide wire 320 is retracted through the device, the inner foam of the device seals the guide wire lumen to prevent blood flow through the device 300.

Figure 18:
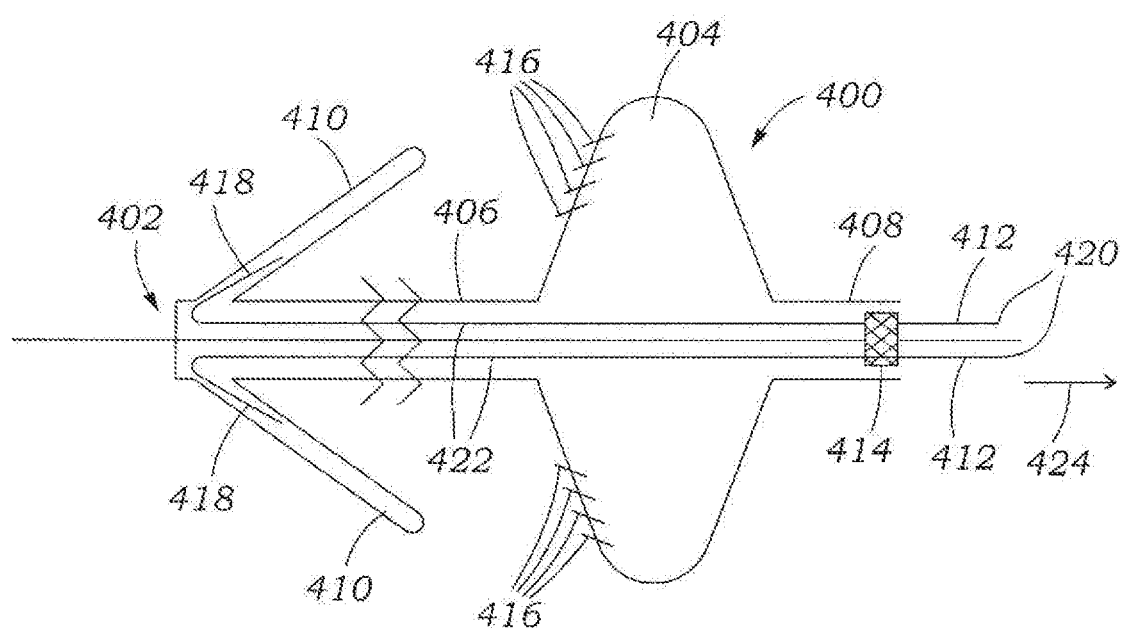
FIG. 18 is a side view of another embodiment of an implantable prosthetic device.
Figure 19A:
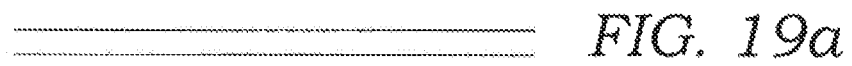
FIGS. 19*a*-19*h* show an exemplary heat-shaping process that can be used to form a prosthetic device, such as those shown in FIGS. 9-12 or FIG. 18.
Figure 19B:
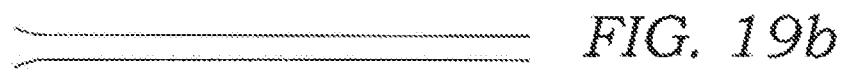
Figure 19C:
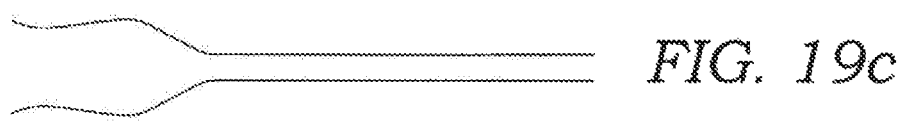
Figure 19D:
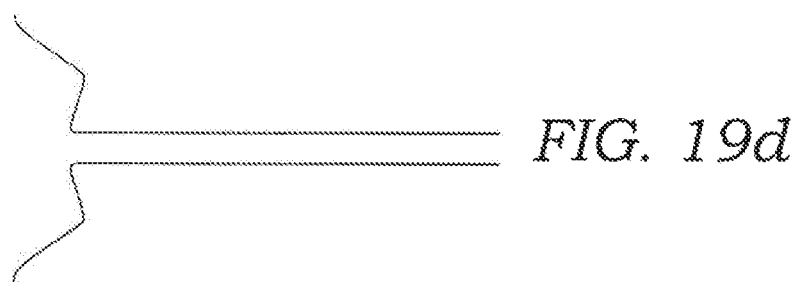
Figure 19E:
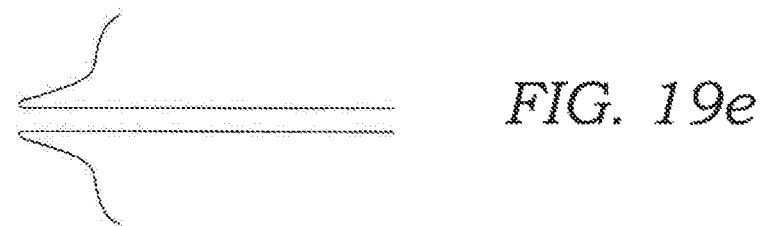
Figure 19F:
Figure 19G:
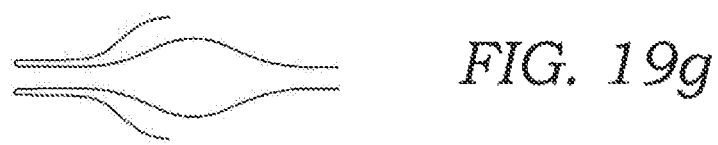
Figure 19H:

FIG. 18 shows an exemplary implantable prosthetic device 400 having an overall configuration similar to that of device 300, including a ventricular end portion 402, a spacer body 404, a shaft 406, and a proximal end portion 408. The ventricular end portion 402 comprises one or more anchors 410 (two in the illustrated embodiment) extending from the ventricular end portion 402. The spacer body 404 comprises a plurality of frictional elements 416. For example, each of the plurality of frictional elements 416 can comprises outwardly projections that can press into and/or penetrate leaflet tissue to minimize leaflet motion between the anchors 410 and the body 404 and improve tissue ingrowth, as shown in FIG. 18. In another embodiment, the frictional elements can comprise a textured surface formed in and/or applied to the blood-impervious covering of body 404.

The device 400 can also include one or more wires, sutures, tethers, or chords 412 (two in the illustrated embodiment) and a clip 414. The wires 412 can comprise distal ends 418, proximal ends 420 and intermediate portions 422 positioned between the distal ends 418 and the proximal ends 420. The distal end 418 of each of the wires 412 can be fixedly secured to a respective anchor 410 of the device 400 by an adhesive, welding, fastener, etc. The proximal ends 420 of the wires 412 can each be releasably connected to additional wires (not shown) of a delivery apparatus, respectively. The intermediate portions 422 of the wires 412 each extend co-axially through the shaft 406, the body 404, and the clip 414 of the device 400. The clip 414 can be fixedly secured to the proximal end 408 of the device 400 by adhesive, welding, fastener, etc. The clip 414 can also be adjustably-connected to the wires 412 and releasably connected to a delivery apparatus (not shown).

The device 400 can be delivered percutaneously to a native heart valve (e.g., the mitral valve) using a delivery apparatus and procedure similar to those described above with respect to device 300 (see FIGS. 13-17).

Due to the flexible nature of the device 400 and the addition of the wires 412 and clip 414, the clamping force on the leaflets can be further increased by applying a tensile force to the proximal ends 420 of the wires 412 (pulling the wires proximally in the direction of arrow 424) while maintaining the axial position of the clip 414. This action pulls the anchors 410 towards the body 404, thereby decreasing the space between the anchors 410 and the body 404. The tensile force can be applied to the proximal ends of the wires 412, for example, by pulling on additional wires of a delivery apparatus which can be releasbly connected to the proximal end of each wire 412 of the device 400. The clip 414 can be configured to retain the axial position of the wires 412 when the tensile force is removed. For example, the clip 414 can be configured to allow axial movement of the wires 412 in the proximal direction 424 but prevent axial movement of the wires 412 in the opposite direction when the tensile force is removed. In another embodiment, for example, the wires 412 can comprise teeth and the clip 414 can comprise pawls, forming a ratchet which only allows the wires 412 to move proximally with respect the clip 414.

FIG. 19 shows an exemplary heat forming sequence used to manufacture the devices 300, 400. The devices 300, 400 can be formed by placing a tubular piece of a braided self-expanding material over a mandrel(s) and then annealing the material in the configurations shown in FIG. 19a-h. When formed in this sequence, the devices expand in the same sequence when exposed from a delivery sheath.

FIGS. 20-24 show an exemplary embodiment of an implantable prosthetic device 500, which is similar to device 300, according to another embodiment. The prosthetic device 500 in the illustrated embodiment comprises a ventricular portion 502, a spacer body 504, and an inner shaft 506 on which the ventricular portion 502 and the spacer body 504 are mounted.

Figure 21A:
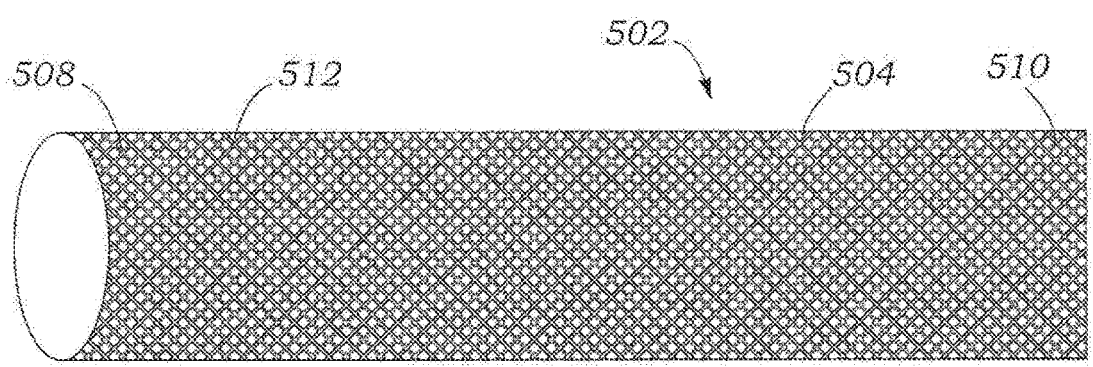
Figure 21B:
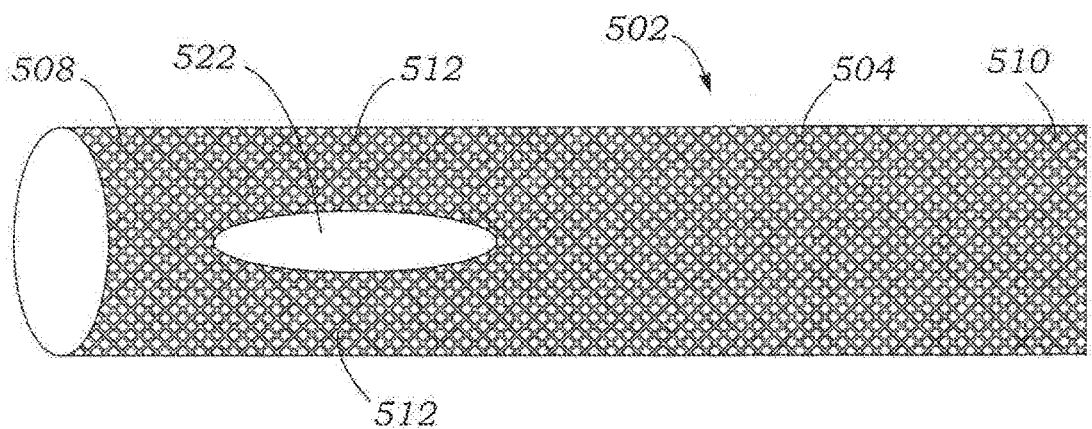
Figure 22:
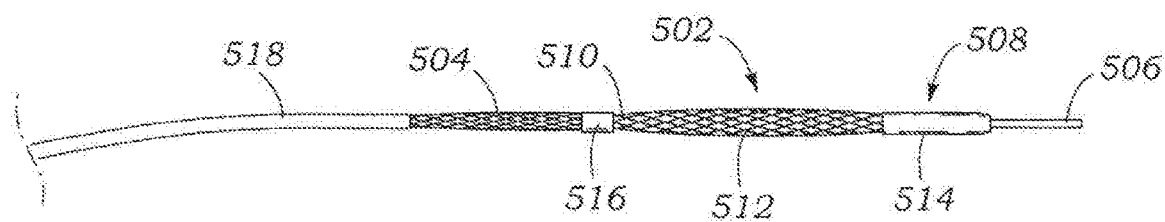

As best shown in FIG. 22 (which shows the device in a compressed delivery state), the ventricular portion 502 includes a distal end 508 and a proximal end 510 (shown in FIG. 22) each disposed on the shaft 506, and one or more ventricular anchors 512 (one in the illustrated embodiment) extending from the distal end portion 508. In some embodiments (shown in FIG. 21b), the ventricular portion 502 can also include a one or more openings 522 located near the distal end 508 of the ventricular portion 502. The device 500 as shown in FIG. 21b has two openings 522, however, because the openings are the same shape and size and located opposite each other (circumferentially) there only appears to be one opening. Such openings 522 effectively create multiple ventricular anchors 512 (two in FIG. 21b) when the ventricular portion 502 folds into a radially expanded functional state, as further described below. In alternative embodiments, the ventricular portion 502 of the device 500 can, for example, have three openings 520, effectively creating three anchors for use in a heart valve comprising three native leaflets (e.g., the tricuspid valve).

A distal sleeve 514 can be inserted over the distal end 508 of the ventricular portion 502 and mounted to the distal end of the shaft 506 to radially compress the distal end 508 against the inner shaft 506 and to retain the ventricular portion 502 on the shaft 506. The proximal end 510 of the ventricular portion 502 is attached to the distal end of an intermediate sleeve 516 (shown in FIG. 22), which is disposed on the shaft 506. The spacer body 504 is attached at its distal end to the proximal end of the intermediate sleeve 516 and at its proximal end to the distal end of a proximal sleeve or shaft 518, which extends co-axially over a proximal end of the inner shaft 506. Thus, the inner shaft 506 extends co-axially through the proximal sleeve 518, the spacer body 504, the intermediate sleeve 516, the ventricular portion 502, and the end cap 514. The inner shaft 506 is axially moveable relative to the proximal sleeve 518 and the intermediate sleeve 516 to effect expansion of the device during delivery of the device 500, as further describe below.

As shown, the ventricular portion 502 and the spacer body 504 of device 500 can be formed from a single, unitary piece of material. When the ventricular portion 502 and the spacer body 504 of device 500 are formed from a single piece of material, the intermediate sleeve 516 can be optional. In alternative embodiments, however, the ventricular portion 502 and the body 504 of device 500 can be formed from separate pieces of material. When the ventricular portion 502 and the spacer body 504 of device 500 are formed from separate pieces of material, the proximal end 510 of ventricular portion 502 and the distal end of the spacer body 504 can each be connected to intermediate sleeve 516 by adhesive, welding, fastener, etc. Alternatively, the proximal end 510 of ventricular portion 502 and the distal end of the spacer body 504 can each be connected directly together by adhesive, welding, fastener, etc. without the use of intermediate sleeve 516.

In the illustrated embodiment, the spacer body 504 of device 500 has a generally spherical shape, although the body 504 can have various other shapes in other embodiments (e.g., cylindrical, conical, etc.). The body 504 of device 500 can also be configured to address central and/or eccentric jet mitral regurgitation. It should be noted that any of the devices disclosed herein can comprise spacer bodies of various shapes and can be configured to address central and/or eccentric jet mitral regurgitation.

Figure 20:
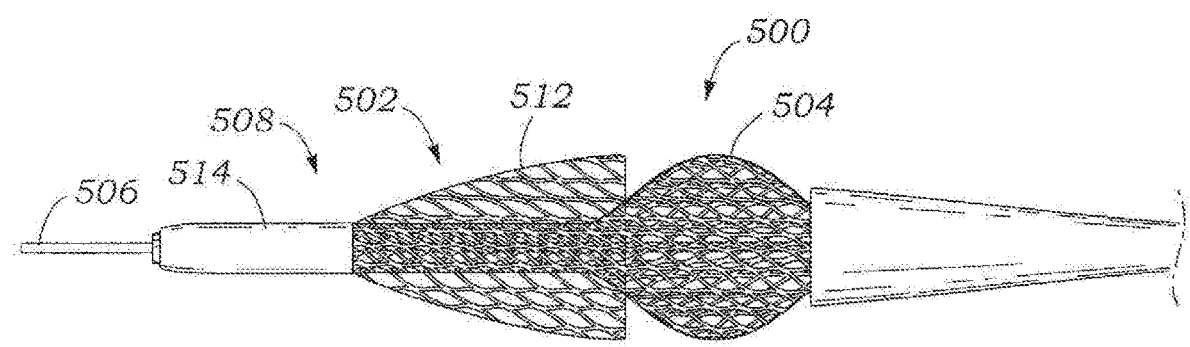
FIGS. 20-24 show various views of another embodiment of an implantable prosthetic device.

As shown in FIG. 20, the ventricular portion 502 and the spacer body 504 of device 500 can formed from a self-expandable braided material. The braided material can be formed from a metallic thread, such as Nitinol. Similar to devices described above, the braided material of the device 500 can be covered with a blood impervious cover or coated with a flexible sealant material to prevent blood flow through the device 500. FIG. 20 shows the device 500 in a radially expanded functional state. The device 500 can be radially compressed to a delivery configuration by moving the distal end 508 of the ventricular portion away from the proximal end of the spacer body 504, which effectively elongates or stretches the device into a radially compressed tubular configuration (as shown in FIGS. 21 and 22). With the device 500 in the delivery configuration, device 500 can be delivered percutaneously to a native heart valve (e.g., the mitral valve) similar to the delivery apparatus 312 described above.

Figure 23:
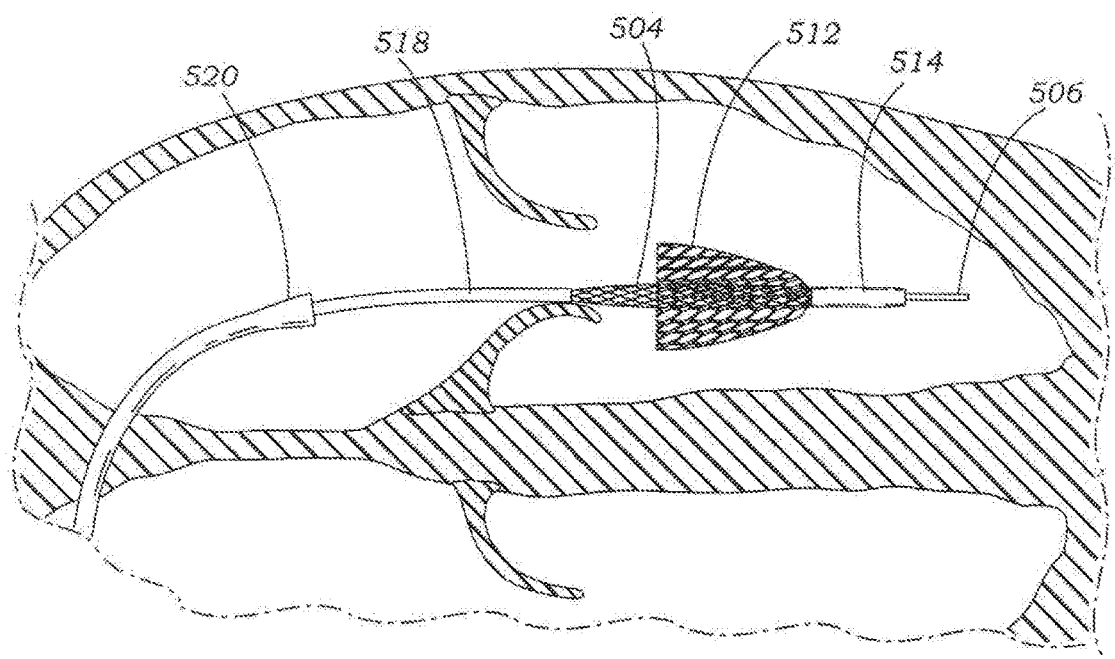

With a sheath 520 of the delivery apparatus in the left ventricle, the ventricular portion 502 of the device 500 can be advanced from the sheath of the delivery catheter by axially advancing the inner shaft 506 and the proximal sleeve 518 of the device 500 such that the ventricular portion 502 extends into the left ventricle from within the delivery sheath. The ventricular portion can then be folded and expanded by retracting the inner shaft 506 axially relative to the proximal sleeve 518 and the delivery sheath 520, as shown in FIG. 23. In this configuration, the anchors can be placed against the ventricular portions of the native leaflets.

Figure 24:
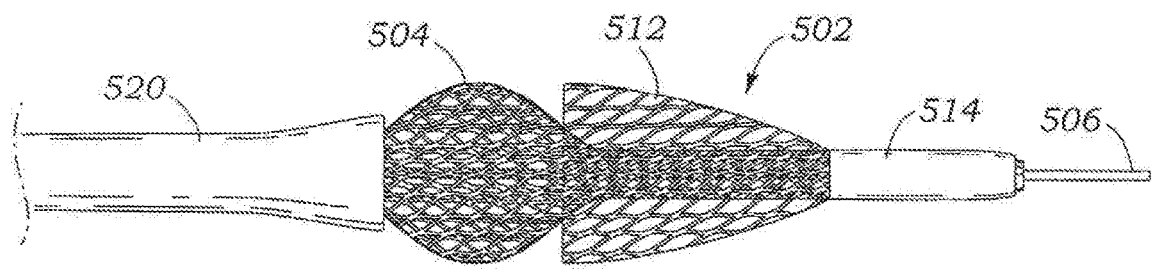

The leaflets can then be secured by retracting the proximal sleeve 518 axially relative to the inner shaft 506 and the delivery sheath 520, which causes the body 504 to expand radially, as shown in FIG. 24. With this action, the leaflets are captured between anchors 512 and the spacer body 504 of the device 300, which brings them closer together around the spacer body 504. By so doing, the device 500 decreases the overall area of the mitral valve orifice and divides the mitral valve orifice into two orifices during diastole. Thus, the area through which mitral regurgitation can occur is reduced, leaflet coaptation can be initiated at the location of the body 504, and the leaflets can fully coapt more easily, thereby preventing or minimizing mitral regurgitation. With the leaflets captured and the device 500 expanded to its functional state, the proximal sleeve 518 can be disconnected from the proximal end of the body 504 and retracted into the delivery sheath 520, both of which can then be retracted from the patient's body.

Although devices 300, 400, 500 show one or two anchors, in some embodiments, devices 300, 400, 500 can, for example, have three anchors and can be delivered to a native heart valve with three leaflets (e.g., the tricuspid valve). It should be noted that any of the embodiments disclosed herein can comprise one or more anchors.

FIGS. 25-34 show an exemplary embodiment of an implantable prosthetic device 600, which is similar to device 500, according to another embodiment. The prosthetic device 600 in the illustrated embodiment comprises an inner shaft 602, a distal end cap 604, a braided portion 606, and an outer shaft 608. The braided portion 606 includes one or more anchor portions 610 (two in the illustrated embodiment) and a body portion 612. The inner shaft 602 extends co-axially through the outer shaft 608, the body 612 of the braided portion 606, and the end cap 604. The end cap 604 can be fixedly secured to the distal end of the inner shaft 602 to prevent axially movement of the end cap 604 along the inner shaft 602.

Each of the anchors 610 of the braided portion 606 comprise lower leg portions 614, upper leg portions 616, and joints 618 positioned between each lower leg 614 and upper leg 616, respectively, defined by the folds in the leg portions when deployed. The distal ends of the lower legs 614 can be fixedly secured into the end cap 604 to retain them against, and prevent axial movement relative to, the inner shaft 602. The proximal ends of the upper legs 616 can be attached to the distal end of body 612 of the braided portion 606. The proximal end of the body 612 of the braided portion 606 can be releasably attached to the distal end of the outer shaft 608 by inserting the proximal end of the body 612 into the distal end of the outer shaft 608 or by a separate retaining device that couples the proximal end of the body to the end of the outer shaft 608. The outer shaft 608, and thus the body 612, can be adjustably moveable axially relative to the inner shaft 602 to effect the configuration of the device 600 during the device placement procedure, as further described below.

The end cap 604 can be fixedly secured to the distal end of the inner shaft 602, for example, by adhesive, welding, fasteners, etc. Alternatively, the end cap 604 can be fixedly secured to the distal end of the inner shaft 602, for example, by forming the end cap 604 and the inner shaft 602 from a single, unitary piece of material.

In some embodiments, the anchors 610 can be independently moveable relative to each other. For example, the device 600 can have a plurality of inner shafts 602 that are independently movable relative to each other, and each of the anchors 610 can each be coupled to a respective inner shaft 602.

The outer shaft 608 can be adjustably moveable axially relative to the inner shaft 602, such as by pushing or retracting the outer shaft 608 axially relative to the inner shaft, or vice versa. In an alternative embodiment, for example, the inner shaft 602 can comprise external threads and the outer shaft 608 can comprise internal threads that engage the external threads of the inner shaft 602. Thus, rotation of the outer shaft 608 relative to the inner shaft is effective to move the outer shaft 608, and thus the spacer body 612, along the length of the inner shaft 602.

Figure 27:
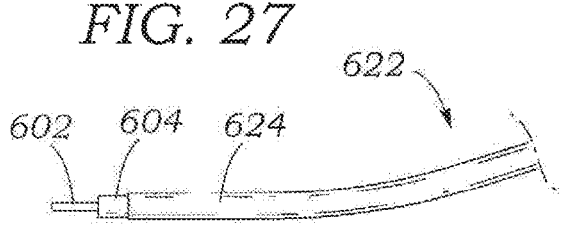
FIGS. 27-34 show various views of the prosthetic device of FIGS. 25-26 at different stages of deployment.

The braided portion 606 of the device 600 can be formed from a single, unitary piece of braided material. The braided material can be formed from a self-expandable metallic thread, such as Nitinol. For example, FIG. 26 shows the braided portion 606 of the device 600 formed from a single piece of braided material with the anchor portions 610 extended in an unfolded configuration and the body 612 slightly expanded. In an alternative embodiment, the anchors 610 and the body 612 can be formed from separate pieces of braided material, in which case the anchors 610 and the body 612 can be connected by attaching the proximal ends of the upper legs 616 of the anchors 610 and the distal portion of the body 612 to a connecting sleeve 620 (shown in FIG. 25). When formed from a self-expandable material, the braided portion 606 can be radially compressed to a delivery configuration and can be retained in the delivery configuration by placing the device 600 in the sheath of a delivery apparatus, as shown in FIG. 27. When deployed from the delivery sheath, the braided portion 606 of the device 600 can self-expand to a functional configuration, as further described below.

The device 600 can be delivered percutaneously to a native heart valve (e.g., the mitral valve) with a delivery apparatus. FIGS. 27-34 show the device 600 being deployed from a delivery apparatus. The delivery apparatus can comprise an outer catheter (e.g., outer catheter 520 of FIG. 23) and an implant catheter 622. The implant catheter 622 can comprises a delivery sheath 624, an inner shaft (not shown), and an outer shaft 608 (shown in FIG. 25). The inner shaft and the outer shaft 608 extend co-axially through the delivery sheath 624 of the implant catheter 622, and the inner shaft extends co-axially through the outer shaft 608 of the implant catheter 622.

Prior to insertion into the patient's body, the proximal end of the inner shaft 602 of the prosthetic device 600 can each be connected to the distal end of inner shaft (not shown) of the implant catheter 622, the outer shaft 608 can be coupled to the proximal end of the spacer body 612, and then the prosthetic device 600 can be loaded into the delivery sheath 624. The delivery apparatus can then be advanced in a patient's heart (not shown) via, for example, the transseptal technique described above (see FIGS. 6-8). FIG. 27 shows the sheath 624 of the implant catheter 622 restraining the prosthetic device 600 in the delivery configuration, In this configuration, the implant catheter can be advanced across the native mitral valve leaflets of a heart (not shown) until the distal end of the inner shaft 602 and the end cap 604 of the device 600 are in the left ventricle (similar to the positioning of shown in FIG. 6).

Figure 28:
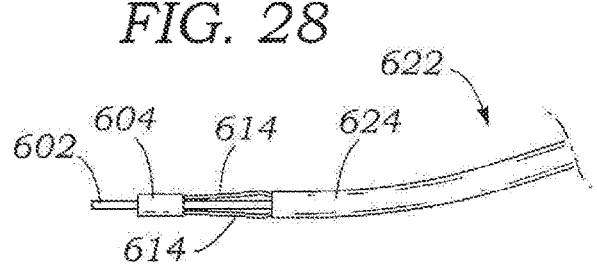
Figure 29:
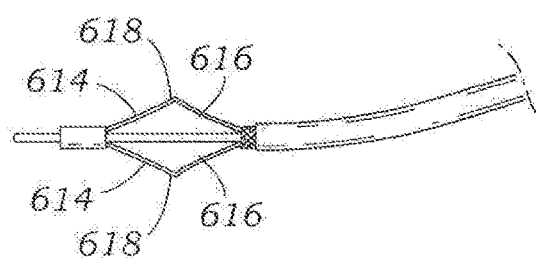
Figure 30:
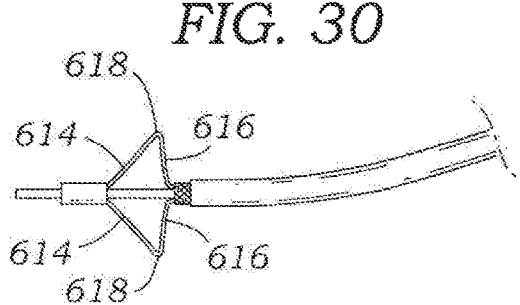
Figure 31:
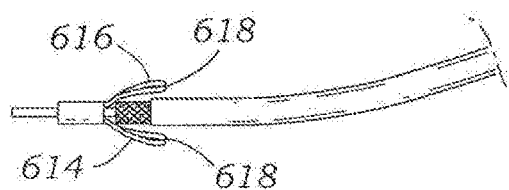

As shown in FIG. 28, the anchors 610 of the braided portion 606 of the device 600 can be exposed by advancing the inner shaft and the outer shaft 608 of the implant catheter 622 distally relative to the delivery sheath 624 and/or retracting the delivery sheath 624 relative to the inner shaft and the outer shaft 608, thus forcing the anchors 610 out of the sheath 624. Once exposed from the sheath 624, the joints 618 of the anchors 610 can expand radially away from the inner shaft 602, as shown in FIG. 29. The anchors 610 can be folded by retracting the inner shaft of the implant catheter 622 (which is connected to the inner shaft 602 of the implant 600) relative to the outer shaft 608 and the sheath 624, which in turn causes the inner shaft 602 to retract, causing the anchors 610 to bend at the joints and upper legs 616 to fold inwardly towards the inner shaft 602, as shown in FIGS. 30 and 31. In this configuration, the anchors 610 can be positioned behind the ventricular portions of the leaflets (e.g., desirably at the A2 and P2 positions).

Figure 32:
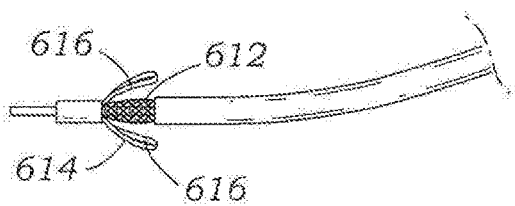
Figure 33:
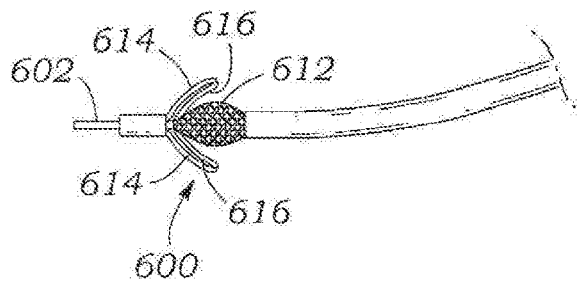

The body 612 of the braided portion 606 of the device 600 can be exposed by further retracting the delivery sheath 624 relative to the inner and outer shafts of the implant catheter (as shown in FIG. 32) and/or advancing the shafts distally relative to the sheath 624, which allows the body 612 to expand radially (as shown in FIG. 33) and thereby capture the leaflets between the upper legs 616 of the anchors 610 and the spacer body 612. The leaflets can then be secured between the upper legs 616 of the anchors 610 and the spacer body 612 of the braided portion by advancing the outer shaft 608 of the implant catheter 622 relative to the inner shaft 602 and the delivery sheath 624 of the implant catheter 622 such that the spacer body 612 moves axially toward distal end of the inner shaft 602 until it abuts the end cap 604, at which point further advancing the outer shaft compresses the end portions of the spacer body 612 between the end caps 604 and the outer shaft 608.

Figure 34:
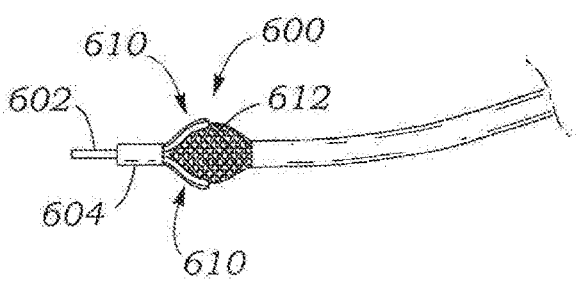

Compressing the ends of the spacer body 612 foreshortens the spacer body 612 axially and expands it radially, which forces the spacer body 612 radially outward against the leaflets, as shown in FIG. 34. Thus, the device 600 can be secured by clamping the leaflets between the upper legs 616 of the anchors 610 of the braided portion 606 and the spacer body 612 of the braided portion 606. Thereafter, the inner and outer shafts of the implant catheter 622 can be released from the device 600 and the delivery apparatus can be removed from the patient.

Figure 35:
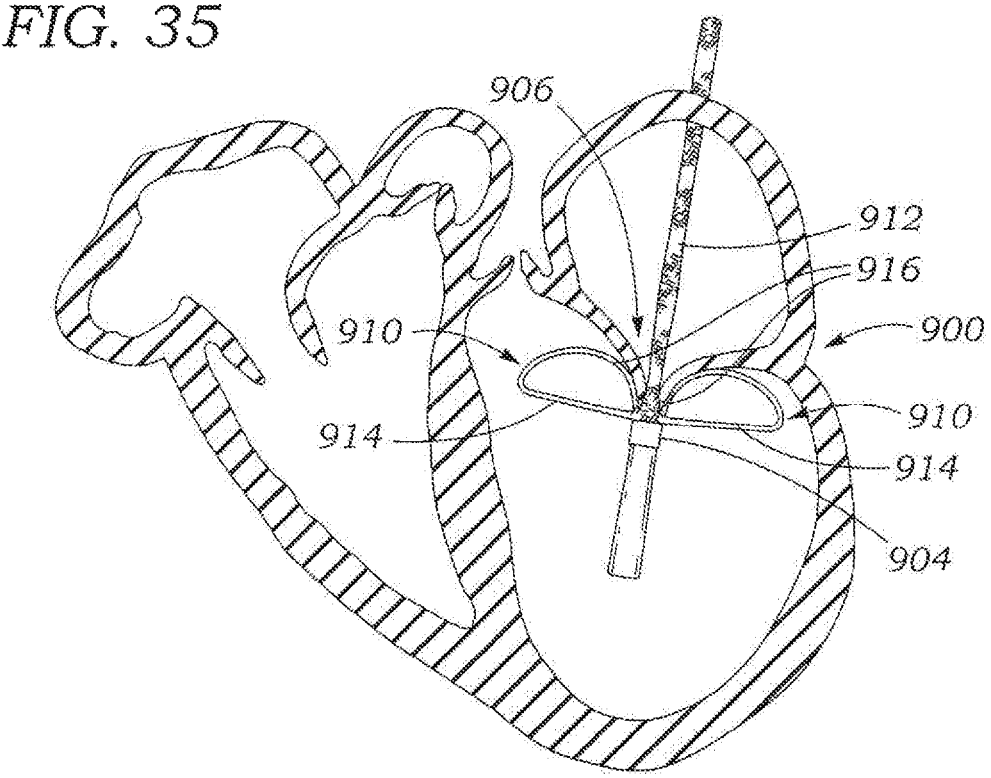
FIG. 35 shows another embodiment of an implantable prosthetic device being implanted within the native mitral valve.

FIG. 35 show an exemplary embodiment of an implantable prosthetic device 900 similar to device 600, including a braided portion 906, according to another embodiment. The braided portion 906 of the device 900 includes one or more anchors 910 (two are shown in the illustrated embodiment) and a spacer body 912. As shown, the anchors 910 of the braided portion 906 of the device 600 can be formed from a braided piece of material which is separate from the braided piece of material forming the spacer body 912. The anchors 910 each include a lower leg 914 and an upper leg 916. Each upper leg 916 can be inserted into and attached to an end cap 904 which is disposed on the distal end of an inner shaft (not shown) of the device 900. Each lower leg 914 can be connected to the other lower leg 914. For example, in some embodiments, the lower legs 914 of the anchors 910 can be formed from a single continuous piece of braided material, shown in FIG. 35 as the laterally extending section perpendicular to the spacer body 912. In some embodiments (where each anchor 910 is formed from a separate piece of braided material), the lower legs 914 can, for example, be connected by inserting the ends of the lower legs 914 into a coupler or sleeve which compressively secures the ends of the lower leg 914 within the coupler.

Figure 36:
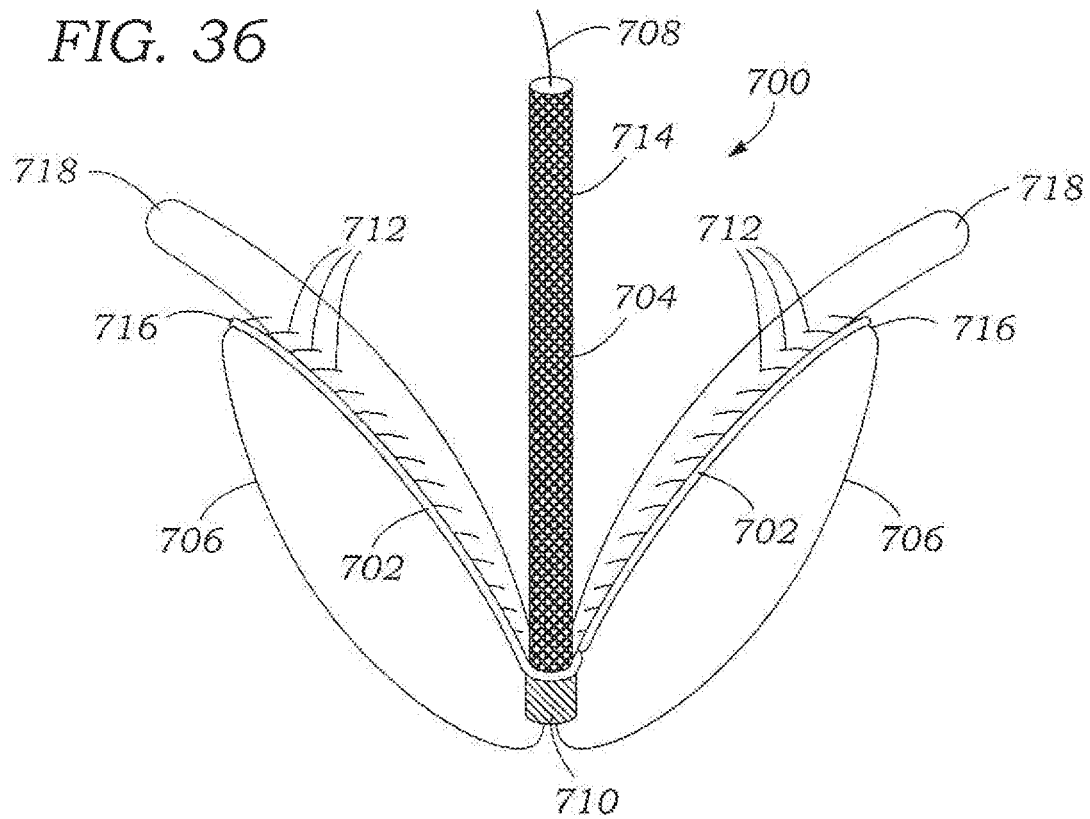
FIG. 36 shows another embodiment of an implantable prosthetic device being implanted within the native mitral valve.

FIG. 36 shows another exemplary embodiment of an implantable prosthetic device 700. The device 700 comprises one or more ventricular anchors 702 (two in the illustrated embodiment), a spacer body 704, one or more anchor actuation lines 706 (FIG. 36 shows two), and a pull wire 708. The actuation lines 706 and the pull wire 708 extend co-axially through the body 704.

The anchors 702 can comprise a plurality of leaflet retention elements 712. For example, FIG. 36 shows that the retention elements 712 can comprises outwardly extending projections or barbs that can press into and/or penetrate leaflet tissue to secure the anchors 702 to the leaflets. In another embodiment, the retention elements can comprise a textured surface formed in and/or applied to the anchors 702 of the device 700.

The spacer body 704 can comprise a collar 710 positioned toward the ventricular end of the body 704 of the device 700 and a braided portion 714. Although the braided portion has a generally cylindrical shape when in the expanded configuration shown in the illustrated embodiment, the braided portion can have various other shapes in other alternative embodiments. For example, the braided portion can expand to a generally spherical shape (similar to the body 504 in FIG. 20).

The braided portion 714 can be fixedly secured to the collar 710 such as by adhesive, welding, fasteners, etc. The anchors 702 can also be fixedly secured to the collar 710. In some embodiments, the anchors can be fixedly secured to the collar 710, for example, by welding, fasteners, or an adhesive. In alternative embodiments, the anchors 702 can be fixedly secured to the collar 710, for example, by forming the anchors 702 and the collar 710 from a single piece of material (e.g., laser cutting a metal tube).

The anchor actuation lines 706 can be wires or sutures formed from various materials such as nylon, polyester, PVDF, polypropylene, stainless steel, etc. Each line 706 comprises a first end 716 which is fixedly secured or coupled to a respective free end of an anchor 702, a second end (not shown) which is fixedly secured or coupled to the distal end of the pull wire, and an intermediate portion positioned between the first end 716 and the second end. In the illustrated embodiment, the lines 706, beginning at the first ends 716 and moving toward the second ends, each extend outwardly away from the free end of the anchors 702, downwardly toward the collar 710 of the body 704, co-axially through the collar 710, and co-axially into the braided portion 714 of the body 704, and are secured to the pull wire 708 within the braided portion 714 of the body 704.

The anchors 702 can be formed from a self-expandable material, such as Nitinol. The braided portion 714 of the body 704 can also be formed from a self-expandable material, such as braided Nitinol. When formed from a self-expandable material, the anchors 702 and the braided portion 714 of the body 704 can be radially compressed to a delivery configuration and can be retained in the delivery configuration by placing the device 700 in the sheath of a delivery apparatus.

When deployed from the sheath, the anchors 702 and the braided portion 714 can radially expand, creating gaps between the anchors 702 and the braided portion 714 of the body 704 wherein the native leaflets 718 of a heart valve can be placed, as shown in FIG. 36. The leaflets 718 can then be secured between the anchors 702 and the braided portion 714 by applying tension to the pull wire 708 and thereby the lines 706, causing the free end of the anchors 702 to bow or bend outwardly and the portion of the anchors 702 disposed between the free end and the fixed end of the anchors 702 (i.e., the middle portion) to buckle inwardly, which forces the retention elements into the leaflets 718. With the retention elements 712 inserted into the leaflets 718, the device 700 can maintain its position relative to the leaflets during diastole and systole.

FIGS. 37-47 show another exemplary embodiment of an implantable prosthetic device 800 and its components. In the illustrated embodiment, the device 800 comprises one or more ventricular anchors 802 (two in the illustrated embodiment), a spacer body 804, an interior shaft portion 806. The interior shaft portion 806 extends co-axially through the spacer body 804. The anchors 802 press radially inward toward the interior shaft 806 to create a clamping force between the anchors 802 and the spacer body 804, as further described below.

Figure 46:
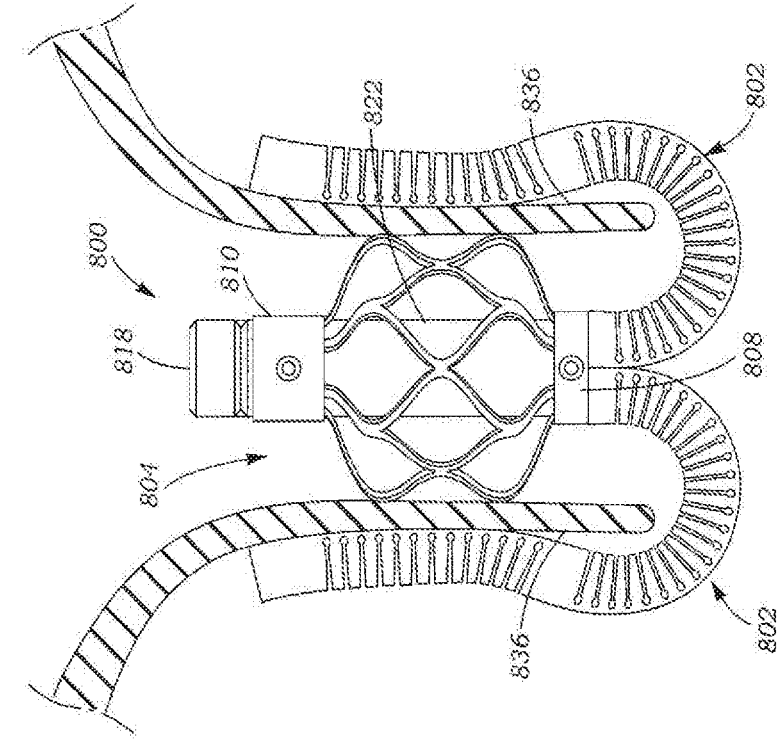

FIGS. 41-44 show the anchors 802 and the spacer body 804 of the device 800 in the expanded functional state. FIG. 45 shows the anchors 802 and the spacer body 804 of the device 800 in the crimped or compressed delivery state. FIG. 46 shows anchors 802 of the device 800 in the functional state.

Figure 37:
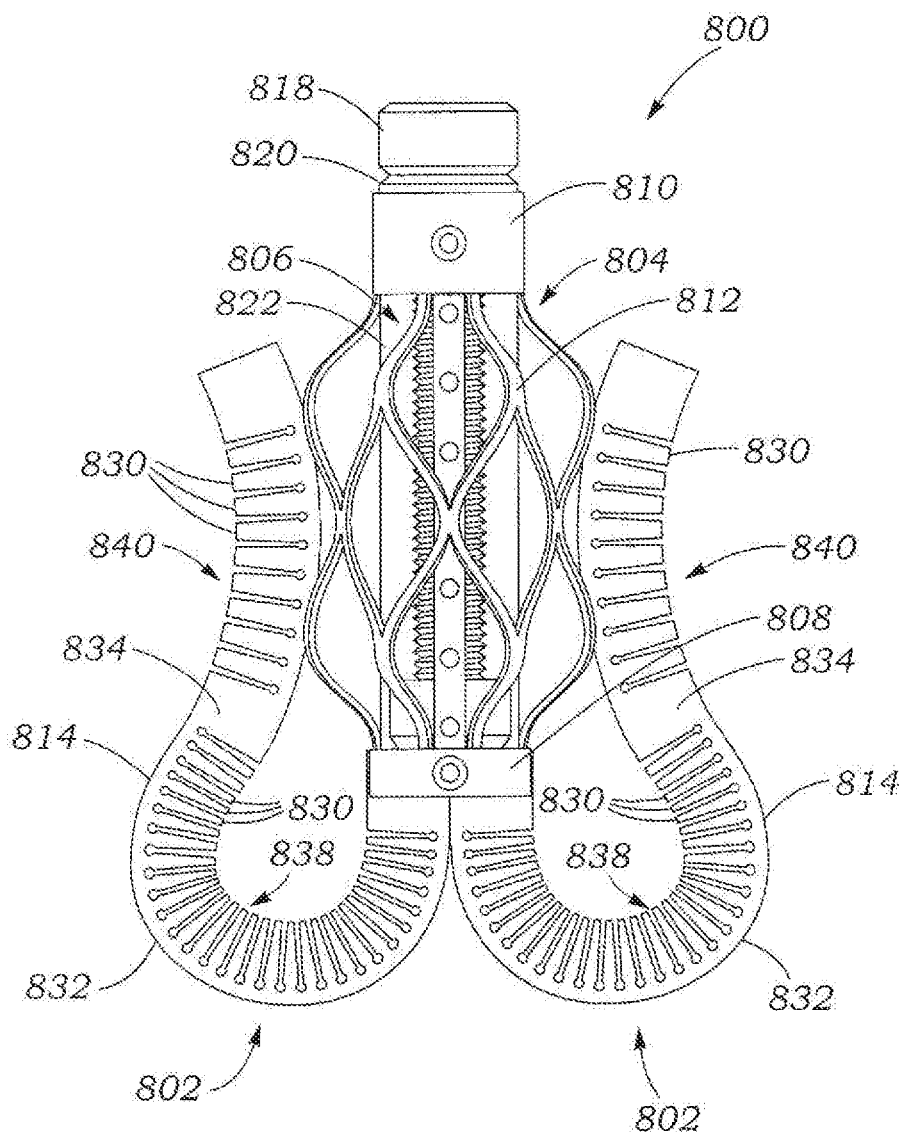

FIG. 37 shows that the spacer body 804 can comprise a metal frame comprising a distal, first annular collar 808 disposed around the shaft 806 and positioned towards the ventricular end of the spacer body 804 of the device 800, a proximal, second annular collar 810 disposed around the shaft 806 and positioned towards the atrial end of the spacer body 804 of the device 800, and a plurality of interconnected struts 812 extending between the first and second collars 808, 810. The struts 812 can, for example, be fixedly secured to the collars 808, 810 by forming the struts 812 and the collars 808, 810 from a single, unitary piece of material (e.g., laser cutting a metal tube). In other embodiments, the struts 812 can, for example, be fixedly secured to the collars 808, 810 by an adhesive, welding, fasteners, etc. Although not shown in FIGS. 37-47, the frame can be covered with a blood-impervious cover (e.g., fabric) or coated with a flexible sealant (e.g., ePTFE).

FIG. 37 also shows that the anchors 802 of device 800 can each comprise a flexible tube portion 814. The tubes 814 can be formed from alloy tubing such as, for example, Nitinol, stainless steel, cobalt chromium, etc. The proximal ends of the tubes 814 can be, for example, fixedly secured or coupled to the distal collar 808, such as by an adhesive, welding, fasteners, etc. The tubes 814 can also be configured to allow the tubes 814 to bend more easily in a desired direction and/or with a tighter bend radius without plastically deforming (e.g., kinking). For example, as shown, a portion of the circumference of the tubes 814 can be formed (e.g., by laser cutting) such that a section of the tubes comprises a plurality of axially spaced, circumferential ribs 830 on a first, cut side of the tubes and a solid portion or spine 832 on a second, non-cut side opposite to the cut side, relative to the circumference the tube. By cutting the tubes on one side, the tubes 814 can bend more easily in the direction of the side of the tube with the ribs 830, relative to the side with the spine 832.

The tubes 814 can also be cut asymmetrically with respect to the longitudinal axis of the tubes 814 such that the ribs 830 are oriented on different sides of the tubes 814 for different axial sections. For example, as shown, the tubes 814 each comprise a first cut section 838, located near the proximal ends of the tubes 814 (the ends fixedly secured to the distal collar 808), wherein the ribs 830 face outwardly (i.e., away from each other) when the tubes are extended or straightened in the crimped or delivery configuration (shown in FIG. 45) and a second cut section 840 located more distally relative to the first cut section 838, wherein the ribs 830 face inwardly (i.e., towards each other) when the tubes are extended or straightened in the crimped or delivery configuration. The first cut section 838 and the second cut section 840 can, for example, be separated by an un-cut transition section 834 (FIG. 37).

In some embodiments, the different axial sections can be form from a single piece of material. In other embodiments, the different axial sections can be formed from separate pieces of material fixedly secured or coupled together. Also, the ribs of the different axially sections can be different sizes to allow the respective axial sections to bend more or less tightly. For example, as shown, in the proximal sections 838, the ribs 830 of the tubes 814 can be relatively thinner (i.e., more of the tubing has been removed during the cutting process) than the ribs 830 of the second more distal sections 840, allowing the first sections 838 to have a smaller bend radius relative to the second sections 840. Thus, by cutting the tubes 814 and orienting the ribs 830, the manner and sequence that the tubes bend/buckle and extend/straighten can be controlled, as further described below.

Figure 38:
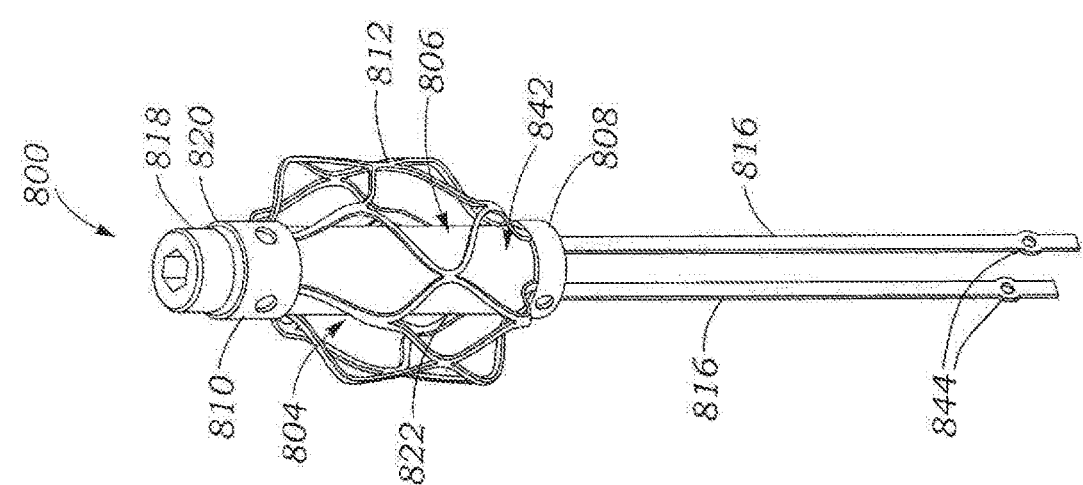

FIG. 38 shows the device 800 with the tubes 814 of the anchors 802 removed, thus exposing pull wires 816 (two are shown) of the anchors 802. The pull wires 816 can each extend co-axially within a respective tube 814 of an anchor 802 and can be fixedly secured to the shaft portion 806 at a first, proximal end 842 (FIG. 40) of the pull wires 816, and fixedly secured to the interior portion of the tubes 814 near the distal end of the tubes 814 at a second, distal end 844 of the pull wires 816, as further described below. The pull wires 816 can, for example, be used to move the anchors 802 from the crimped delivery state (shown in FIG. 45) to the expanded functional state (shown in FIG. 37) and/or secure native leaflets between the anchors 802 and the spacer body 804, as further described below.

Figure 40:
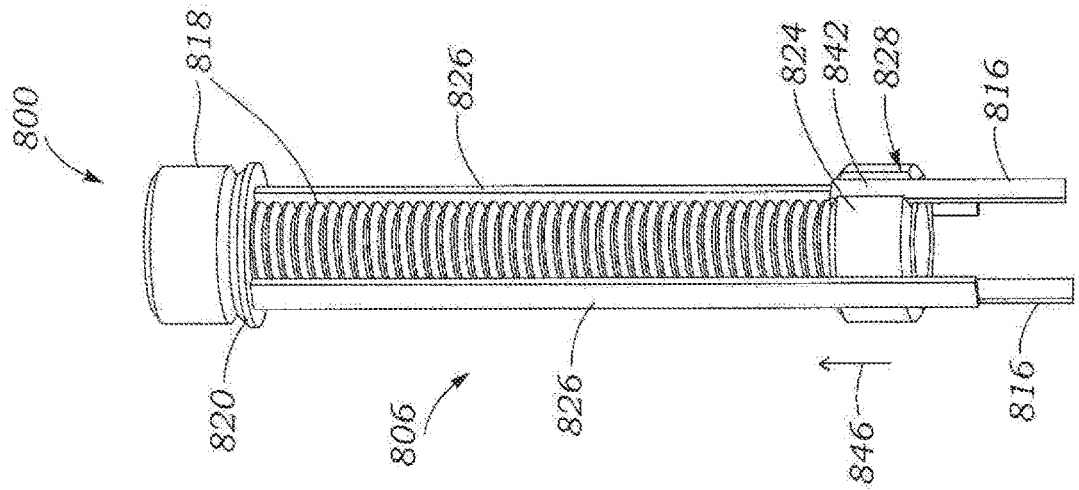
Figure 39:
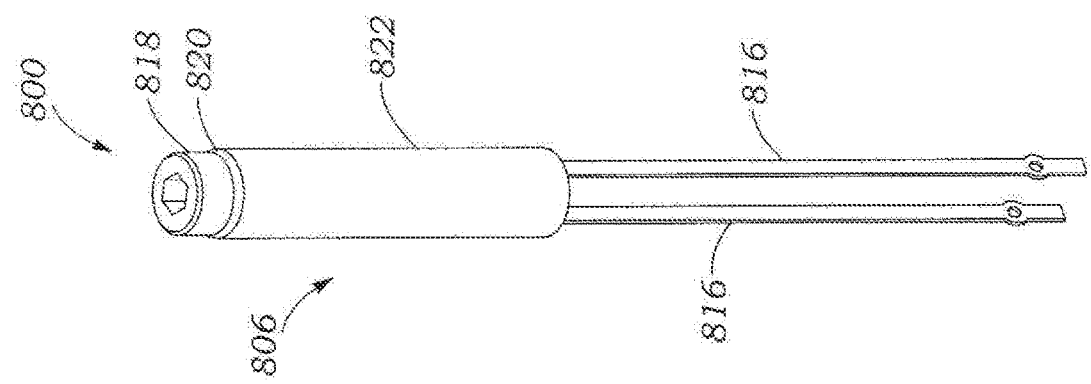

As best shown in FIGS. 39-40, the shaft assembly 806 of the device 800 in the illustrated configuration includes a threaded bolt 818, a washer 820, and a shaft or shim support sleeve 822. The threaded portion of the bolt 818 extends co-axially through the washer 820 and the sleeve 822 of the shaft 806. The bottom (distal) surface of the head portion of the bolt 818 abuts the top (proximal) surface of the washer 820. The bottom (distal) surface of the washer 820 abuts the proximal end of the sleeve 822 of the shaft assembly 806 and the proximal end of the proximal collar 810 of the spacer body 804. The sleeve 822 can be fixedly secured to the inner surfaces of the collars 808, 810 of the spacer body 804 at respective ends of the sleeve 822.

The shaft 806 assembly can also include a nut 824 and nut support rails 826 (two are shown), as best shown in FIG. 40. The nut 824 is disposed on the threaded portion of the bolt 818 and within the sleeve 822. The nut 824 can comprise internal threads, which correspond to the threaded bolt 818. The nut 818 can also comprise a plurality of axially extending external notches or grooves 828 through which the rails 826 and the pull wires 816 extend preventing the nut 818 from rotating relative to the bolt 818, thereby producing axial movement of the nut upon rotation of the bolt. The rails 826 can be fixedly secured to the sleeve 822, preventing the rails 826 and, thus, the nut 824 from rotating relative to the spacer body 804.

By rotating the bolt 818, the nut 824 can slide axially along the rails 826 and moves axially, either proximally or distally (depending on the direction of rotation), along the threaded portion of the bolt 818 without rotating. The proximal ends of the pull wires 816 of the anchors 802 can be fixedly secured to the nut 824. Thus, rotating the bolt 818 moves the nut 824 and thus the pull wires 816 proximally or distally, depending on the direction of rotation. Rotating the bolt 818 such that the wires 816 move proximally (in the direction of arrow 846) applies a compressive force to the tubes 814, causing the tubes 814 of the anchors 802 bend or buckle into the functional state from the straightened, delivery configuration.

As shown, the pull wires 816 can be sufficiently rigid such that the pull wires 816 can apply a pushing force. Thus, rotating the bolt 818 such that the pull wires 816 move distally applies a tensile force to the tubes 814, causing the tubes to extend and/or straighten to a delivery configuration (shown in FIG. 45). In an alternative embodiment, the tubes 814 can be formed from a shape memory material (e.g., Nitinol) which have been pre-formed in the straightened, delivery configuration. Thus, rotating the bolt 818 such that the pull wires 816 move distally removes the compressive force from the tubes 814, allowing the tubes 814 to straighten to the delivery configuration.

The device 800 can be delivered percutaneously to a native heart valve (e.g., the mitral valve with a delivery apparatus (not shown), for example, using the transseptal technique described for the prosthetic device 200 and the delivery apparatus 202 (shown in FIGS. 6-8). The device 800 and associated delivery apparatus can be advanced across the native mitral valve leaflets 836 until the anchors 802 of the device 800 are in the left ventricle (similar to the configuration shown in FIG. 6). The device 800 can be advanced from the delivery sheath (not shown, but similar to sheath 216) to expose the anchors 802.

In some embodiments, the anchors 802 can be self-expandable (e.g., formed from a shape-memory material, such as Nitinol) such that the anchors can transition from the delivery configuration (best shown in FIG. 45) to a leaflet capture configuration (best shown in FIG. 47) when deployed from the delivery sheath in a manner similar to device 300 (as shown in FIGS. 13 and 14). When formed from a self-expandable material, the shaft 806 and the pull wires 816 can be used to secure the leaflets, as further described below. In some embodiments, the anchors 802 can be plastically deformable (e.g., formed from stainless steel). When formed from a plastically deformable material, the anchors 802 can be expanded from the delivery configuration to the leaflet capture configuration by rotating the bolt 818 using a torque shaft (not shown, but similar to torque shaft 220), causing the anchors 802 to bend, as best shown in FIG. 46 and described in detail above.

Figure 47:
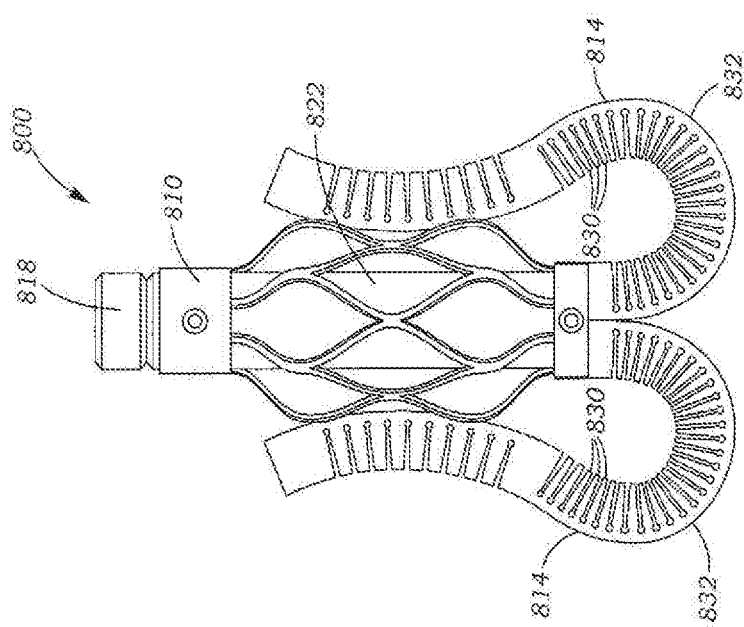

The spacer body 804 can then be deployed by further retracting the delivery sheath, allowing the spacer body to radially expand and capture the native leaflets 836 between the anchors 802 and the spacer body 804, as shown in FIG. 47. The leaflets 836 can then be tightly secured between the anchors 802 and the spacer body 804 by rotating the torque shaft and the bolt 818, causing the nut 824 and the wires 816 to move proximally along the threaded shaft portion 806. Movement of the wires is effective to cause the tubes 814 to bend and further urge the anchors 802 against the leaflets 836. Thus, the prosthetic device 800 can be secured to the leaflets 836 by clamping the leaflets between the anchors 802 and the spacer body 804, as shown in FIG. 47. Thereafter, the delivery device can be removed from the patient's body.

With the device 800 secured to both of the leaflets 836, it brings them closer together around the spacer body 804. By so doing, the device 800 decreases the overall area of the mitral valve orifice and divides the mitral valve orifice into two orifices during diastole. Thus, the area through which mitral regurgitation can occur is reduced, leaflet coaptation can be initiated at the location of the body 804, and the leaflets can fully coapt more easily, thereby preventing or minimizing mitral regurgitation.

FIGS. 48-52 show another exemplary embodiment of an implantable prosthetic device 1000, similar to device 800. In the illustrated embodiment, the device 1000 comprises one or more ventricular anchors 1002 (two in the illustrated embodiment), a spacer body 1004, an interior shaft assembly (not shown, similar to the shaft assembly 806 of the device 800). The interior shaft assembly extends co-axially through the body 1004. The anchors 1002 press radially inward toward the interior shaft to create a clamping force between the anchors 1002 and the spacer body 1004, as further described below.

As best shown in FIG. 49, the spacer body 1004 can comprise a metal frame comprising a distal, first annular collar 1008 disposed around the shaft assembly (not shown) and positioned towards the ventricular end of the spacer body 1004, a proximal, second annular collar 1010 disposed around the shaft assembly and positioned towards the atrial end of the spacer body 1004 of the device 1000, and a plurality of interconnected struts 1012 extending between the first and second collars 1008, 1010. In some embodiments, the struts 1012 can, for example, be fixedly secured to the collars 1008, 1010 by forming the struts 1012 and the collars 1008, 1010 from a single, unitary piece of material (e.g., laser cutting a metal tube). In other embodiments, the struts 1012 can, for example, be fixedly secured to the collars 1008, 1010 by an adhesive, welding, fasteners, etc. Although not shown in FIGS. 48-52, the spacer body 1004 can be covered with a blood-impervious cover (e.g., fabric) or coated with a flexible sealant (e.g., ePTFE).

As shown, the anchors 1002 of device 1000 can each comprise a flexible tube portion 1014. The tubes 1014 can be formed from alloy tubing such as, for example, Nitinol, stainless steel, cobalt chromium, etc. The proximal ends 1020 (FIG. 52) of the tubes 1014 can be, for example, fixedly secured or coupled to the distal collar 1008, such as by an adhesive, welding, fasteners, etc.

The tubes 1014 can also be configured to allow the tubes 1014 to bend more easily in a desired direction and/or with a tighter bend radius without plastically deforming (e.g., kinking). For example, as shown, a portion of the circumference of the tubes 1014 can be framed (such as by laser cutting) such that a section of the tubes comprises a plurality of ribs 1016 on a first, cut side of the tubes and a solid portion or spine 1018 on a second, non-cut side opposite to the cut side, relative to the circumference the tube. By cutting the tubes on one side, the tubes 1014 can bend more easily in the direction of the side of the tube with the ribs 1016, relative to the side with the spine 1018. The tubes 1014 can also be cut asymmetrically with respect to the longitudinal axis of the tubes 1014 such that the ribs 1016 are oriented on different sides of the tubes 1014 for different axial sections, as best shown in FIG. 52. Thus, by cutting the tubes 1014 and orienting the ribs 1016, the manner and sequence that the tubes 1014 bend/buckle and extend/straighten can be controlled.

Although not shown, the interior shaft assembly of device 1000 can be similar to shaft portion 806 of device 800, including comprising substantially the same components. Also, the anchors 1002 can comprise anchor pull wires (not shown, but similar to the wires 816), fixedly secured to a nut (not shown) of the shaft at a first, proximal end of the wires and fixedly secured to the distal ends of tubes 1014 at a second, distal end of the wires, similar to the wires 816. Thus, the device 1000 can function substantially similarly to the device 800. The anchors 1002 of device 1000 can, however, contact the native leaflets (not shown) laterally.

With respect to the device 1000, the term "lateral" means generally perpendicular to the longitudinal axis of the prosthetic device 1000 extending through the distal and proximal collars 1008, 1010. For example, FIG. 49 shows the anchors extending laterally across the spacer body 1004, with the longitudinal axis extending coaxially through the collars 1008, 1010. Thus, in this manner, each anchor 1002 can extend lateral across and in contact with the ventricular side of a respective native leaflet.

It should be noted that although the anchors 802, 1002 of the respective devices 800, 1000 can be simultaneously actuated (e.g., moved from the delivery configuration to the functional configuration and/or secured against native leaflets, etc.), as described above, in some embodiments each individual anchor can be separately actuated. For example, one of the anchors 802, 1002 can be moved from the delivery configuration to the functional configuration and can be secured to a native leaflet, and then, subsequently, another anchor 802, 1002 can be moved from the delivery configuration to the functional configuration and can be secured to a native leaflet.

In order to allow the anchors to be separately actuated, the shaft assemblies (similar to shaft assembly 806) can, for example, include multiple bolts and nuts (similar to bolt 818 and nut 824), with each bolt and nut corresponding to a separate pull wire of a respective anchor. By having separate bolts and nuts for each pull wire, each anchor can be actuated by rotating the bolt corresponding to the anchor, causing the nut to move axially along the threaded portion of the bolt and the anchor to either fold/bend or to extend/straighten depending on the direction of rotation of the bolt.

FIGS. 53-58 show another exemplary embodiment of an implantable prosthetic device 1100. In the illustrated embodiment, the device 1100 comprises a ventricular portion 1102, a spacer body 1104, an inner shaft 1106, and an outer shaft 1108. The inner shaft 1106 extends co-axially through the outer shaft 1108, and the inner and outer shafts 1106, 1108 extend co-axially through the spacer body 1104. The outer shaft 1108 can be axially moveable (proximally and distally) relative to the inner shaft 1106 and the spacer body 1104. The distal direction is indicated by arrow 1120 (FIG. 53), the proximally direction being generally opposite the distal direction. The spacer body 1104 can be axially moveable (proximally and distally) relative to the inner shaft 1106 and the outer shaft 1108.

The ventricular portion 1102 includes one or more outer anchor members 1110 (two in the illustrated embodiment), one or more inner anchor members 1112 (two in the illustrated embodiment), one or more cross-members 1114 (two in the illustrated embodiment). The outer anchors 1110 can be pivotably connected (e.g., a pin, fastener, ball joint, etc.) to the distal end of the inner shaft 1106 at first, distal ends of the outer anchors 1110, forming a first pivotable joint 1116. The outer anchors 1110 extend from the first joint 1116 to second, proximal ends of the outer anchors 1110. The inner anchors 1112 can be pivotably connected to respective outer anchors 1110 at intermediate portions of the inner anchors 1112, forming second pivotable joints 1118. The cross-members 1114 can be pivotably connected to the distal end of the outer shaft 1108 at first, inner ends of the cross-members 1114, forming a third pivotable joint 1122. The cross-members 1114 can be pivotably connected to respective distal ends of the inner anchors 1112 at second ends (opposite to the first ends) of the cross-members 1114, forming fourth pivotable joints 1124.

Figure 53:
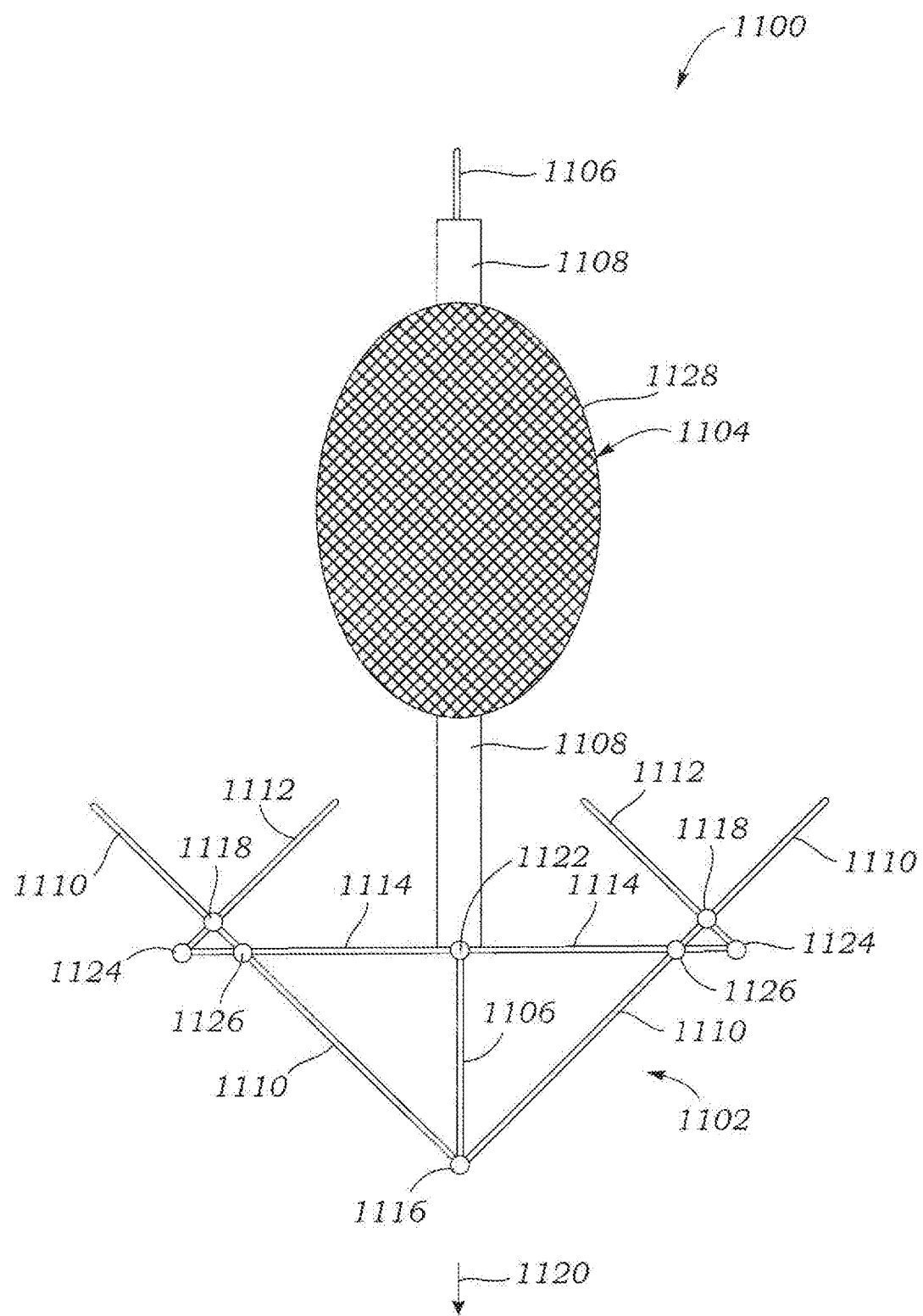
FIG. 53 shows another embodiment of an implantable prosthetic device.

The cross-members 1114 can also be slidably connected to respective outer anchors 1110 with connecting elements 1126. As best shown in FIG. 53, the connecting elements 1126 can be disposed on respective outer anchors 1110 between the pivotable joints 1116 and 1118 and disposed on cross-members 1114 between pivotable joint 1122 and pivotable joints 1124. The connecting elements 1126 can be, for example, slots formed in the outer anchors 1110 through which the cross-members 1114 extend.

The spacer body 1104 can comprise an annular metal frame (not shown, but similar to frame 28) covered with a blood-impervious fabric 1128. The frame can comprise a mesh-like structure comprising a plurality of interconnected metal struts or can comprise a metal braid. The frame can be formed from a self-expandable material, such as Nitinol. In other embodiments, the frame can be formed from a plastically expandable material, such as stainless steel or a cobalt chromium alloy.

Due to the adjustable nature of the ventricular portion 1102 and the flexible nature of the spacer body 1104, the device 1100 can be radially compressed to a delivery configuration (FIG. 54) and can be retained in the delivery configuration by placing the device in the sheath of a delivery apparatus.

As shown in FIGS. 54-58, the device 1100 can be delivered percutaneously to a native heart valve (e.g., the mitral valve) with a delivery apparatus (not shown), for example, using the transseptal technique described for the prosthetic device 200 and the delivery apparatus 202 (shown in FIGS. 6-8). Although not shown, the delivery apparatus can comprise a sheath (similar to sheath 216) into which the prosthetic device 1100 can be loaded, inner and intermediate shafts releasably connected to respective inner and outer shafts 1106, 1108 of the device 1100, and an outer shaft releasably connected to the spacer body 1104 of the device 1100.

The device 1100 and the delivery apparatus can be advanced across the native mitral valve leaflets 1130 until the ventricular portion 1102 of the device 1100 is in the left ventricle (as shown in FIG. 55 and similar to the configuration shown in FIG. 6). The ventricular portion 1102 can be exposed from the delivery sheath by distally advancing the inner shaft of the delivery apparatus and thus the inner shaft 1106 of the device 1100 relative to the sheath of the delivery apparatus and/or by retracting the delivery sheath relative to the inner shafts.

The anchors 1102 can be expanded from the delivery configuration to the leaflet capture configuration by distally advancing the outer shaft of the delivery apparatus and thus the outer shaft 1108 relative to the inner shaft 1106, thus moving the joint 1122 distally (i.e., towards joint 1116) along the inner shaft 1106 such that the cross-members 1114 extend laterally, and perpendicular to the inner shaft 1106 (as shown in FIG. 55). The cross-members 1114 force the outer anchors 1110 to expand radially relative to the inner shaft 1106 and the inner anchors 1112 to expand or open relative to the outer anchors 1110, as shown in FIG. 55. With the anchors 1110, 1112 expanded and open, the leaflets 1130 (e.g., desirably at the A2 and P2 positions) can be positioned within the anchors 1110, 1112 by retracting the inner shaft 1106 proximally, as shown in FIG. 56.

The leaflets 1130 can then be secured between the anchors 1110, 1112 by further advancing the outer shaft 1108 distally relative to the inner shaft 1106, causing the joint 1122 to further move distally along the inner shaft 1106 such that the joint 1122 is distal to the joints 1124, 1126. Movement of the outer shaft 1108 and the cross-members 1114 is effective to move the distal ends of the inner anchors 1112 inwardly towards the inner shaft 1106, causing the inner anchors 1112 to pivot about joints 1118, forcing the proximal ends of the inner anchors 1112 towards the proximal ends of the outer anchors 1110, as shown in FIG. 57.

FIG. 57 also shows that the spacer body 1104 can then be deployed by retracting the delivery sheath. When formed from a self-expandable material, the frame can self-expand to its functional size (FIGS. 57-58). When formed from a plastically expandable material, the prosthetic device can be crimped onto a delivery apparatus and radially expanded to its functional size by an inflatable balloon or an equivalent expansion mechanism. The spacer body 1104 can then be positioned by advancing the outer shaft of the delivery apparatus and thus the spacer body 1104 relative to the inner and outer shafts 1106, 1108 of the device 1100, as shown in FIG. 58. Although as shown, the spacer body 1104 is only partially expanded, the spacer body 1104 can be further expanded such that the leaflets contact the spacer body 1104. The shafts of the delivery apparatus can then be released from the device 1100 and retracted into the sheath of the delivery apparatus. Thereafter, the delivery apparatus can be removed from the patient's body.

In some embodiments, as shown, the cross-members 1114 of the device 1100 can each be connected to the same outer shaft 1108, thus allowing both anchors to be simultaneously actuated. This configuration, for example, provides a device that is simple to use because there are relatively few steps for physician to perform to implant the device. This can, for example, help to reduce the complexity and/or the time needed to perform the placement procedure.

In some embodiments, the cross-members 1114 of the device 1100 can each be connected to a separate outer shaft, thus allowing the anchors to be individually actuated. This configuration can, for example, allow a physician to capture the native leaflet more easily because the physician can capture one side at a time. This can, for example, be helpful due to the dynamic nature of the leaflets during the diastolic and systolic cycles of a heart. Also, in some embodiments, the spacer body 1104 can be fixed to the outer shaft 1108, allowing the spacer body 1104 and the ventricular portion 1102 to be positioned simultaneously, which can, for example, advantageously reduce the time needed to perform the placement procedure.

Figure 59:
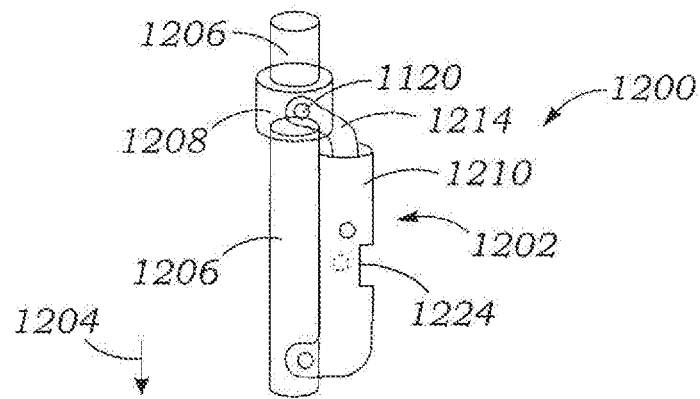
FIGS. 59-61 show various views of another embodiment of an implantable prosthetic device in different stages of deployment.
Figure 60:
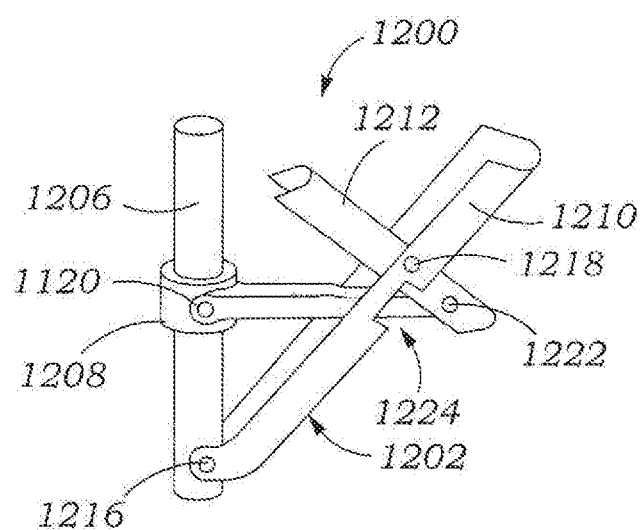
Figure 61:
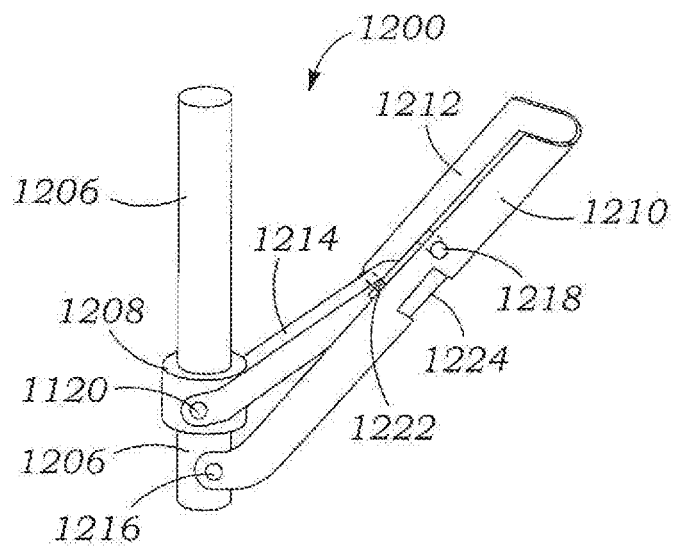

FIGS. 59-61 show another exemplary embodiment of an implantable prosthetic device 1200, similar to device 1100. In the illustrated embodiment, the device 1200 comprises at least one anchor 1202 (one is shown for purposes of illustration but multiple anchors 1202 could be included), a spacer body (not shown, but similar to spacer body 1104), a shaft 1206, and sleeve 1208 coaxially and slidably disposed on the shaft 1206. The shaft 1206 extends co-axially through the spacer body and the sleeve 1208. The spacer body is located on the shaft 1206, proximal to the sleeve 1208.

The sleeve 1208 can be axially moveable (proximally and distally) relative to the shaft 1206. The distal direction is indicated by arrow 1204 in FIG. 59, and the proximal direction is opposite the distal direction. The spacer body can be axially moveable (proximally and distally) relative to the shaft 1206. In some embodiments, the spacer body can also be axially moveable relative to the sleeve 1208, allowing the spacer body to be deployed and/or positioned separately from the anchor 1202. In some embodiments, the spacer body can be fixed or connected to the sleeve 1208, allowing the spacer body to be deployed and/or positioned simultaneously with the anchor 1202.

As best shown in FIG. 60, the anchor 1202 can be a truss-like structure comprising an outer member 1210, an inner member 1212, and a cross-member 1214. The outer member 1210 can be pivotably connected (e.g., a pin, fastener, etc.) to the distal end of the shaft 1206 at a first, distal end of the outer member 1210, forming a first pivotable joint 1216. The outer member 1210 extends from the first joint 1216 to a second, proximal end of the outer member 1210. The inner member 1212 can be pivotably connected to the outer member 1210 towards the distal end of the outer member 1210 at an intermediate portion of the inner member 1212, forming a second pivotable joint 1218. The cross-member 1214 can be pivotably connected to the sleeve 1208 at a first end of the cross-member 1214, forming a third pivotable joint 1220. The cross-member 1214 can also be pivotably connected to the distal end of the inner members 1212 at a second end (opposite to the first end) of the cross-member 1214, forming a fourth pivotable joint 1222. The outer member 1210 can also comprise an opening 1224, allowing the inner member 1212 and the cross-member 1214 to extend through the outer member 1210 when the device in in the leaflet capture configuration, as shown in FIG. 60.

Although not shown, the spacer body can comprise an annular metal frame (similar to frame 28) covered with a blood-impervious fabric (similar to fabric 1128). The frame can comprise a mesh-like structure comprising a plurality of interconnected metal struts or can comprise a metal braid. The frame can be formed from a self-expandable material, such as Nitinol. In other embodiments, the frame can be formed from a plastically expandable material, such as stainless steel or a cobalt chromium alloy.

Due to the adjustable nature of the anchor 1202 and the flexible nature of the spacer body, the device 1200 can be radially compressed to a delivery configuration (FIG. 59). As shown, the cross-member 1214 can be configured to nest within inner member 1214, and the inner member can be configured to nest within the outer member 1210, thereby reducing the profile of the device 1200 in the delivery configuration.

Although not shown, the device 1200 can be delivered percutaneously to a native heart valve (e.g., the mitral valve) with a delivery apparatus, for example, using the transseptal technique described for device 1100 (shown in FIGS. 54-58). FIG. 59 shows the device in the delivery configuration (similar to device 1100 in FIG. 54). FIG. 60 shows the device 1200 in the leaflet-capture configuration (similar to device 1100 in FIGS. 55-56). FIG. 61 shows the device 1200 in the functional or leaflet-secured configuration (similar to device 1100 in FIGS. 57-58).

Delivery Systems and Devices

Delivery systems and/or devices used to percutaneously deliver prosthetic implant devices (e.g., prosthetic spacer devices) can comprise introducer sheaths, one or more catheters (e.g., outer, guide, and/or implant catheters), and other devices. Generally, an introducer sheath can be inserted into a patient's body which provides an access point for other devices (e.g., catheters) to be introduced into the patient's body. For example, during a transseptal procedure, an introducer sheath can be inserted into a patient's right femoral vein through which an outer catheter can be inserted. The outer catheter can be advanced through the femoral vein, up the vena cava, and into the right atrium. The septum is then punctured with the outer catheter such that the outer catheter extends into the left atrium. The outer catheter can then be parked at the septal opening.

A middle or guide catheter can be inserted through the outer catheter to achieve the desired positioning for the respective procedure. For example, the guide catheter can be used to achieve the positioning with respect to the mitral valve. In particular embodiments, the guide catheter can also serve as the implant catheter configured to advance a prosthetic device through the patient's vasculature and deploy the prosthetic device at the desired implantation location. For example, the distal end portion of the guide catheter can comprise a delivery sheath configured to retain a prosthetic device in a compressed delivery state while advanced through the patient's body. In alternative embodiments, an inner or implant catheter can be inserted through the guide catheter to deploy, secure, and release a prosthetic implant device.

Some embodiments of the delivery systems disclosed herein allow the implant catheter to be either pre-loaded (i.e., inserted through the guide catheter prior to the guide catheter being advanced the outer catheter), or loaded during the procedure (i.e., inserted through guide catheter after the guide catheter is advanced into the left side of a patient's heart). Some embodiments of the delivery systems disclosed herein comprise a middle or guide catheter with a flexible, steerable distal portion and a control member on or adjacent the handle which can be used to bend, flex, and/or orient the distal portion. Some of the disclosed delivery systems comprise various locking, rotation and/or anti-rotation, and or coupling features.

The delivery systems disclosed herein can, for example, significantly improve a physician's ability to desirably orient and secure the catheters used, for example, in a transseptal procedure used to implant a prosthetic implant device. These systems can also, for example, significantly improve the safety, duration, and effectiveness of a prosthetic implant placement procedure.

Figure 62:
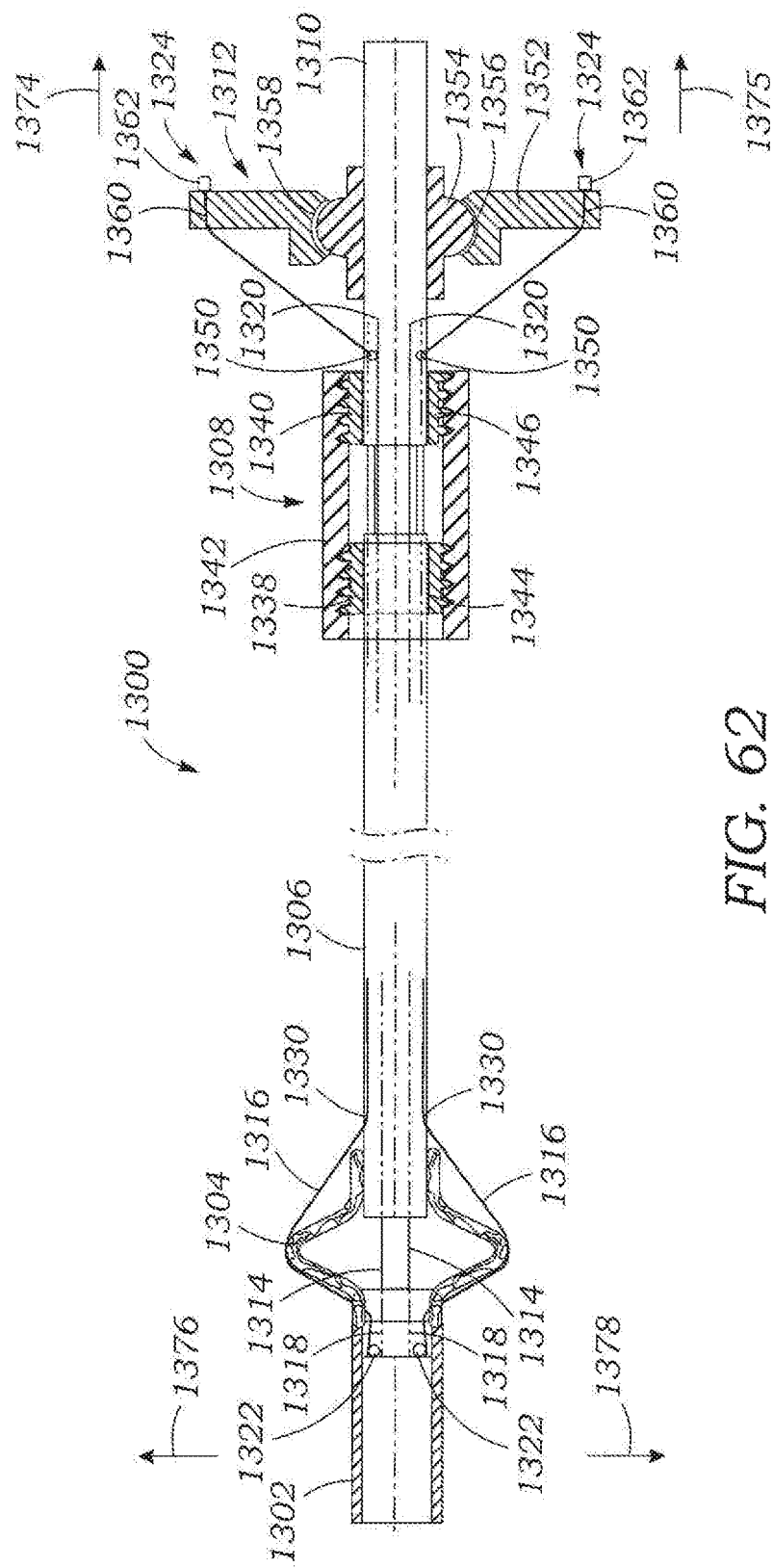
FIG. 62 is a side of a steerable delivery device for an implantable prosthetic device, according to one embodiment.

FIG. 62 shows an exemplary steerable, flexible prosthetic implant delivery device 1300, according to one embodiment. In the illustrated embodiment, the delivery device 1300 generally comprises an implant cover or sheath 1302, a flexible, radially expandable basket portion 1304, an intermediate shaft 1306, a basket expander mechanism 1308, a proximal shaft 1310, a steering control member 1312, a plurality of basket expander wires 1314 (four in the illustrated embodiment, but only two shown in FIG. 62), and a plurality of steering control wires 1316 (four in the illustrated embodiment, but only two shown in FIG. 62).

The basket portion 1304 of the delivery device 1300 can be disposed between the sheath 1302 and the intermediate shaft 1306. The basket portion 1304 can be fixedly secured or coupled (e.g., with an adhesive, fasteners, etc.) to the sheath 1302 at a first, distal end of the basket portion 1304 and fixedly secured or coupled to the intermediate shaft 1306 at a second, proximal end of the basket portion 1304. The expander mechanism 1308 can be disposed between the intermediate shaft 1306 and the proximal shaft 1310. The expander mechanism 1308 can be connected to the intermediate shaft 1306 at a first, distal end of the expander mechanism 1308 and to the proximal shaft 1310 at a second, proximal end of the expander mechanism 1308, as further described below.

The steering control member 1312 can be proximally disposed on the proximal shaft 1310, relative to the expander mechanism 1308. The basket expander wires 1314 can extend co-axially through the sheath 1302, the basket portion 1304, the intermediate shaft 1306, the basket expander mechanism 1308, and the proximal shaft 1310. The expander wires 1314 can be fixedly secured (e.g., with an adhesive) to the sheath 1302 at first, distal ends 1318 of the respective expander wires 1314, and to the proximal shaft 1306 at second, proximal ends 1320 of the respective expander wires 1314.

The control wires 1316 can extend co-axially through the sheath 1302, over the basket portion 1304, and through the intermediate shaft 1306, the expander mechanism 1308, and the proximal shaft 1310. The control wires 1316 can be fixedly secured to the sheath 1302 at first, distal ends 1322 of the respective control wires 1316 and to the control member 1312 at second, proximal ends 1324 of the respective control wires 1316.

Figure 67:
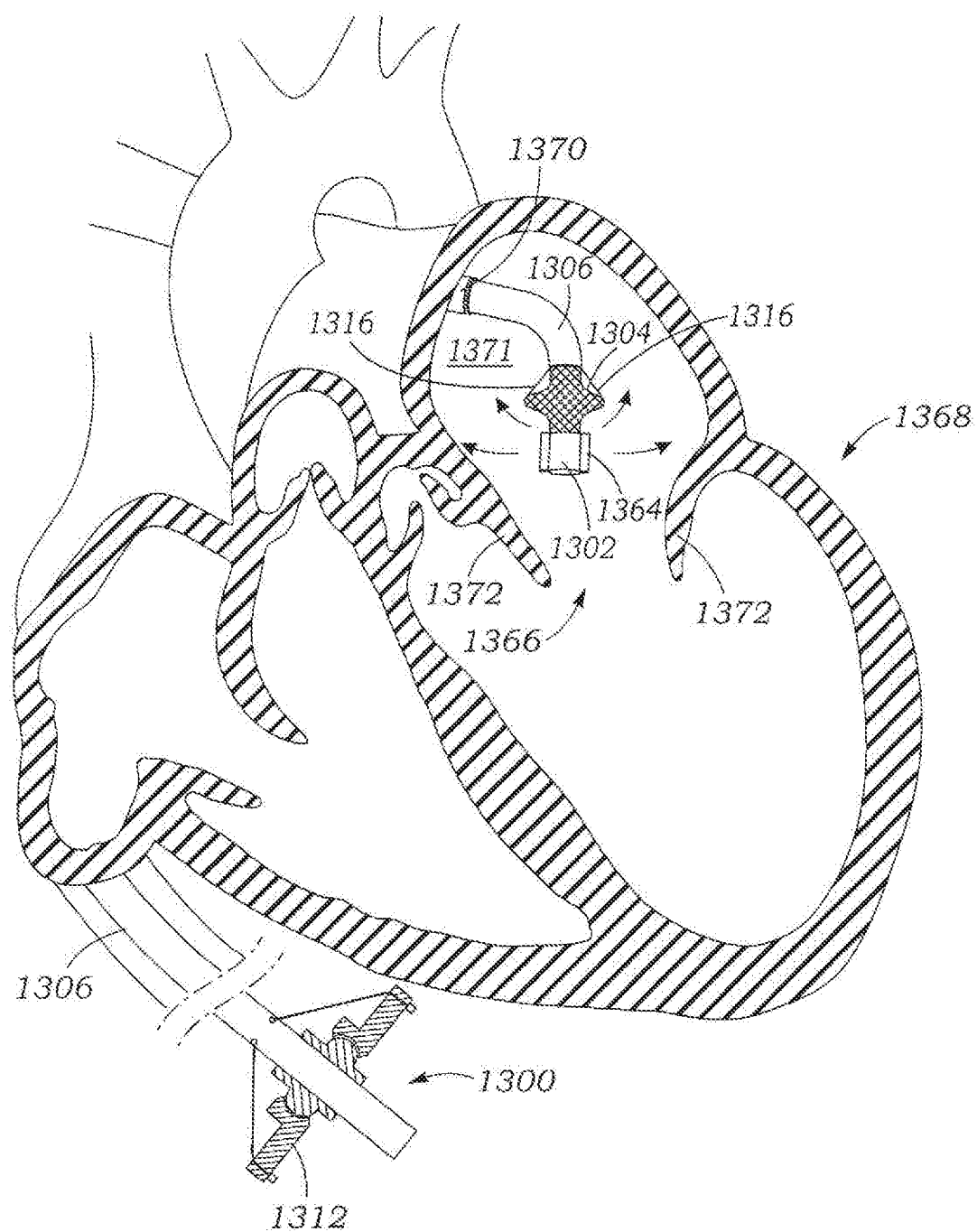
FIG. 67 shows the delivery of a prosthetic device to the native mitral valve using the delivery device of FIG. 62.

The sheath 1302 of the delivery device 1300 can be configured to receive various prosthetic implant devices and/or retain a prosthetic implant device in a delivery configuration. For example, the sheath 1302 can receive a prosthetic spacer device (e.g., the prosthetic spacers described herein) and retain the prosthetic device in a delivery configuration (as shown in FIG. 67). The sheath 1302 can also, for example, receive a prosthetic heart valve, stent, etc.

The basket 1304 of the delivery device 1300 can be expandable such that the basket 1304 can be placed in a non-expanded delivery configuration (best shown in FIG. 63b), allowing the device 1300 to have a relatively small profile when space is limited (e.g., when passing through another catheter or a vessel). When the space is not as limited (e.g. when advanced out of another catheter into the left atrium or another chamber of a heart), the basket 1304 can be radially expanded to a functional configuration (best shown in FIG. 64). The basket 1304 imparts flexibility to the distal end portion of the device thereby providing a physician with a greater range of motion and steerability at the distal end of the device 1300 and thus greater control of a prosthetic implant device during an implant placement procedure. In particular embodiments, the basket 1304 comprises a mesh or braided construction, such as a polymer braid (e.g. nylon) or a metal braid (e.g., Nitinol or stainless steel).

Figures 65A, 65B:
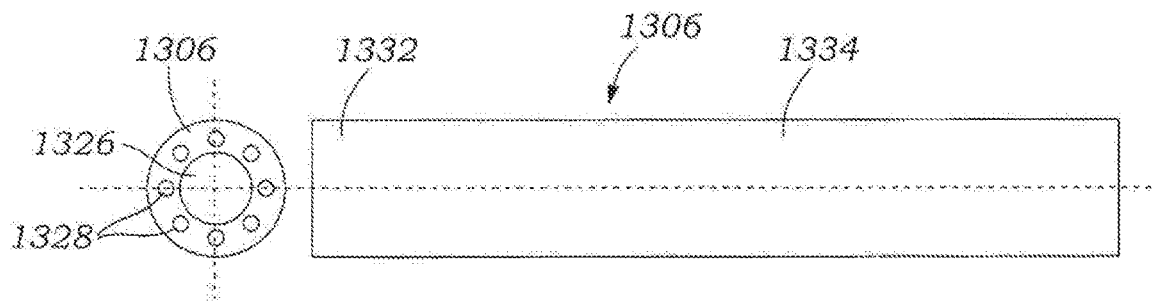
FIGS. 65*a* and 65*b* are end and side views, respectively, of the intermediate shaft of the delivery device of FIG. 62.

As best shown in FIG. 65A, the intermediate shaft 1306 of the delivery device 1300 can comprise a centrally disposed (relative to the longitudinal axis of the device) implant or working lumen 1326 and a plurality of wire lumens 1328 (eight in the illustrated embodiment) disposed radially outward from and distributed annularly around the implant lumen 1326 within the sidewall of the shaft. The wire lumens 1316 can be angularly spaced from each other by approximately 45 degrees. The respective lumens 1326, 1328 can extend axially through the intermediate shaft 1306.

The implant lumen 1326 can, for example, allow a device implant catheter (not shown, but similar to implant catheter 214) to be inserted through the implant lumen 1326. The wires 1314, 1316 can each extend through a respective wire lumen 1328. The four expander wires 1314 can occupy four of the wire lumens 1328 in an every-other lumen pattern, such that the expander wires 1314 are spaced apart from each other approximately 90 degrees. The four control wires 1316 can occupy the four remaining unoccupied lumens 1328 in an every-other lumen pattern, such that the control wires 1316 are spaced apart from each other approximately 90 degrees As shown in FIG. 62, the intermediate shaft 1306 can also comprise a plurality of radially extending side openings or ports 1330 (four in the illustrated embodiment, but only two shown in FIG. 62) located toward the distal end of the intermediate shaft 1306 but proximal to the basket 1304. The ports 1330 can be distributed circumferentially around the intermediate shaft 1306 (e.g., spaced apart from each other by 90 degrees), and configured to correspond with the wire lumens 1328 that are occupied by the control wires 1316, thereby allowing the control wires 1316 to enter respective wire lumens 1328 via respective side openings 1330. The intermediate shaft 1306 can be formed from a biocompatible polymer such as polyether block amide (e.g., Pebax®).

The intermediate shaft 1306 can include different axial sections that vary in hardness and/or rigidity. For example, as shown in FIG. 65b, the intermediate shaft can include a first, distal section 1332 and a second, proximal section 1334. The distal section 1332 of the intermediate shaft 1306 can, for example, comprise a softer material relative to the material of the proximal section 1334 of the intermediate shaft 1306. In some embodiments, for example, the sections 1332, 1334 of the intermediate shaft 1306 can comprise Pebax® with Shore D hardness values of 55 and 72, respectively. An intermediate shaft with a softer distal end can, for example, allow the distal end of the intermediate shaft 1306 to bend and/or flex more easily without kinking or otherwise plastically deforming.

The basket expander mechanism 1308 of the delivery device 1300 can comprise a distal nut 1338, a proximal nut 1340, and an outer nut or sleeve 1342, as shown in FIG. 62. The distal nut 1338 can be fixedly secured to the proximal end of the intermediate shaft 1306 and comprise external threads oriented in a first direction. The proximal nut 1340 can be fixedly secured to the distal end of the proximal shaft 1310 and comprise external threads oriented in a second direction, the second direction being opposite to the first direction of the threads of the distal nut 1338. The outer nut 1342 can comprise first internal threads 1344 along the distal end portion of the outer nut 1342 corresponding to and engaging the threads of the distal nut 1338 and second, proximal internal threads 1346 along the proximal end portion of the outer nut 1342 corresponding to and engaging the threads of the proximal nut 1340.

In use, rotation of the outer nut 1342 relative to the distal nut 1338 and the proximal nut 1340 in a first direction causes the distal and the proximal nuts 1338, 1340 and thus the intermediate shaft 1306 and the proximal shaft 1310 to move toward each other, and rotation of the rotation of the outer nut 1342 relative to the distal nut 1338 and the proximal nut 1340 in a second direction (opposite the first direction) causes the distal and the proximal nuts 1338, 1340 and thus the intermediate shaft 1306 and the proximal shaft 1310 to move away from each other, similar to a turnbuckle.

Rotation of the outer nut 1342 relative to the distal nut 1338 and the proximal nut 1340 in the first direction, causing the intermediate shaft 1306 to move towards the proximal shaft 1310 in the proximal direction, also moves the intermediate shaft 1306 away from the sheath 1302 in the proximal direction. And, rotation of the outer nut 1342 relative to the distal nut 1338 and the proximal nut 1340 in the second direction, causing the intermediate shaft 1306 to move away from the proximal shaft 1310 in the distal direction, moves the intermediate shaft 1306 towards the sheath 1302 in the distal direction.

Figures 63A, 63B:
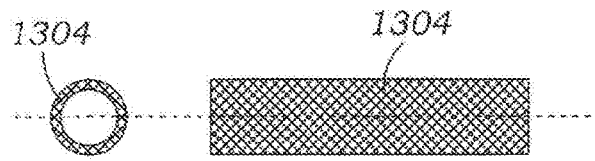
FIGS. 63*a* and 63*b* are end and side views, respectively, of an expandable basket portion of the delivery device of FIG. 62.
Figure 64:
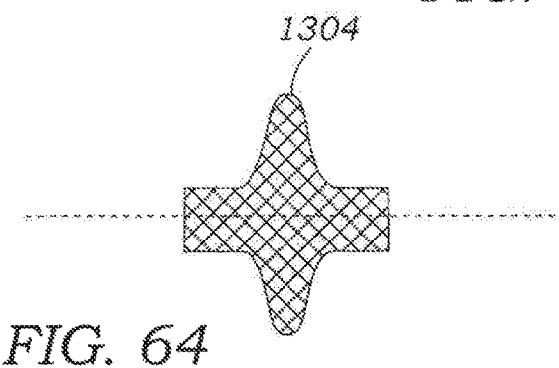
FIG. 64 is a side view of the basket portion of FIGS. 63*a* and 63*b* shown in an expanded configuration.

Due to the flexible nature of the basket 1304, rotation of the outer nut 1342 relative to the distal nut 1338 and the proximal nut 1340 in the first direction (i.e., moving the intermediate shaft 1306 proximally away from the sheath 1302) causes the basket 1304 to axially elongate and radially compress to the delivery configuration (shown in FIG. 63b). Rotation of the outer nut 1342 relative to the distal nut 1338 and the proximal nut 1340 in the second direction (i.e., moving the intermediate shaft 1306 distally towards the sheath 1302) causes the basket to axially foreshorten and radially expand to the functional configuration (shown in FIGS. 62, 64, 67).

The proximal shaft 1310 of the delivery device 1300 can have a construction that is substantially similar to that of the intermediate shaft 1306, including a centrally disposed (relative to the longitudinal axis) implant lumen 1348 (shown in FIG. 66) and a plurality of wire lumens (not shown, but similar to wire lumens 1328) (eight in the illustrated embodiment) disposed radially outward from and distributed circumferentially around the implant lumen 1348 within the side wall of the shaft 1310. The respective implant and wire lumens can extend co-axially through the proximal shaft 1310. The respective implant and wire lumens of the proximal shaft 1310 and the intermediate shaft can be configured so as to be axially aligned, allowing the wires 1314, 1316 to extend axially through the shafts 1306, 1310.

As shown in FIG. 62, the proximal shaft 1310 can also comprise a plurality of radially extending side openings or ports 1350 (four in the illustrated embodiment, but only two shown in FIG. 62) that are in communication with the lumens 1328 containing the control wires 1316. The side openings 1350 can be radially aligned with the ports 1330 of the intermediate shaft 1306. The ports 1350 of the proximal shaft 1310 can be disposed on the proximal shaft 1310 between the proximal nut 1340 of the basket expander mechanism 1308 and the control member 1312, allowing the control wires 1316 to exit the irrespective wire lumens 1328 of the proximal shaft 1310 via respective side openings 1350. The proximal shaft 1310 can be formed from a biocompatible polymer. For example, the proximal shaft 1310 can comprise Pebax with a Shore D hardness value of 72.

The steering control member 1312 of the delivery device 1300 can comprise a pivotable control handle 1352 and fixed sleeve portion 1354. The sleeve portion 1354 can be proximally disposed on and fixedly secured to the proximal shaft 1310, relative to the side ports 1350 of the proximal shaft 1310. The sleeve portion can comprise a spherical or at least partially spherical outer surface 1356. The control handle 1352 can comprise a socket portion 1358 (FIG. 62) disposed around the external surface 1356 of the sleeve 1354. In this manner, the external surface 1356 serves as a ball of a ball-in-socket joint formed with the socket portion 1358. This allows the socket 1358 and thus the control handle 1352 to be pivotable relative to the ball 1356.

The control handle 1352 can also comprise a plurality of axially extending openings 1360 (four in the illustrated embodiment, see FIG. 66) disposed radially outward on control handle 1352, relative to the socket 1358, configured to receive the proximal ends 1324 of respective control wires 1316, and thereby allowing the proximal ends 1324 of the control wires 1316 to be secured to the handle 1352. The openings 1360 can be angularly spaced apart from each other around the handle 1352, for example by approximately 90 degrees.

In some embodiments, as shown, the proximal ends 1324 of the respective control wires 1316 can be secured to the handle 1352 by inserting the proximal ends 1324 of the wires 1316 through respective openings 1360 and attaching respective end caps or ferrules 1362 to the proximal ends 1324 of the respective control wires 1316 which have a diameter exceeding the diameter of the openings 1360, thereby preventing the proximal ends 1324 of the control wires 1316 from retracting through the openings 1360. In other embodiments, the proximal ends 1324 of the control wires 1316 can, for example, be secured within the opening 1360 and thus to the handle 1352 by an adhesive. In some embodiments, the handle 1352 can be formed from a polymeric material such as acetal (e.g., Delrin®). In some embodiments, the sleeve 1354 can be formed from a polymeric material such as polycarbonate.

The opposite ends 1318, 1320 of the expander wires 1314 of the device 1300 can be fixedly secured to the sheath 1302 and the proximal shaft 1310, respectively. The wires 1314 desirably are evenly spaced apart from each other around the longitudinal axis of device, such as by 90 degrees. Also, the expander wires 1314 can each be substantially the same length axially and can be tensioned equally. Evenly distributing the expander wires 1314 circumferentially and providing substantially uniform tension on the expander wires 1314 can allow the sheath 1302, the intermediate shaft 1306, and the proximal shaft 1310 to maintain axial alignment when the basket 1304 expands upon adjustment of the basket expander mechanism 1308, as described above.

Similarly, the opposite ends 1322, 1324 of the control wires 1316 of the device 1300 can be fixedly secured to the sheath 1302 and the handle 1352, respectively. The control wires 1316 desirably are evenly spaced apart from each other around the longitudinal axis of the device, such as by 90 degrees. Also, the control wires 1316 can each be substantially the same length axially and can be tensioned equally. The length of the control wires 1316 can be selected such the control wires 1316 can comprise slack when the basket 1304 is in the axially elongate delivery configuration (FIG. 63*b*) and can be taut when the basket 1304 is in the radially expanded functional configuration.

Evenly distributing the control wires 1316 circumferentially and providing substantially uniform tension on the control wires 1316 can, for example, provide multi-directional control of the sheath 1302 and thus an implant device by pivoting (e.g., forward, backward, and/or side-to-side) the handle 1352 around the ball 1356. For example, referring to FIG. 62, pivoting the handle 1352 such that the upper portion of the handle 1352 moves proximally (i.e., in the direction of arrow 1374), is effective to pull the proximal ends 1324 of the upper control wires 1316 proximally, which in turn causes the sheath 1302 to pivot upwardly relative to the intermediate shaft 1306, in the direction of arrow 1376. To move the distal end of the sheath 1302 downwardly, a physician can pivot the handle 1352 of the control member 1312 such that the lower portion of the handle 1352 moves proximally (i.e., in the direction of arrow 1375), which is effective to, pull the proximal ends 1324 of the lower control wires 1316 proximally, which in turn causes the distal end of the sheath 1302 to pivot downwardly relative to the intermediate shaft 1306, in the direction of arrow 1378.

The delivery device 1300 can be used, for example, to percutaneously deliver a prosthetic implant. For example, FIG. 67 shows the delivery device 1300 being used to deliver a prosthetic spacer device 1364 into the mitral valve 1366 of a heart 1368. With a prosthetic implant device pre-loaded into the sheath 1302, the delivery device 1300 can be advanced through an outer catheter 1370 into the left atrium 1371 of the heart 1368. With the sheath 1302, the basket 1304, and the intermediate shaft 1306 of the device 1300 in the left atrium, the basket 1304 can be expanded to the functional configuration by rotating the outer nut 1342 of the basket expander 1308 so as to move the intermediate shaft 1306 toward the sheath (described in greater detail above). Expanding the basket 1304 of the device 1300 brings the control wires 1316 taut and allows the physician to then desirably orient the prosthetic spacer device 1364 by pivoting the handle 1352 of the control member 1312. For example, the physician can cause the sheath 1302 to make a 90 degree turn, relative to the outer catheter 1370, to align the prosthetic spacer device 1364 with the patient's mitral valve 1366.

Once the prosthetic device 1364 is desirably oriented, the prosthetic spacer device 1364 can be advanced from the sheath 1302 of the device 1300 and thereafter secured to the native leaflets 1372 of the mitral valve 1366, such as previously described with respect to the prosthetic spacer devices herein described. Subsequently, the basket 1304 can be radially compressed back to the delivery configuration by actuating the basket expander mechanism 1308, thus allowing the delivery device 1300 to be retracted into the outer catheter 1370 and removed from the patient.

The implant lumens 1348, 1326 of the shafts 1310, 1306 (respectively) can, for example, advantageously allow a physician to introduce additional catheters (e.g., an implant catheter) during a procedure without having to retract the delivery device from the patient. These additional catheters which are introduced through the implant lumens 1348, 1326 can, for example, be used to deploy a prosthetic spacer device.

Figure 68:
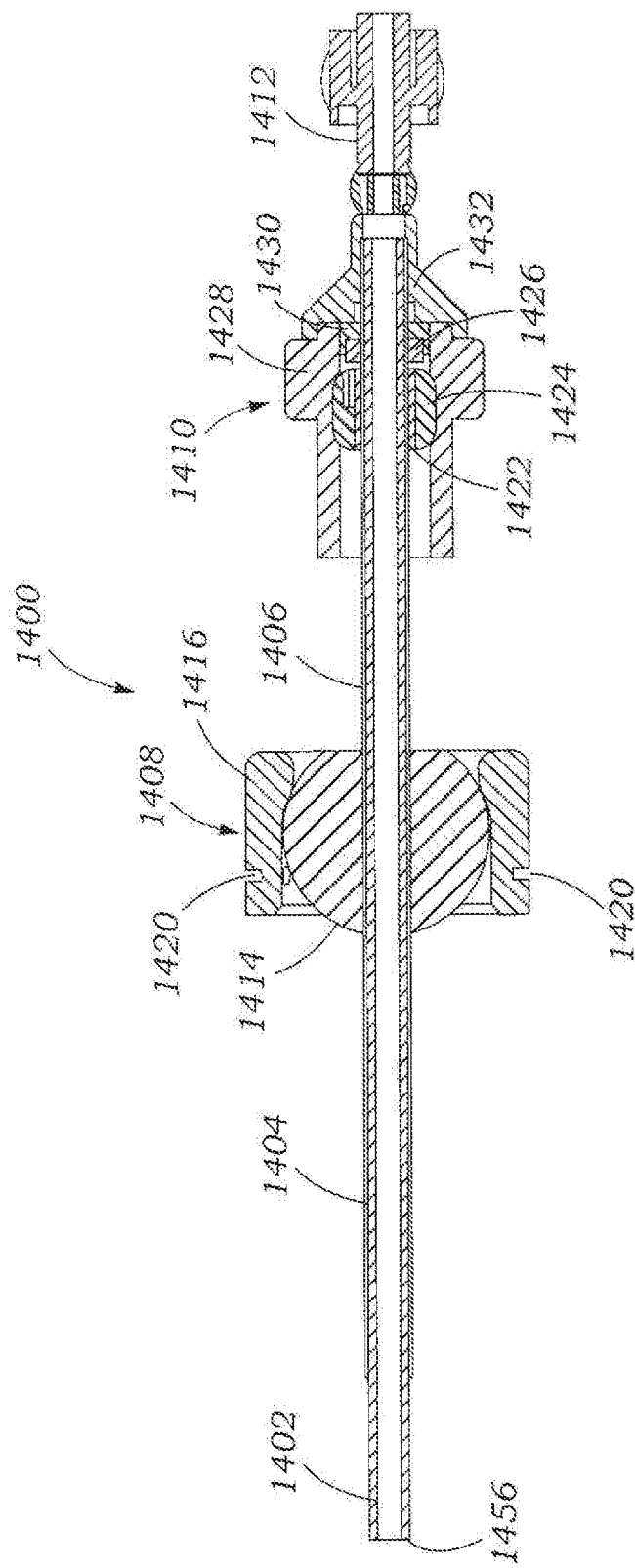
FIG. 68 is a side of a steerable delivery device for an implantable prosthetic device, according to another embodiment.

FIG. 68 shows another exemplary steerable prosthetic implant delivery device 1400, according to another embodiment. The delivery device 1400 can comprise a flexible inner shaft 1402, an intermediate shaft 1404, a slidable outer shaft 1406, a steering control member 1408, a wire tensioner shaft 1410, a plurality of pivot control wires (not shown, but similar to wires 1316), and a hemostasis seal 1412 (e.g., tapered Luer fitting). The inner shaft 1402, the intermediate shaft 1404, and the outer shaft 1406 can extend co-axially through the control member 1408 and the tensioner 1410, respectively. The inner shaft 1402 and the intermediate shaft 1404 can extend co-axially through the outer shaft 1406, and the inner shaft 1402 can also extend co-axially through the intermediate shaft 1404. The inner shaft 1402 can be fixedly secured (e.g., with an adhesive) to the intermediate shaft 1404. The outer shaft 1406 can be disposed around and axially moveable (i.e., distally or proximally) relative to the intermediate shaft 1404.

Figure 69:
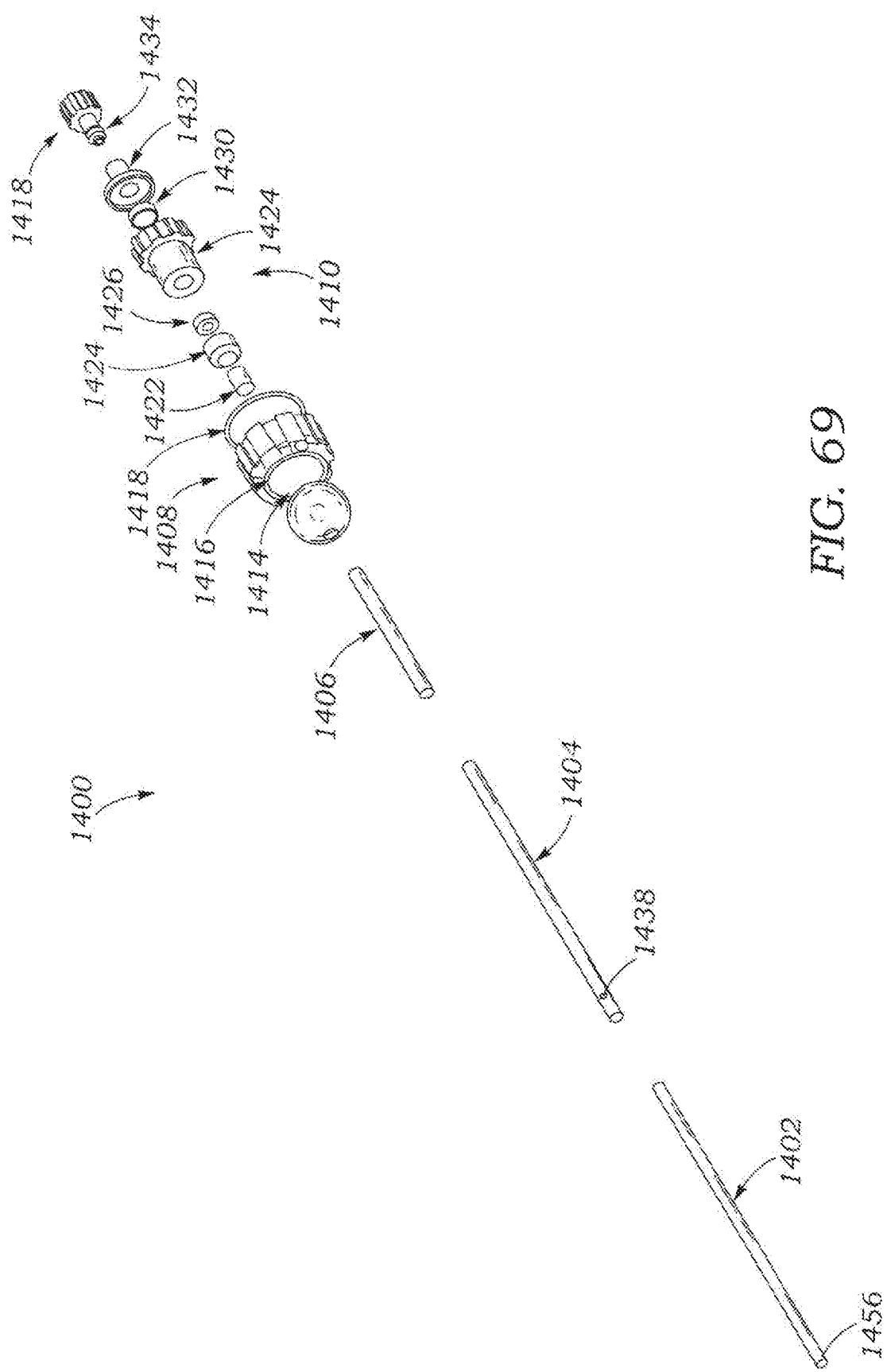
FIG. 69 is a perspective, exploded view of the delivery device of FIG. 68.

The control member 1408 of the delivery device 1400 can comprise a ball 1414, a handle 1416, and a ring 1418 (FIG. 69). The ball 1412 can be disposed around and fixedly secured (e.g., with an adhesive) to the distal end of the outer shaft 1406. The handle 1416 can be disposed around and pivotably connected to the ball 1414. The ring 1418 can be disposed within an annular notch or groove 1420 formed within the outer surface of the handle 1416.

Figure 66:
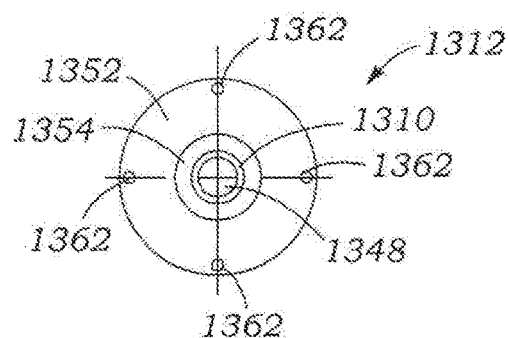
FIG. 66 is a cross-sectional view of the proximal shaft of the delivery device of FIG. 62.

The plurality of pivot control wires (not shown) of the delivery device 1400 can, for example, include four pivot control wires similar to the control wires 1316. The control wires can have first, distal ends be fixedly secured or attached to the distal end 1454 of the inner shaft 1402 and second, proximal ends fixedly secured or attached to the ring 1418 and thus the handle 1416. The control wires can be annularly distributed around the central axis of the inner shaft 1402 and the handle 1416, spaced apart from each other by 90 degrees in a manner similar to the control wires 1316, described above in connection with the sheath 1302 and the control handle 1352 (FIGS. 62, 66). The control wires can extend proximally through respective lumens of the inner shaft 1402, and outwardly through respective exit ports (in shown) in the inner and intermediate shafts 1402, 1404 where the proximal ends of the control wires can be attached to the ring 1418. The ports of the inner shaft 1402 can be oriented so as to align circumferentially with respective ports of the intermediate shaft 1404.

The control member 1408 and the pivot control wires can, for example, allow a physician to control the distal end 1456 of the flexible tube 1402 by pivoting the handle 1416 relative to the ball 1414 in a manner similar to that described above with respect to delivery device 1300. Sometimes, during use, the control wires can become undesirably slackened due to, for example, pivoting the handle 1416 and to extreme orientations, which can reduce the effectiveness of the handle 1416 to control the distal end 1456 of the flexible tube 1402. To alleviate and/or eliminate this problem, the delivery device 1400 can, for example, comprise a tensioner 1410 to remove undesirable slack in the control wires, as further described below.

The tensioner 1410 of the delivery device 1400 can comprise a nut guide adapter 1422, a drive nut 1424, a stop washer 1426, a wire tension adjustment knob 1428, an adjustment nut washer 1430, and an end cap 1432. The guide nut 1422 can be fixedly secured to the proximal end of the outer shaft 1406. The guide nut 1422 can comprise external threads (not shown) which can be configured to engage corresponding internal threads (not shown) of the drive nut 1424. The drive nut 1424 can also comprise external threads (not shown) corresponding to and engaging the internal threads (not shown) of the wire tension adjustment knob 1428.

The adjustment knob 1428 can be coupled to and rotatable relative to the end cap 1432. The end cap 1432 can be fixedly secured or coupled to the proximal ends of the inner shaft 1402 and the intermediate shaft 1404. In this manner, rotation of the adjustment knob 1428 relative to the guide nut 1422 and the drive nut 1424 in a first direction causes the nuts 1422, 1424 and thus the outer shaft 1406, ball 1414, and handle 1416 to move proximally, relative to the inner and intermediate shafts 1402, 1404. Rotation of the adjustment knob 1428 relative to the nuts 1422, 1424 in a second direction (opposite the first direction) causes nuts 1422, 1424 and thus the outer shaft 1406, ball 1414, and handle 1416 to move distally, relative to the shafts 1402, 1404. Thus, because the control wires are fixed to the sheath at the distal ends of the wires and to the handle 1416 at the proximal ends of the wires, rotating the adjustment knob 1428 in the first direction applies tension to the control wires and reduces the slack in the control wires. It should be noted that the tensioner 1410 can, for example, be used on various delivery devices, including the delivery device 1300.

Figure 70A:
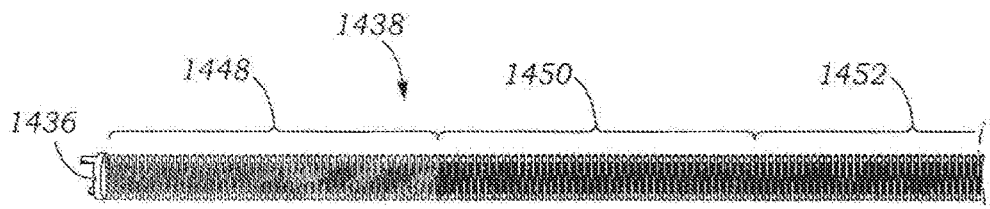
FIGS. 70*a*-71*b* show various views of a slotted metal tube that can be incorporated in the inner steerable shaft of the delivery device of FIG. 68.
Figure 70B:
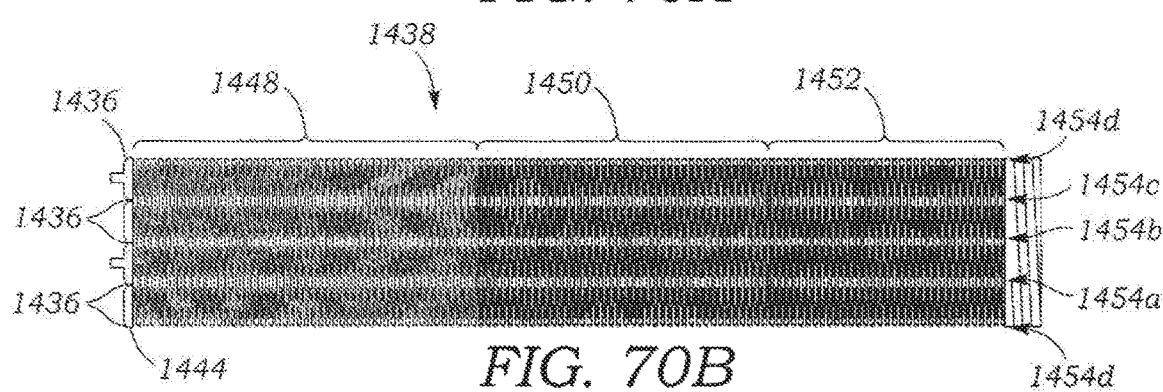
Figure 71A:
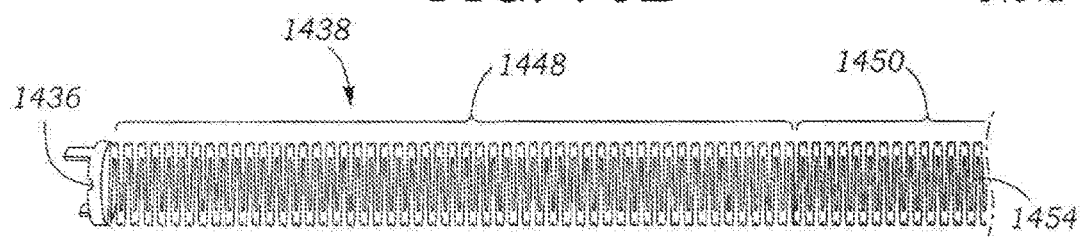
Figure 71B:
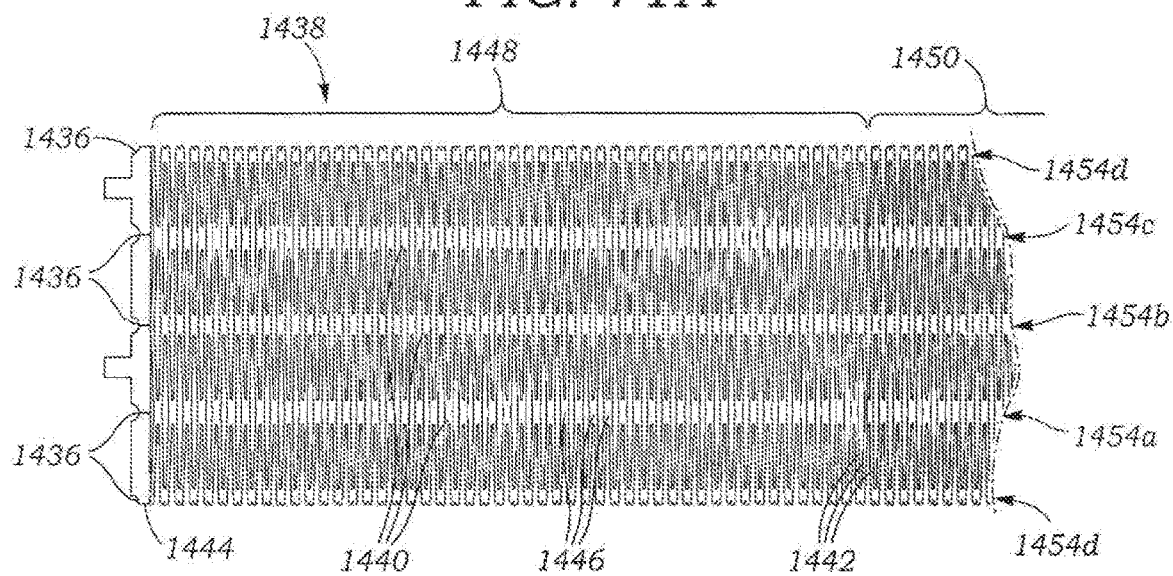

The inner shaft 1402 of the device 1400 can comprises a slotted metal tube 1438, as shown in FIGS. 70*a*-71*b*. The metal tube 1438 can be formed, for example, by laser cutting an alloy tube (e.g., Nitinol, stainless steel, cobalt chromium, etc.). As best shown in FIG. 71*b*, the tube 1438 can comprise a plurality of spine portions 1440 and a plurality of struts 1442 disposed between and interconnecting the spine portions 1440. The tube 1438 can also comprise an annular collar 1444 disposed at the distal end of the tube 1438.

The tube 1438 can be coated, both externally and internally, with a flexible polymeric coating. The spine portions 1440 of the tube 1438 can comprise openings 1446 (FIG. 71*b*) which can, for example, allow the polymeric coating to evenly distribute throughout the tube 1438, providing a desirably uniform wall thickness for the inner shaft 1402.

The tube 1438 can be configured such that the spine portions 1440 form axially extending rows 1454 that are separated by the struts 1442. For example, in the illustrated embodiment (best shown in FIG. 71*b*), the spine portions 1440 are configured in four axially extending rows 1454*a*, 1454*b*, 1454*c*, 1454*d* (in FIGS. 70*b* and 71*b*, the row 1454*d* is cut axially down the center to show the tube 1438 in a flat configuration for illustrative purposes). The rows 1454*a*-1454*d* can be angularly spaced apart from each other (e.g., by 90 degrees), and the rows 1454 can be configured such that the spine portions 1440 of the rows 1454 are axially offset relative to the spine portions 1440 of a radially adjacent rows 1454. Configuring the tube 1438 in this manner allows the tube 1438 to flex or bend more uniformly in all directions and reduces kinking when compared to a solid tube or a tube with a single, solid spine portion.

The collar 1444 of the tube 1438 can comprise distally extending tabs 1446 (two in the illustrated embodiment). In an embodiment in which the control wires are not fixedly secured or attached directly to the distal end 1456 of the flexible shaft 1402 but are attached to a separate pull ring (not shown), the tabs 1446 can be used, for example, to orient the tube 1438 with the pull ring. The pull ring can be attached to the distal end 1456 of the flexible shaft 1402, for example, by inserting the tabs 1446 into pull ring. In such an embodiment, the collar 1444 of the tube 1438 can also comprise radially extending side notches or ports 1436 (four in the illustrated embodiment) which can, for example, be used to allow the control wires to enter the tube 1438 and pass through the inner diameter of the flexible tube 1402.

The tube 1438 of the inner shaft 1402 can also comprise different axial sections (three in the illustrated embodiment) 1448, 1450, 1452, as best shown in FIGS. 70*a*-70*b*. The different axial sections 1448, 1450, 1452 can, for example, comprise differently sized struts 1442. Providing differently sized struts 1442 (i.e., removing more or less material), allows different axial sections to have either a smaller or larger bend radiuses. For example, the distal section 1448 comprises the thinnest struts (i.e., the most material removed) compared to the more proximal sections 1450, 1452, allowing distal section 1448 to have the smallest bend radius, relative to more proximal sections 1450, 1452. Also, the intermediate section 1450 has thinner struts than the proximal section 1452, allowing the intermediate section 1450 to have a smaller bend radius than the proximal section. It should be noted that although the illustrated embodiment shows the smallest struts located distally and the largest struts located proximally, relative to the other sections, the axial sections can be configured in any order or combination to achieve the desired result for a particular application.

Figure 72:
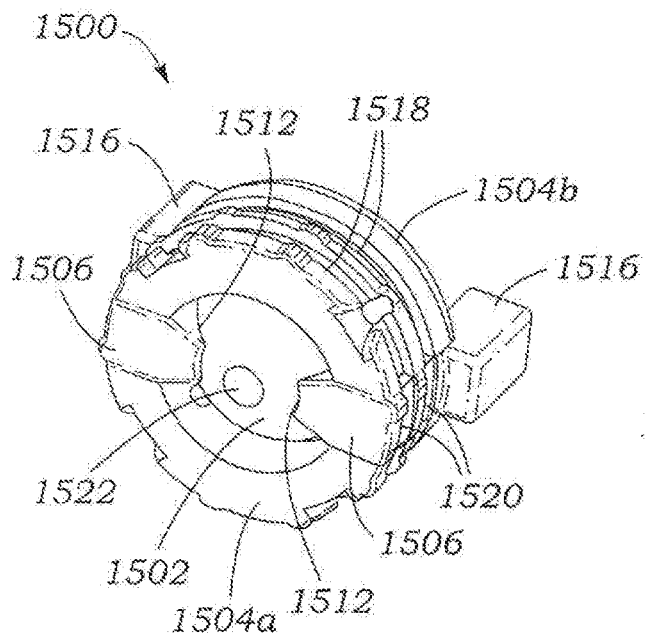
FIGS. 72-74 show various views of an alternative embodiment of a steering control member that can be incorporated in a delivery device.
Figure 73:
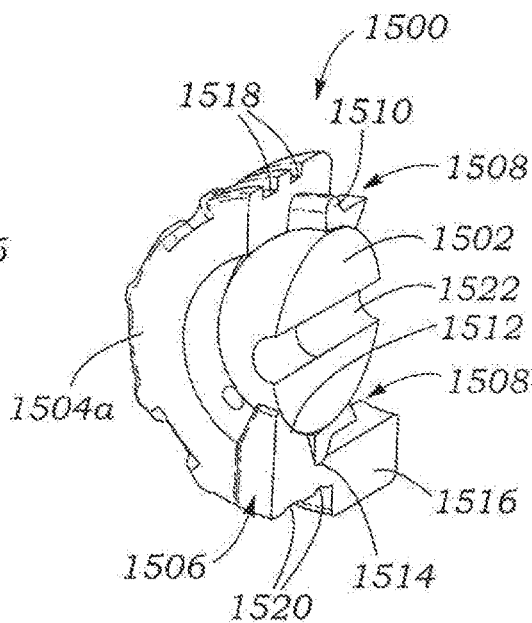
Figure 74:
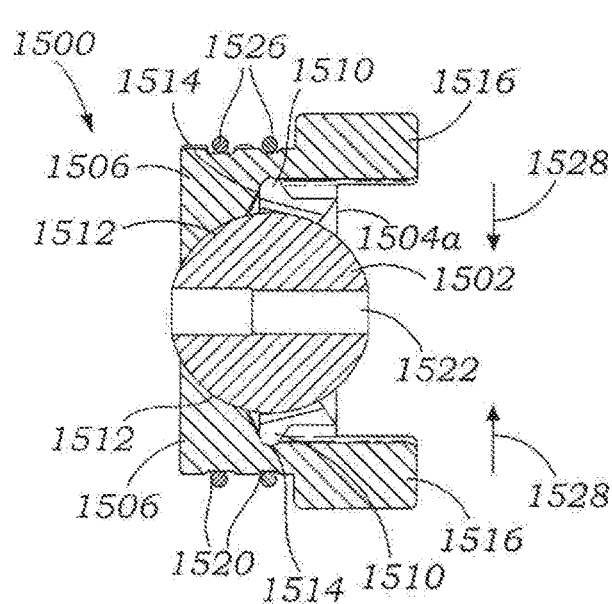

FIGS. 72-74 show an exemplary embodiment of a control member 1500, similar to control members 1312, 1408 of the delivery devices 1300, 1400, respectively. In the illustrated embodiment, the control member 1500 comprises a ball 1502, a socket 1504, and at least one clip 1506 (two in the illustrated embodiment). The socket 1504 can comprise a first socket portion 1504*a* and a second socket portion 1504*b*. The socket portions 1504*a*, 1504*b* can be separated, radially, by the clips 1506. The ball 1502 can comprise an inner opening or lumen 1522, which can allow other devices (e.g. a catheter tube, etc.) to pass through the ball 1502. The socket 1504 can be disposed around the ball 1502 such that the socket is rotatable relative to the ball (similar to a ball-joint).

The socket portions 1504*a*, 1504*b* can comprise at least one radially extending cut-out or recessed portion 1508 (two in the illustrated embodiment) (FIG. 73) configured to receive a respective clip 1506. Each recessed portion 1508 can contain a respective projection 1510. The clips 1506 can be positioned within the recessed portions 1508. The clips 1506 can each comprise a ball-contact surface 1512, a groove or slot 1514 (FIGS. 73-74), and tabs 1516.

The control member 1500 can further include a securing mechanism 1526 (FIG. 74) that extends annularly around the socket portions 1504*a*, 1504*b* and the clips 1506 that holds the socket portions 1504*a*, 1504*b* and the clips 1506 together and presses the socket portions 1504*a*, 1504*b* and the clips 1506 radially inward against the ball 1504. The securing mechanism 1526 can, for example, be one or more biasing elements (e.g., O-rings or elastic bands) placed within grooves 1518, 1520 of the socket portions 1504*a*, 1504*b* and the clips 1506, respectively. In another embodiment, the securing mechanism can be, for example, a spring or any other force applying mechanism.

The ball-contact surface 1512 can be configured to press against and apply a frictional force on the outer surface of the ball 1502 to resist movement of the socket 1504 relative to the ball 1502 when manual pressure is removed from the socket 1504 and the clips 1506. The grooves 1514 of the clips 1506 can be positioned to abut the projections 1510, thereby allowing the clips 1506 to pivot about the projections 1510 with the projections 1510 acting as the fulcra. The clips 1506 can be pivoted by squeezing or pinching the tabs 1516 together (in the direction of arrows 1528 in FIG. 74), causing the tabs 1516 to move radially inward. Pivoting the clips 1506 in this manner moves the ball-contract surface 1512 radially outward away from the outer surface of the ball 1502, thereby allowing the socket 1504 and the clips 1506 to rotate relative to the ball 1502. Releasing manual pressure from the tabs 1516 allows the clips 1506 to move back in contact with the ball under the biasing force of the securing mechanism 1526.

Thus, the clips 1506 of the control member 1500 can function as a locking mechanism for securing the control member 1500 in a desired orientation. For example, when using the control member 1500 as part of a delivery device (e.g., delivery devices 1300, 1400), a physician can squeeze the tabs 1516 of the clips 1506 and pivot the socket portions 1504 (relative to the ball 1502), pulling the control wires (e.g., control wires 1316) and thus the sheath (e.g., sheath 1302) (as described above) to a desired orientation. The physician can then lock the socket portions 1504 and thus the sheath in the desired configuration by releasing the tabs 1516, allowing the ball-contact surface 1512 of the clips 1506 to press against the ball 1502 and resist movement of the socket portions 1504 relative to the ball 1502, thereby retaining the sheath in the desired orientation. This can advantageously, for example, allow a physician to orient the delivery device to a desired configuration with one hand, subsequently release that hand from the delivery device and then use both hands to perform another task (e.g., deploying a prosthetic implant with an implant catheter).

Figure 75:
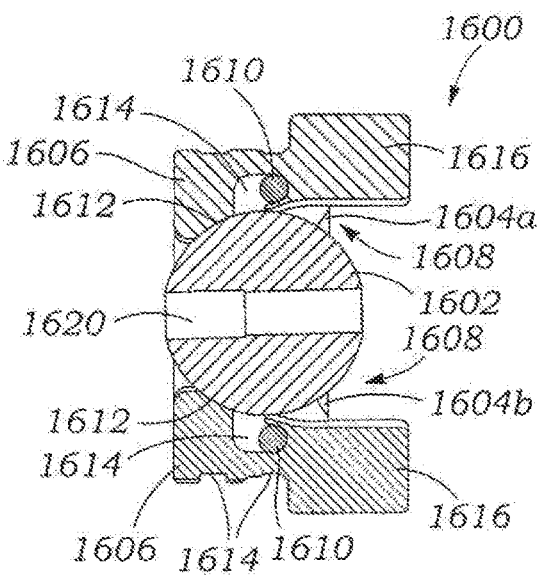
FIG. 75 is a cross-sectional view of another embodiment of a steering control member that can be incorporated in a delivery device.
Figure 76:
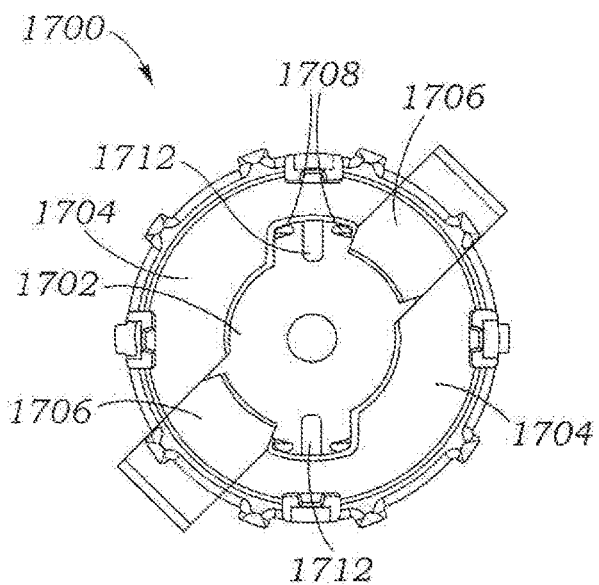
FIGS. 76-79 show various views of an alternative embodiment of a steering control member that can be incorporated in a delivery device.
Figure 77:
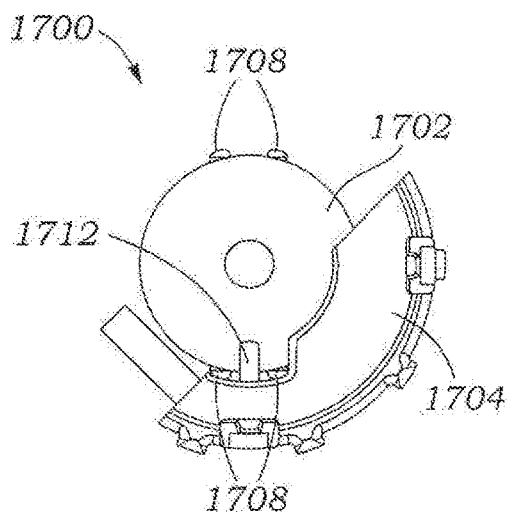

FIG. 75 shows another exemplary embodiment of a control member 1600, similar to control member 1500, including a ball 1602, a socket 1604, and clips 1606. The ball 1602 can comprise an inner opening or lumen 1620, which can allow the ball to be mounted on the shaft of a delivery device. The sockets 1604 can comprise recessed portions 1608 configured to receive the clips 1606, the recessed portions 1608 housing rods or shafts 1610. The clips 1606 each comprise ball-contact surfaces 1612, grooves or slots 1614, and tabs 1616.

The sockets 1604 can further comprise grooves (not shown, but similar to grooves 1518), and the clips 1606 can further comprise grooves 1618. The grooves in the sockets 1604 and the clips 1606 (i.e., grooves 1618) can be configured to receive a securing mechanism (e.g., O-ring, spring, etc.) to hold the sockets 1604 and clips 1606 together and against the ball 1602. The control device 1600 can function in a manner substantially similar to control member 1500, as described above. As a result, the control member 1600 can, for example, provide similar locking-type features and advantages described with respect to control member 1500.

FIGS. 76-79 show an exemplary embodiment of a control member 1700, similar to control member 1600, including a ball 1702, a socket portion 1704, and clips 1706. The illustrated embodiment can be "unlocked" (i.e., allowing the socket portion 1704 to rotate relative to the ball 1702) and "locked" (i.e., preventing the socket portion 1704 from rotating relative to the ball 1702) in a manner similar to the control member 1600.

Figure 78:
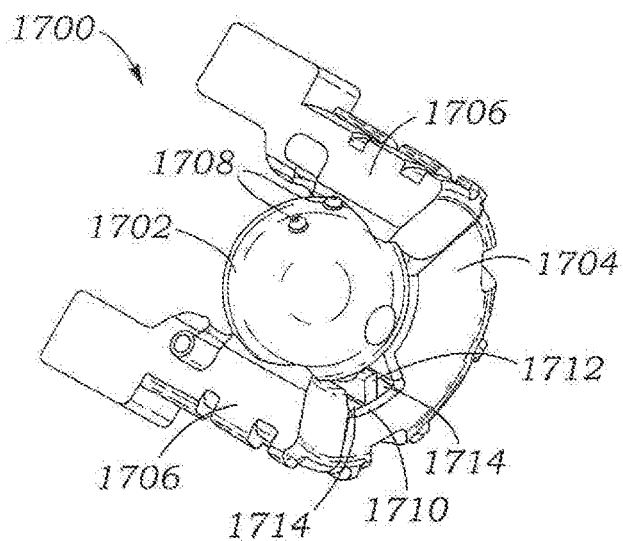
Figure 79:
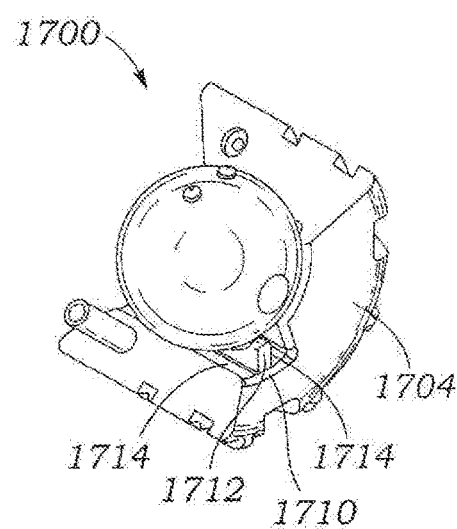

The ball 1702 of control member 1700 can comprise a plurality of pins or projections 1708 (four in the illustrated embodiment) disposed on and extending radially outward from the outer surface of the ball 1702. The socket portion 1704 can comprise axially extending recessed portions 1710 (two in the illustrated embodiment) (FIGS. 78-79) and guide rails 1712 disposed within the recessed portions, with the guide rails 1712 dividing the recessed portions 1710 into two tracks or channels 1714 (FIGS. 78-79). The channels 1714 can be configured such that the projections 1708 of the ball 1702 can travel or move axially within the socket 1704 as the socket 1704 pivots about the ball 1702.

Due to the positioning of the projections 1708 of the ball 1702 in the guide rails 1712 of the socket 1704, however, the socket 1704 cannot torque or rotate annularly, relative to the ball 1702. This anti-torquing feature of the control member 1700 advantageously prevents, for example, a physician from torquing the socket 1704 and thus twisting the control wires (not shown). These features can, for example, make the control member 1700 and thus a delivery device easier to operate because the socket 1704 can only move in an intended manner. This anti-torquing feature can also, advantageously, for example, reduce the possibility that a physician will inadvertently damage the control member 1700 and/or the delivery device by using the control member in an unintended manner.

Figure 80:
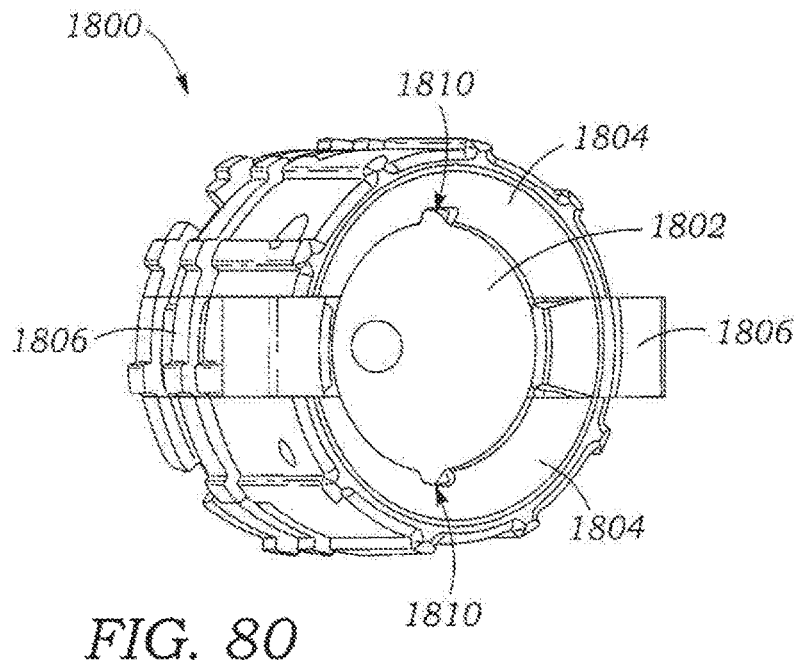
FIGS. 80-82 show various views of an alternative embodiment of a steering control member that can be incorporated in a delivery device.
Figure 81:
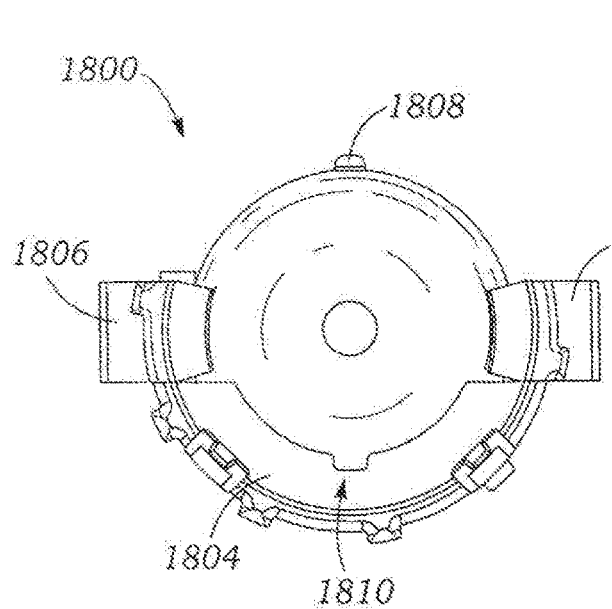
Figure 82:
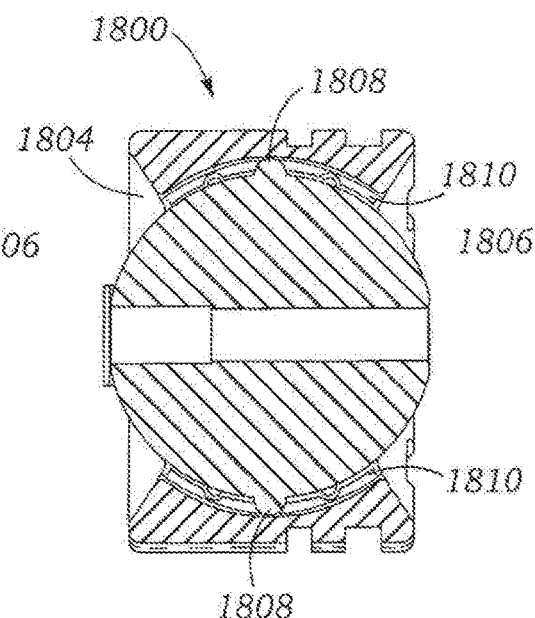

FIGS. 80-82 show an exemplary embodiment of a control member 1800, similar to control member 1600, including a ball 1802, a socket portion 1804, and clips 1806. The illustrated embodiment can be "unlocked" (i.e., allowing the socket portion 1804 to rotate relative to the ball 1802) and "locked" (i.e., preventing the socket portion 1804 from rotating relative to the ball 1802) in a manner similar to the control member 1600.

The ball 1802 of control member 1800 can comprise a plurality of pins or projections 1808 (two in the illustrated embodiment) disposed on and extending radially outward from the outer surface of the ball 1802. The socket portion 1804 can comprise axially extending recesses or channels 1810 (two in the illustrated embodiment) configured to receive the projections 1808 such that the projections 1808 can travel or move axially within the socket 1804 as the socket 1804 pivots about the ball 1802. However, due to the positioning of the projections 1808 in the channel 1810, the socket portion 1804 cannot torque or rotate annularly, relative to the ball 1802. This anti-torquing feature can, for example, provide at least the advantages described with respect to control member 1700.

Figure 83:
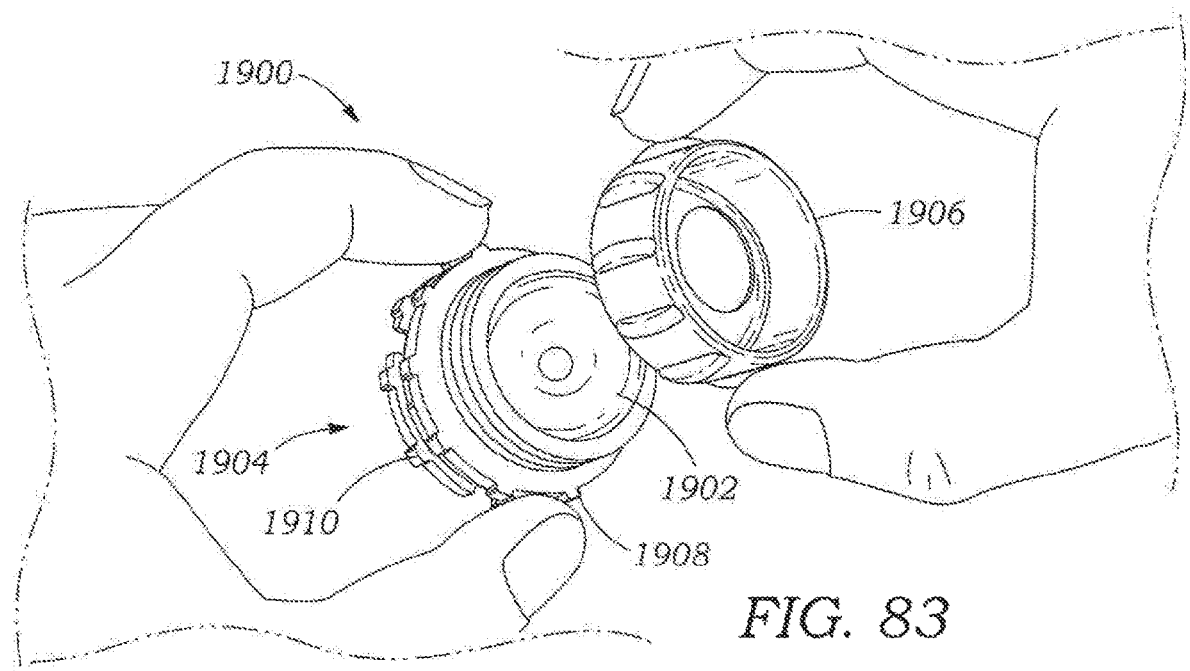
FIGS. 83-85 show various views of an alternative embodiment of a steering control member that can be incorporated in a delivery device.
Figure 84:
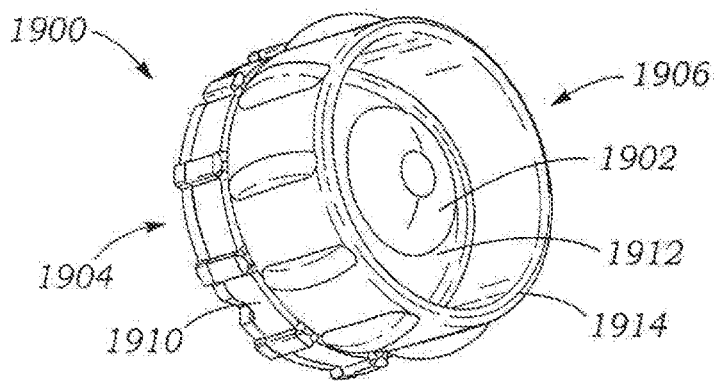
Figure 85:
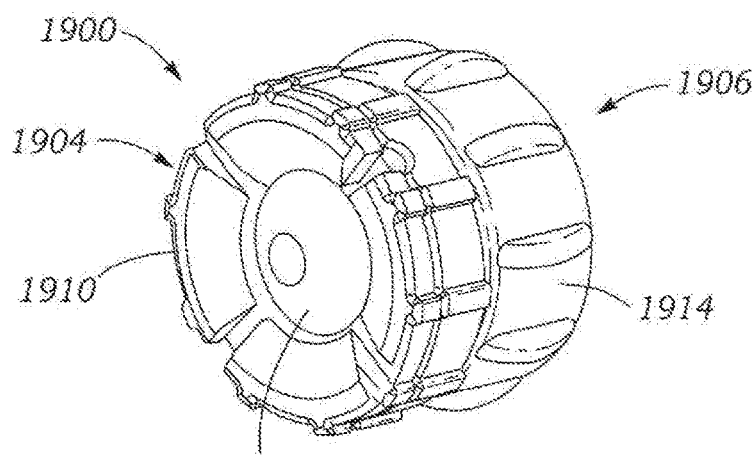

FIGS. 83-85 show an exemplary control member 1900, according to one embodiment. The control member 1900 can function, for example, in a manner substantially similar to control member 1408 of device 1400. In the illustrated embodiment, the control member 1900 comprises a ball 1902, a socket portion 1904, and a lock 1906. The socket 1904 can comprise a generally spherically-shaped surface (not shown) disposed around the ball 1902 (similar to a ball-joint), an externally-threaded portion 1908 at the proximal end of the socket 1904, and a flange or handle portion 1910 extending radially from the distal end of the externally-threaded portion 1908, as best shown in FIG. 83.

The lock 1906 can comprise a generally spherically-shaped interior surface 1912 having internal threads, configured to receive the externally-threaded portion 1908 of the socket 1904, and a knob 1914 disposed radially outward from the surface 1912. In this manner, rotation of the knob 1914 and thus the lock 1906 relative to the ball 1902 and the socket 1904 in a first direction moves the socket 1904 and the lock 1906 axially towards each other, urging the surface 1912 of the lock 1906 against the ball 1902, and thereby preventing the socket 1904 from pivoting or rotating relative to the ball 1902 (i.e., "locking" the socket 1904); and rotation of the knob 1914 in a second direction (the second direction being opposite the first) moves the socket 1904 and the lock 1906 axially towards away from each other, removing the surface 1912 of the lock 1906 from the ball 1902, and thereby allowing the socket 1904 to pivot or rotate relative to the ball 1902 (i.e., "unlocking" the socket 1904).

Figure 86:
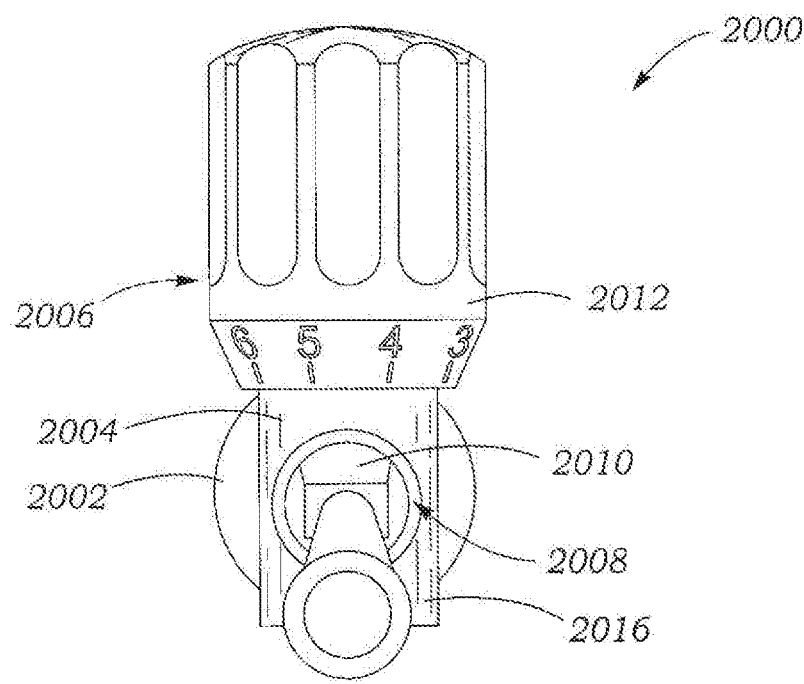
FIGS. 86-87 are end and side views, respectively, of a catheter-position locking device, according to one embodiment.
Figure 87:
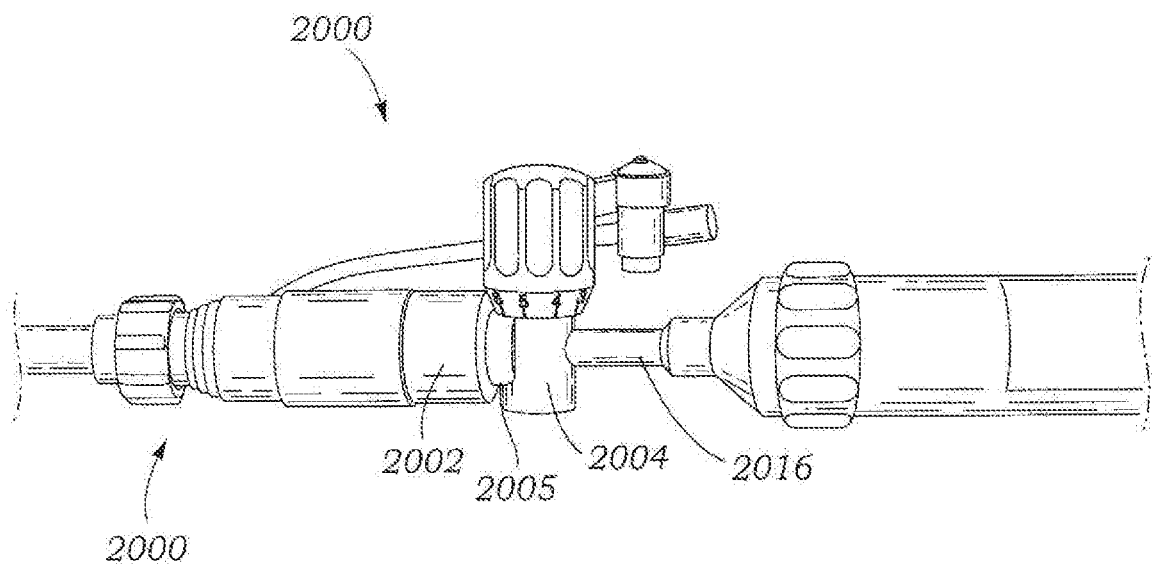

FIGS. 86-87 show an exemplary catheter-position locking device 2000, according to one embodiment. In the illustrated embodiment, the locking device 2000 comprises a coupler or sleeve 2002 (best shown in FIG. 87), a housing 2004, and a fastener portion 2006. As best shown in FIG. 87, the sleeve 2002 can extend co-axially over a distal shaft portion 2005 of the housing 2004. The housing 2004 can comprise an axially extending lumen 2008 and a radial opening (not shown), the radial opening being generally perpendicular to the lumen 2008 and comprising internal threads. The fastener 2006 can comprise an externally-threaded plug 2010 that engages the internal threads of the radial opening of the housing 2004 and can extend through the radial opening into the lumen of the housing. The fastener 2006 can also comprise a head portion or knob 2012 fixedly secured to the upper end portion of the plug 2010.

In use, rotation of the head 2012 and thus the plug 2010 in a first direction relative to the housing 2004 moves the plug 2010 06 radially inwardly, thereby obstructing the lumen 2008 of the housing 2004, and rotation of the rotation of the head 2012 of the fastener 2006 in a second direction (the second direction being opposite the first) relative to the housing 2004 moves the plug 2010 radially outwardly, thereby removing the plug 2010 from the lumen 2008 of the housing 2004.

The device 2000 can, for example, be used to allow one catheter or sheath to be desirably positioned relative to another catheter or sheath and then secured in the desirable position. For example, FIG. 87 shows the device 2000 being used with an introducer sheath 2014 and an outer catheter 2016. In some embodiment, as shown, the device 2000 can be fixedly secured or coupled to the proximal end of the introducer sheath 2014 by advancing the distal end of the sleeve 2002 of the device 2000 over the sheath 2014. In other embodiments, the device 2000 can be fixedly secured or coupled to the proximal end of the introducer sheath by an adhesive, fasteners, etc.

With the axial opening 2008 of the device 2000 clear or open (i.e., the plug 2010 of the fastener 2006 not obstructing the axial opening 2008), the outer catheter 2016 can be advanced through the device 2000 and the introducer sheath 2014. In this open or clear configuration, the outer catheter 2016 can torque/rotate and/or move axially (i.e., distally or proximally) relative to the device 2000 and thus the introducer sheath 2014, allowing the outer catheter 2016 to be desirably positioned. Once the outer catheter 2016 is desirably positioned, the outer catheter can be secured in the desirable position by rotating the head 2012 of the fastener 2006 in the first direction, causing the plug 2010 to move inward and press against the outer catheter 2016 (as best shown in FIG. 86), thereby preventing the outer catheter from torquing/rotating and or moving axially relative to the introducer sheath 2014. Thus, the device 2000 can, for example, advantageously allow a physician to both adjust and secure a catheter during a procedure, making the procedure both significantly safer and easier to perform.

Figure 88:
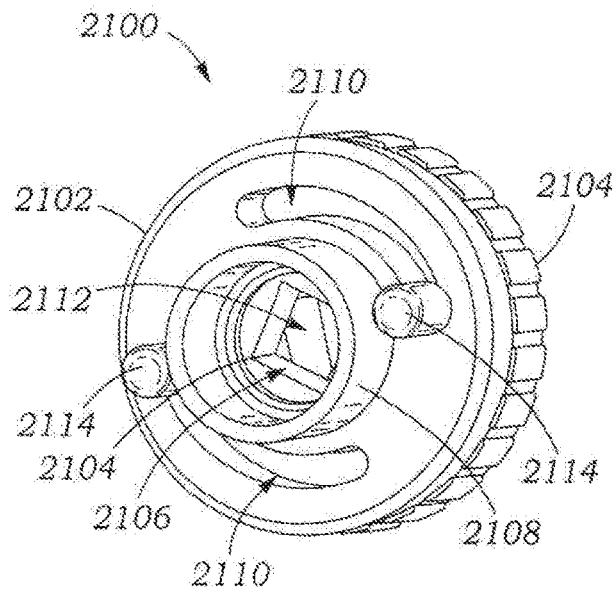
FIGS. 88-91 show various views of another embodiment of a catheter-position locking device.
Figure 89:
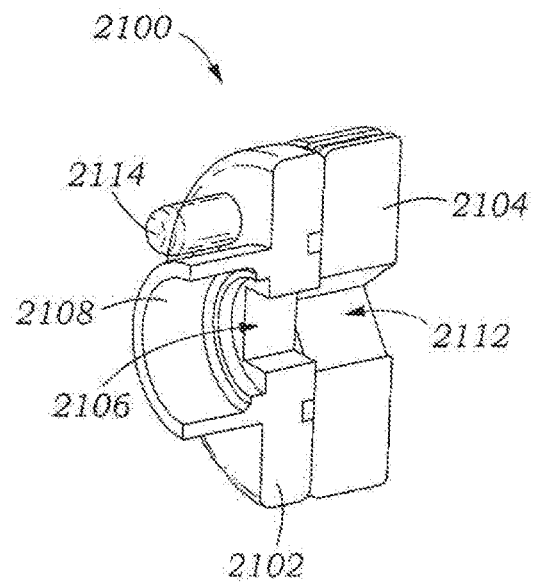

FIGS. 88-91 show an exemplary catheter-position locking device 2100, according to another embodiment. In the illustrated embodiment, the locking device 2100 comprises a fixed portion 2102 and a moveable portion 2104 connected to the fixed portion 2102, with the moveable portion 2104 being rotatable relative to the fixed portion 2102. The fixed portion 2102 of the device can comprise a centrally disposed opening 2106, an axially extending sleeve 2108 disposed radially outward from the opening 2106, and circumferentially extending notches or grooves 2110 disposed radially outward from the sleeve 2108. The moveable portion 2104 can comprise a centrally disposed opening 2112 and axially extending pins 2114 disposed radially outward from the opening 2112. The pins 2114 of the moveable portion 2104 can be configured to axially extend through respective grooves 2110 of the fixed portion, as best shown in FIG. 88.

It should be noted that although the openings 2106, 2112 are shown as having a generally square cross-section, the openings 2106, 2112 can comprise various other shapes.

Figure 90:
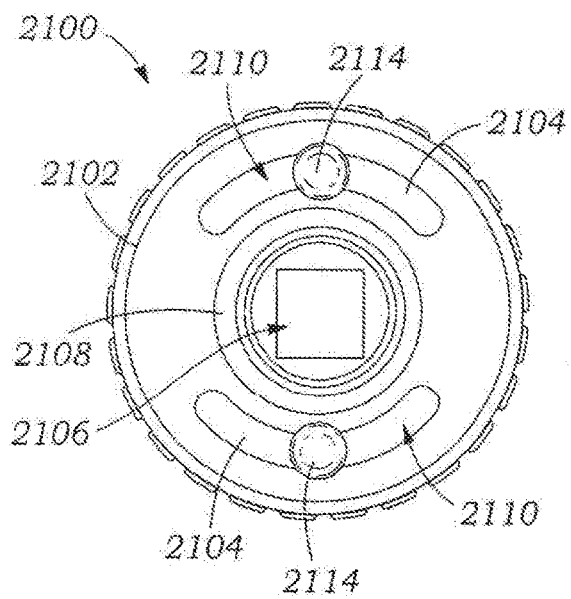
Figure 91:
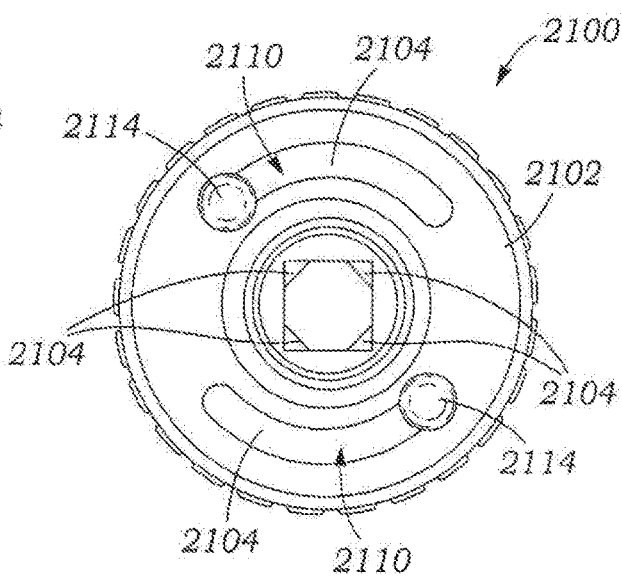
Figure 92:
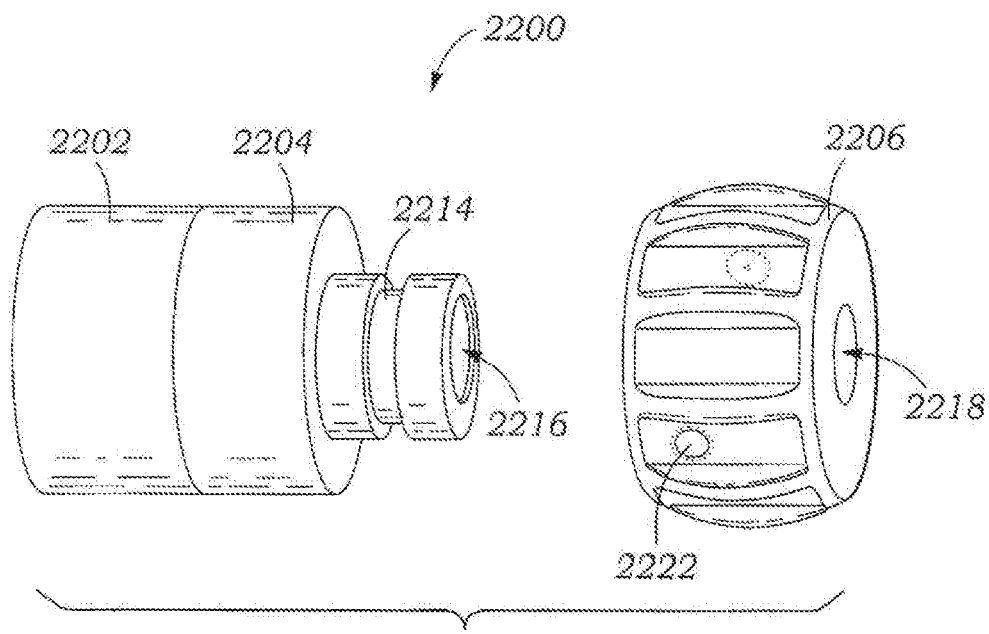
FIGS. 92-96 show various views of another embodiment of a catheter-position locking device.

As best shown in FIGS. 90-91, the openings 2106, 2112 of the respective portions 2102, 2104 can be configured such that rotating the movable portion 2104 relative to the fixed portion 2102 to a first, unlocked position aligns the opening 2112 of the moveable portion 2104 with the opening 2106 of the fixed portion 2102 (FIG. 90). Rotating the movable portion 2104 relative to the fixed portion 2102 to a second, locked position causes the opening 2112 of the moveable portion 2104 to become misaligned with the opening 2106 such that the moveable portion 2104 interferes with or partially obstructs the opening 2106 of the fixed portion 2102 (FIG. 91).

Although not shown, the device 2100 can, for example, be used with an introducer sheath and outer catheter similar to sheath 2014 and catheter 2016. The sleeve 2108 of the fixed portion 2102 of the device 2100 can be fixedly secured or coupled (e.g., with an adhesive, fasteners, etc.) to the proximal end of the introducer sheath. With the movable portion rotated to the first, aligned position, the outer catheter can be advanced through the device 2100 and the introducer sheath. With the movable portion 2104 in the aligned position, the outer catheter can torque/rotate and/or move axially relative to the device 2100 and the introducer sheath to a desirable positioning. Once desirably positioned, the moveable portion 2104 can be rotated to a second, misaligned position causing the movable portion 2104 to press against the outer catheter, thereby preventing the outer catheter from torquing/rotating and or moving axially relative to the introducer sheath.

Figure 93:
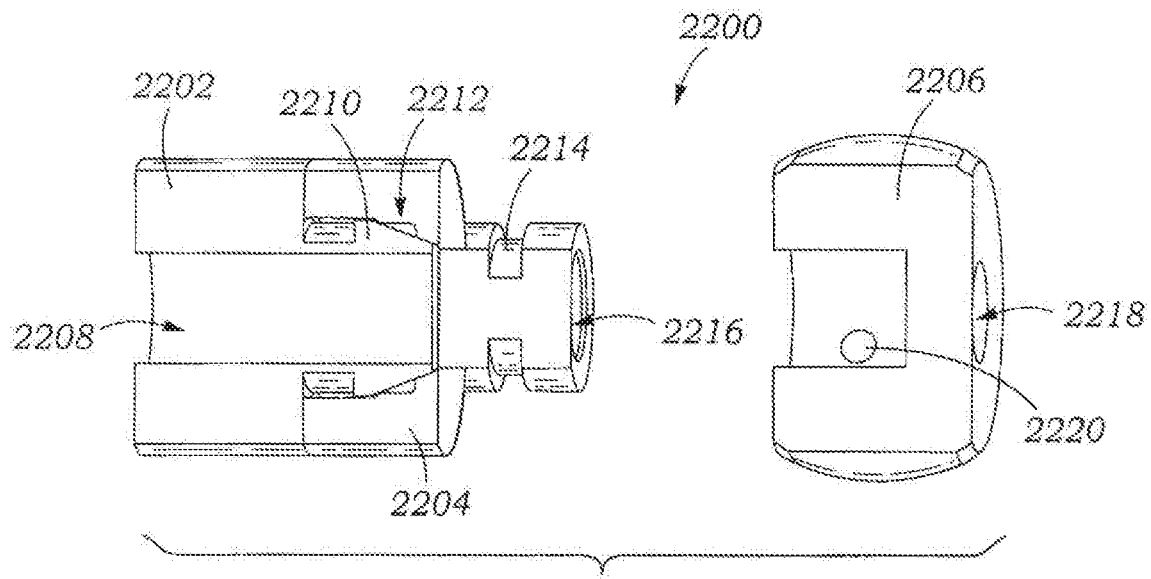
Figure 94:
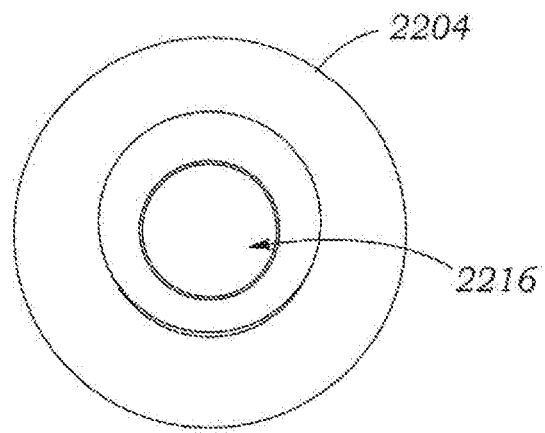
Figure 95:
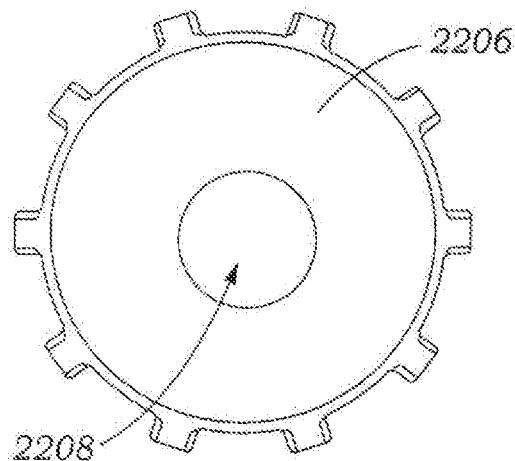

FIGS. 92-96 show an exemplary catheter-position locking device 2200, according to another embodiment. In the illustrated embodiment, the locking device 2200 comprises a shaft portion 2202, a cam portion 2204, and a handle portion 2206 comprising a rotatable knob. As best shown in FIG. 93, the shaft 2202 of the device 2000 can comprise an opening or lumen 2208 extending axially through the shaft 2202 and a flanged portion 2210 at the proximal end of the shaft 2202. FIG. 93 also shows that the shaft portion 2202 and the cam portion 2204 can be connected by inserting the flanged portion 2210 into an annular recessed portion 2212 formed in the distal end of the cam portion 2204.

The cam portion 2204 can be rotatable relative to the shaft portion 2202. The cam 2204 can further comprise an annular notch or groove 2214 disposed near the proximal end of the cam 2204 (FIGS. 92-93) and an offset opening 2216 (i.e., offset or having a different axis relative to the lumen 2208 of the shaft 2202) (best shown in FIG. 94). The handle 2206 can comprise an opening 2218 extending axially through the handle 2206. The handle portion 2206 can be disposed around and attached to the cam 2204 by inserting a fastener (not shown, e.g., a screw or bolt) through a corresponding radially extending and internally threaded port 2220 in the handle 2206. The fastener and port 2220 can be configured such that the fastener can extend through the handle 2206 and engage the cam 2204 within the groove 2214, such that the handle 2206 is fixed relative to the cam 2204. Thus, rotating the handle 2206 rotates the cam 2204.

Figure 96:
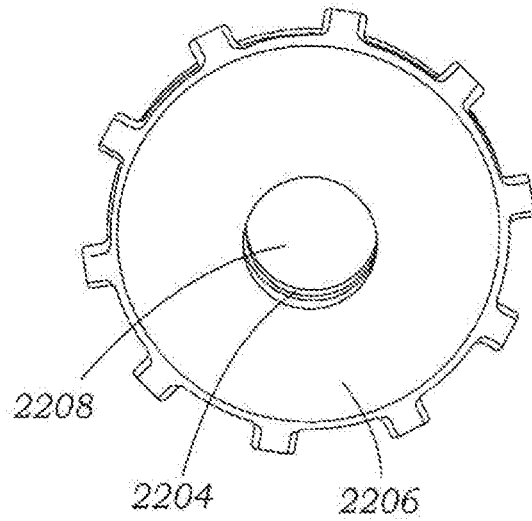

Due to the offset opening 2216, the handle 2206 and thus the cam 2204 can be rotated relative to the shaft 2202 to a first, unlocked position wherein the opening 2216 of the cam 2204 aligns with the lumen 2208 of the shaft 2202 (FIG. 95) and to a second, locked position wherein the opening 2216 of the cam 2204 misaligns with the lumen 2208 of the shaft 2202 such that the cam 2204 interferes or obstructs the lumen 2208 of the shaft 2202 (FIG. 96).

Although not shown, the device 2200 can, for example, be used with an introducer sheath and outer catheter similar to sheath 2014 and catheter 2016 in the manner shown in FIG. 87. The shaft 2202 can be fixedly secured or coupled (e.g., with an adhesive, fasteners, etc.) to the proximal end of the introducer sheath. With the opening 2216 of the cam 2204 aligned with the lumen 2208 of the shaft 2202, the outer catheter can be advanced through the device 2200 and the introducer sheath. In this aligned configuration, the outer catheter can torque/rotate and/or move axially relative to the device 2200 and the introducer sheath to a desirable positioning. Once desirably positioned, the handle 2200 can be rotated to a second, misaligned position causing the cam 2204 to press against the outer catheter, thereby preventing the outer catheter from torquing/rotating and or moving axially relative to the introducer sheath.

Figure 97:
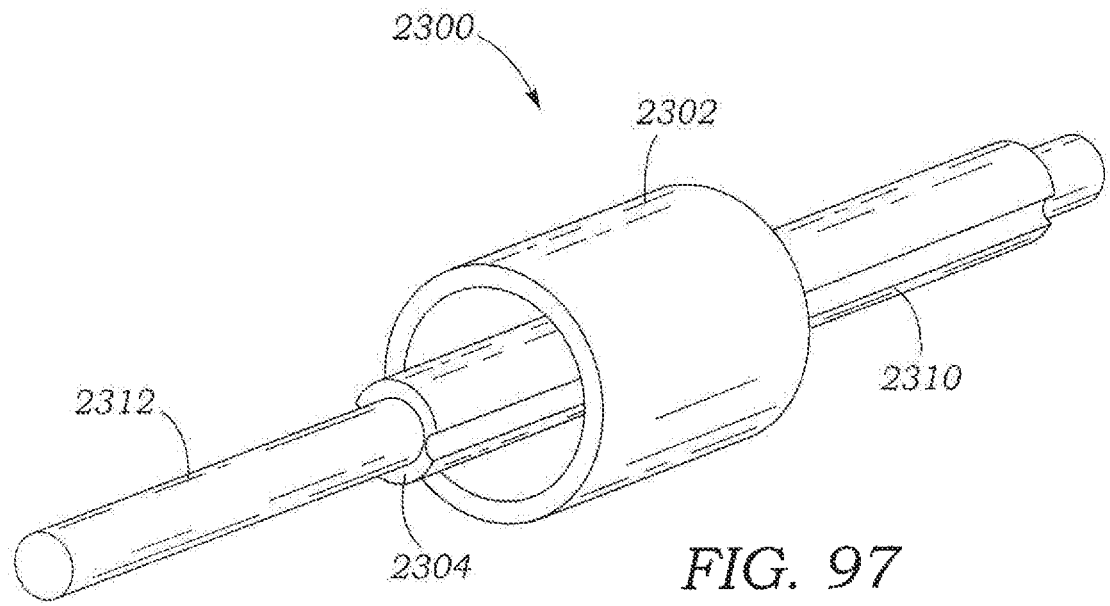
FIGS. 97-98 are perspective and end views, respectively, of another embodiment of a catheter-position locking device.
Figure 98:
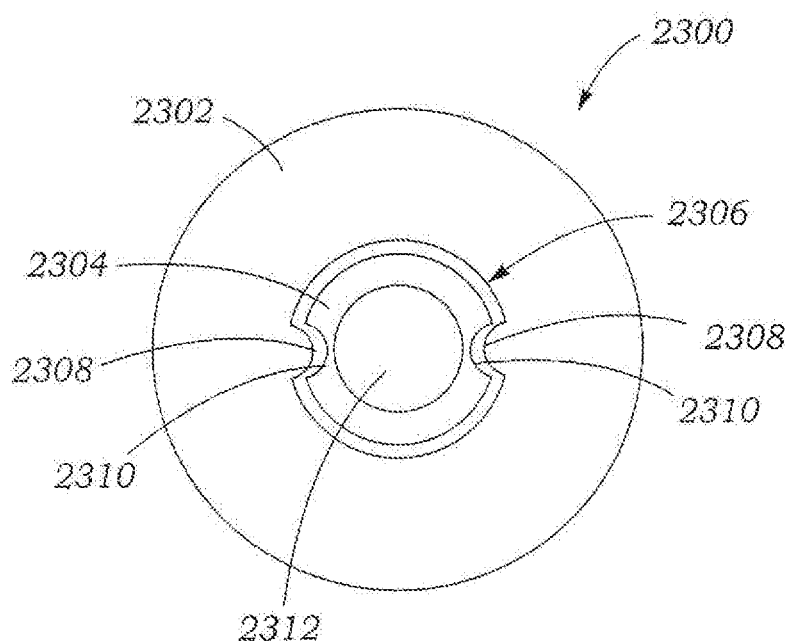

FIGS. 97-98 show an exemplary catheter-position locking device 2300, according to another embodiment. The device 2300 comprises a lock sleeve 2302 and a key shaft or tube 2304. As best shown in FIG. 98, the lock sleeve 2302 comprises an axially extending opening 2306 which includes at least one tab or pin 2308 (two in the illustrated embodiment) extending radially inward within the opening 2306. The key tube 2304 comprises at least one groove or notch 2310 (two in the illustrated embodiment). The notches 2310 of the key tube 2304 can be configured to correspond with the pins 2308 of the lock sleeve 2302 such that the key tube 2304 can be inserted and move axially within the opening of the lock sleeve 2302 by aligning the notches of the key tube 2304 with the pins 2308 of the lock sleeve 2302.

As shown, the pins 2308 of the lock sleeve 2302 and the corresponding notches 2310 of the key tube 2304 can be symmetrically disposed around the opening 2306 of the lock sleeve 2302 and the key tube 2304, respectively. When the configured symmetrically, the key tube 2304 can be inserted into the lock sleeve 2302 in multiple orientations (two orientations in the illustrated embodiment). Although not shown, it should be noted that the pins 2308 of the lock sleeve 2302 and the corresponding notches 2310 of the key tube 2304 can be asymmetrically disposed around the opening 2306 of the lock sleeve 2302 and the key tube 2304, respectively, such that the key tube 2304 can be inserted into the lock sleeve 2302 in only one orientation.

The device 2300 can, for example, be used with a prosthetic implant delivery system or device to prevent one catheter from torquing or rotating relative to another catheter. For example, the device 2300 can be used to prevent a middle or guide catheter 2312 from torquing or rotating relative to an outer catheter (not shown, but similar to outer catheter 2016), or vice versa. The lock sleeve 2302 can be fixedly secured to the proximal end of an outer catheter. For example, the distal end of the lock sleeve 2302 can be advanced over the proximal end of the outer catheter, the lock sleeve 2302 being fixedly secured to the outer catheter with an adhesive, fasteners, etc. The key tube 2304 can be fixedly secured to the shaft of the guide catheter 2312.

With the lock sleeve 2302 and key tube 2304 fixedly secured to the outer catheter and the guide catheter 2312, respectively, the guide catheter 2312 can be advanced through the outer catheter until the key tube 2304 enters the lock sleeve 2302. In this configuration, the pins 2308 of the lock sleeve 2302 engage the notches 2310 of the key tube 2304, thereby preventing the guide catheter 2312 from torquing or rotating relative to the outer catheter, or vice versa. Alternatively, in other implementations, using delivery device 1300 as an example, the key tube 2304 can be fixedly secured to and disposed on the intermediated shaft between the basket 1304 and the basket expander 1308, preferably near the basket expander 1308. In another implementation, using the delivery device 1400 as an example, the key tube 2304 can be fixedly secured to and disposed on the intermediate shaft 1404 distal to, but preferably near, the control member 1408.

By preventing the guide catheter from torquing or rotating, the delivery system can be, for example, significantly safer to use because it helps protect against inadvertent torqueing the guide catheter during a procedure. This makes a delivery device significantly easier to use because improper movement is desirably prevented or eliminated, reducing the number of steps needed to perform a procedure, as well as wasted movement. By bonding the key tube at a pre-set location and/or orientation on the shaft of the guide catheter, the device 2300 can also make the device easier to use, reduce procedure time, and/or mistakes by reducing or eliminating the need for the physician to determine how far to advance and/or orient the guide catheter relative to the outer catheter.

Figure 99:
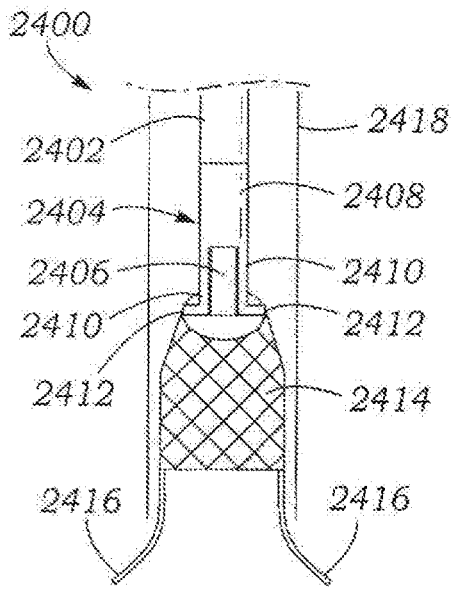
FIGS. 99-102 are various views of another embodiment of a delivery device being used to deliver a prosthetic device within the native mitral valve.
Figure 100:
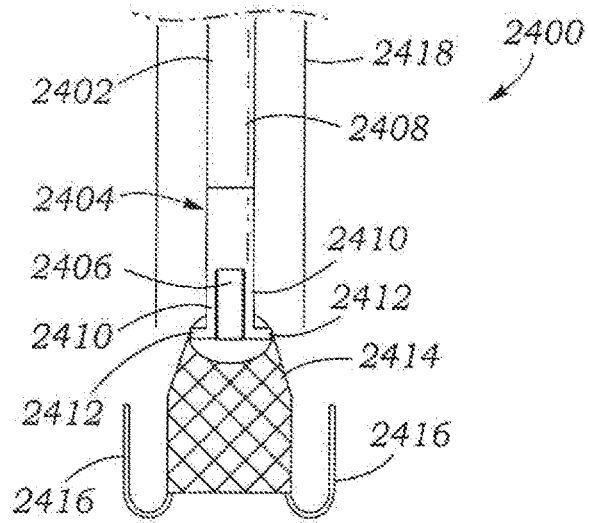

FIGS. 99-102 show an exemplary prosthetic implant delivery device 2400, according to one embodiment. The delivery device 2400 comprises an outer shaft 2402, an annular collar or collet 2404, and an inner shaft 2406, as best shown in FIGS. 99-100. The collet 2404 can be fixedly secured or coupled to the distal end of the outer shaft 2402, and the inner shaft 2406 can extend co-axially through the outer shaft 2402 and the collet 2404. The inner shaft 2406 can be axially moveable (i.e., distally or proximally) relative to the outer shaft 2402 and the collet 2404.

The collet 2404 of the delivery device 2400 can comprise a sleeve portion 2408 located at the proximal end of the collet 2404 and a plurality of prongs or tines 2410 (two in the illustrated embodiment) which extend axially away (i.e., distally) from the distal end of the sleeve portion 2408. The tines 2410 can each comprise a respective radial projection 2412, the projections 2412 being disposed at or near the distal end of the tines 2410 and extending radially outward from the tines 2410. The projections 2412 of the tines 2410 can be configured to connect to the proximal end of a prosthetic spacer device or another percutaneously delivered prosthetic device. For example, a prosthetic spacer device can have a proximally disposed annular collar (similar to collar 112) comprising a plurality of radial openings configured to receive the projections 2412 of the delivery device 2400, thereby connecting the prosthetic spacer to the delivery device 2400.

The collet 2404 of the delivery device 2400 can be formed from a material that allows the tines 2410 to be elastically expandable and compressible in the radial direction. For example, the collet 2404 can be formed from stainless steel. When formed from an elastically expandable and compressible material, the tines 2410 can radially expand from a released configuration (FIGS. 101-102) to an attached or delivery configuration (FIG. 99-100) and vice versa, as further described below.

The delivery device 2400 can be used to deliver a prosthetic spacer device 2414 percutaneously to a native heart valve (e.g., the mitral valve), as shown in FIGS. 99-102. The prosthetic spacer 2414 can include anchors 2416. The delivery device 2400 can, for example, be used as part of a delivery apparatus including an outer catheter (not shown, but similar to outer catheter 212), middle or guide catheter (not fully shown, but similar to guide catheters 1300, 1400), and the delivery device 2400.

The outer catheter can, for example, be used to cross the septal wall, the outer catheter opening into the left atrium of the heart. The middle or guide catheter comprising an implant cover or sheath 2418 can, for example, be advanced through the outer catheter with the delivery catheter 2400 and into the mitral valve such that the anchors 2416 are in the left ventricle, as shown in FIG. 99. The spacer 2414 can then be deployed from within the sheath 2418 by advancing the delivery catheter 2400 distally, relative to the sheath 2418, or retracting the sheath proximally relative to the delivery catheter, as shown in FIG. 100. The delivery device 2400 can be used to desirably position the spacer 2414 relative to the native leaflets 2420. For example, the spacer 2414 can be torqued or rotated and/or moved axially by rotating or torquing and/or advancing or retracting the outer shaft 2402, respectively.

Figure 101:
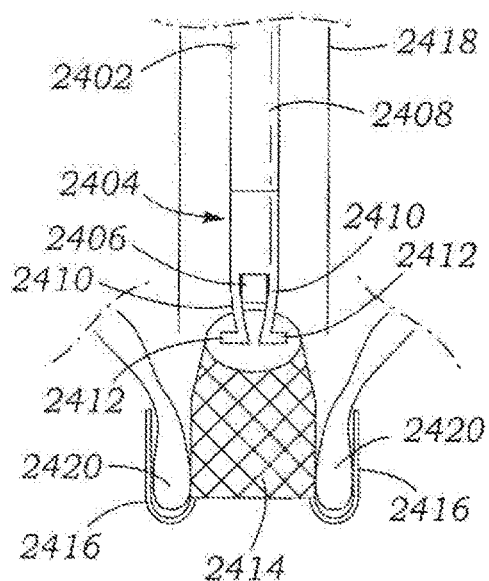
Figure 102:
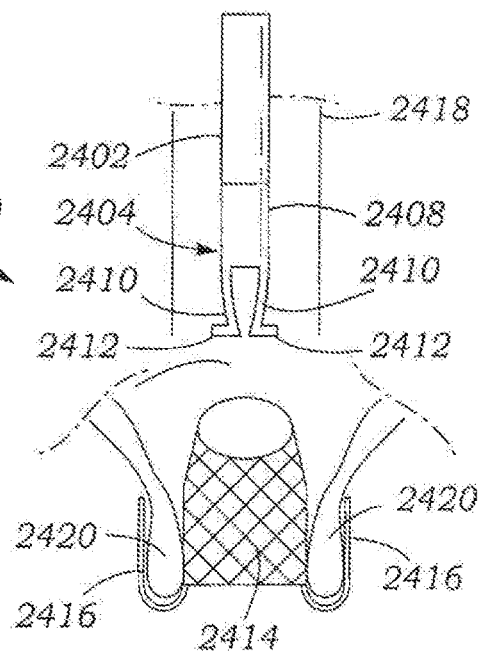

Once the spacer 2414 is desirable positioned and secured to the native leaflets, the spacer 2414 can be released from the delivery device 2400. The spacer 2414 can be released from the delivery device 2400 by retracting the inner shaft 2406, relative to the collet 2404 and the outer shaft 2402, allowing the tines 2410 to radially compress and the projections 2412 to move radially inward away from the spacer 2414 such that the projections 2412 disengage the spacer 2414, as shown in FIG. 101. With the projections 2412 disconnected from the spacer 2414, the spacer 2414 is released, and the delivery device 2400 and the sheath 2418 can be retracted through the outer catheter, as shown in FIG. 102.

If, however, the physician would like to reposition the spacer 2414 after releasing the delivery device 2400, the physician can re-attach the delivery device 2400 to the spacer 2414 by reversing the above-described steps for releasing the spacer 2414.

Figure 103:
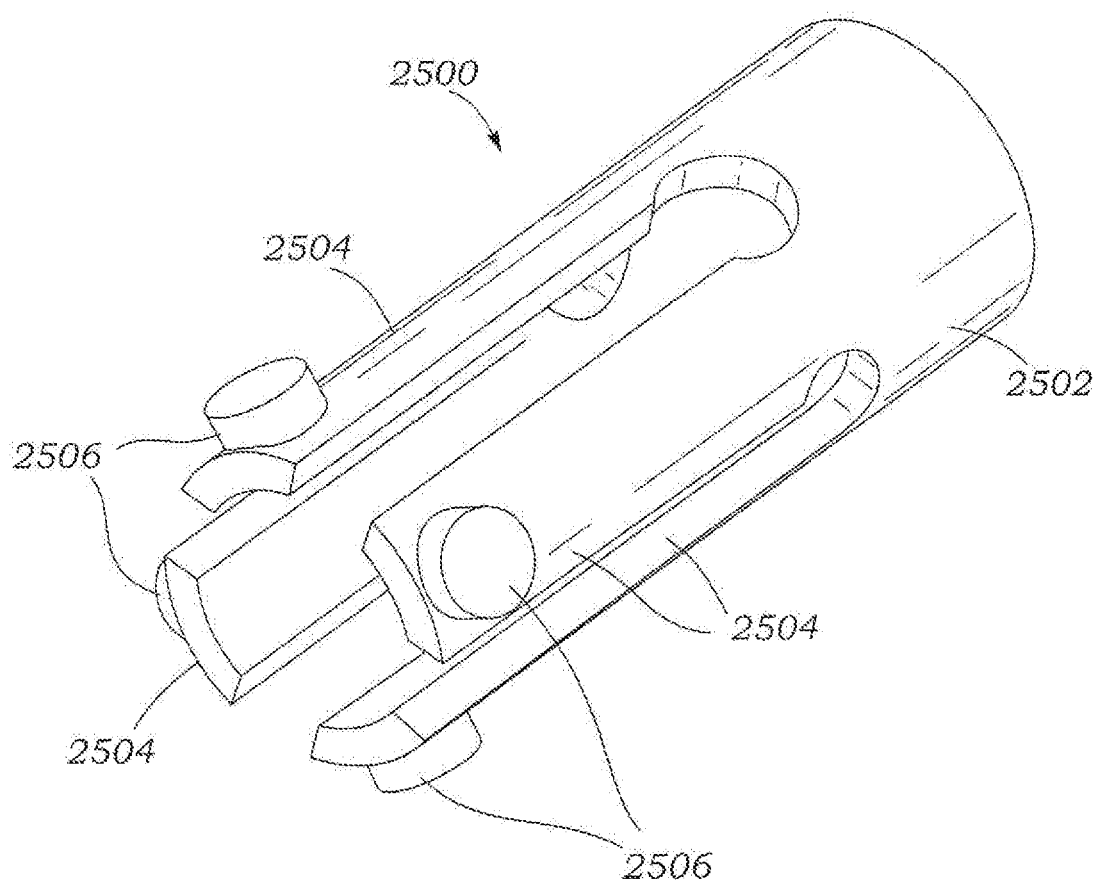
FIG. 103 is a perspective view of an exemplary collet/prosthetic-device-retaining-mechanism that can be incorporated in the delivery device of FIGS. 99-102.

FIG. 103 shows an exemplary embodiment of an annular collar or collet 2500 for a delivery catheter which is similar to collet 2404 of the delivery device 2400. The collet 2500 can comprise a sleeve 2502 and a plurality of tines 2504 (four in the illustrated embodiment) extending axially away from the distal portion of the sleeve 2502. As shown, each tine 2504 can comprise a projection 2506 extending radially outward from the distal end of a respective tine 2504. Each projection is configured to extend into a respective opening of the implant to be delivered. The collet 2500 can function and be used in a manner substantially similar to collet 2404 of delivery device 2400.

Figure 104:
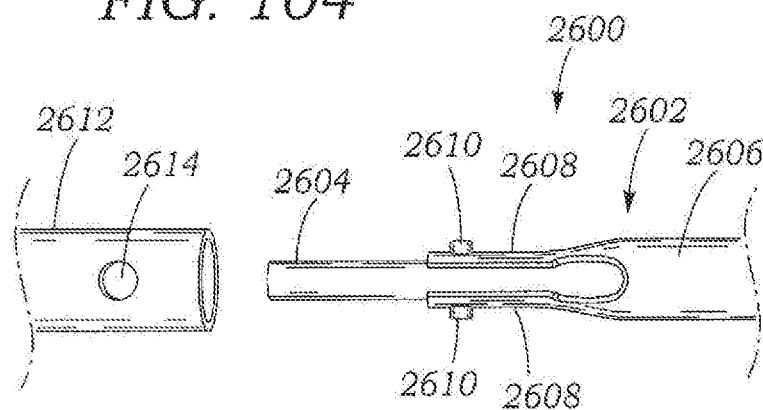
FIGS. 104-106 show various views of a prosthetic device being connected to a delivery device for delivery into a patient.
Figure 105:
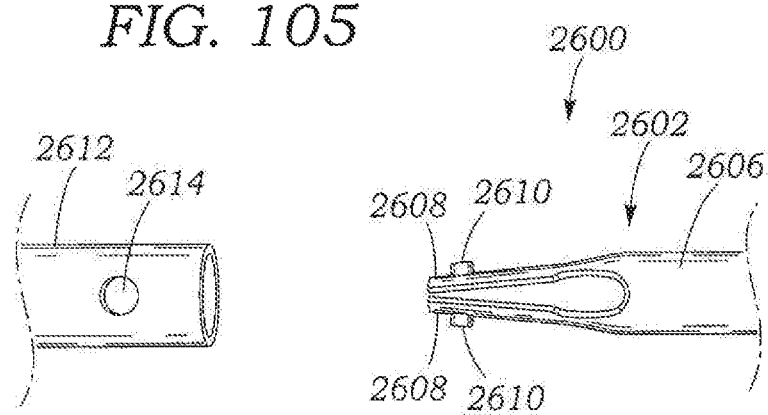
Figure 106:
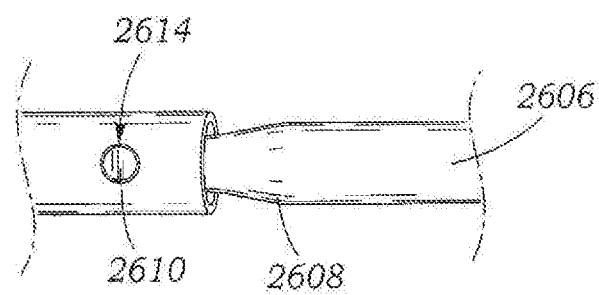

FIGS. 104-106 show another exemplary embodiment of a prosthetic implant delivery device 2600, similar to delivery device 2400. The delivery device 2600 comprises an outer shaft (not shown, but similar to outer shaft 2402), an annular collar or collet 2602, and an inner shaft 2604, as best shown in FIG. 104. The collet 2602 can be fixedly secured or coupled to the distal end of the outer shaft, and the inner shaft 2604 can extend co-axially through the outer shaft and the collet 2602. The inner shaft 2604 can be axially moveable (i.e., distally or proximally) relative to the outer shaft 2402 and the collet 2404.

The collet 2602 of the delivery device 2600 can comprise a sleeve portion 2606 located at the proximal end of the collet 2602 and a plurality of prongs or tines 2608 (two in the illustrated embodiment) which extend axially away (i.e., distally) from the distal end of the sleeve portion 2606. The tines 2608 can each comprise a respective projection 2610, the projections 2610 being disposed at or near the distal end of the tines 2608 and extending radially outward from the tines 2608. The projections 2610 of the tines 2608 can be configured to connect to the proximal end of a prosthetic implant device (e.g., a prosthetic spacer). For example, a prosthetic spacer device can have a proximally disposed annular collar 2612 comprising a plurality of radial openings 2614 configured to receive the projections 2610 of the delivery device 2600.

Similar to delivery device 2400, the delivery device 2600 can be coupled to the collar 2612 of a prosthetic implant by retracting the inner shaft 2604 proximally, relative to the collet 2602 and the outer shaft (not shown), such that the distal end of the inner shaft 2604 is located proximal within the sleeve 2606 of the collet 2602, as shown in FIG. 105. Retracting the inner shaft 2604 allows the tines 2608 to radially compress (see FIG. 105) such that the tines 2608 can be inserted into the collar 2612 of the prosthetic implant.

As shown in FIG. 106, the implant can be secured to the delivery device 2600 by aligning the projections 2610 of the delivery device 2600 with the openings 2614 of the implant and advancing the inner shaft 2604 distally, relative to the collet 2602 and the outer shaft (not shown), such that the inner shaft 2604 extends axially through the tines 2608. Advancing the inner shaft 2604 through the tines 2608 causes the tines 2608 to radially expand and forces the projections 2610 into the openings 2612 of the implant, thus securing the implant to the delivery device 2600.

Figure 107:
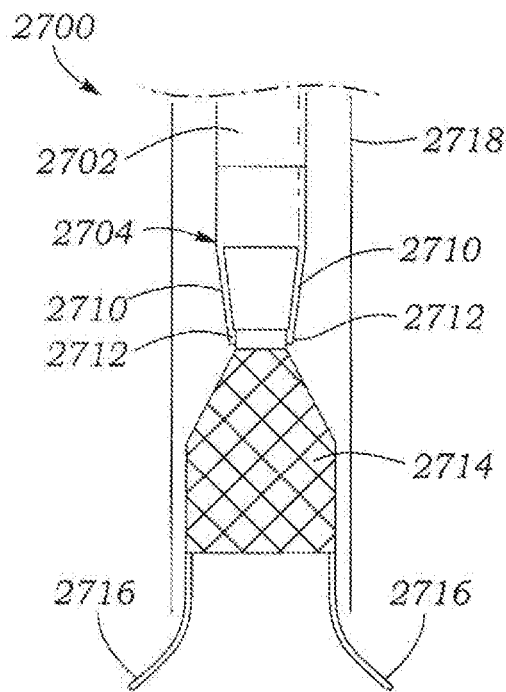
FIGS. 107-110 are various views of another embodiment of a delivery device being used to deliver a prosthetic device within the native mitral valve.
Figure 108:
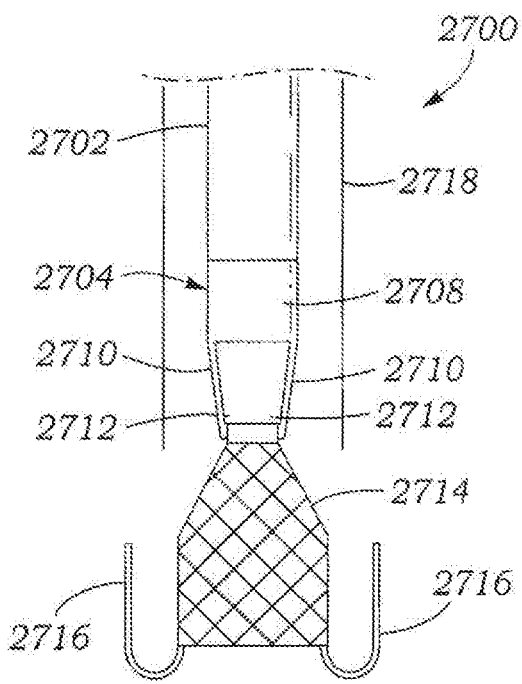
Figure 109:
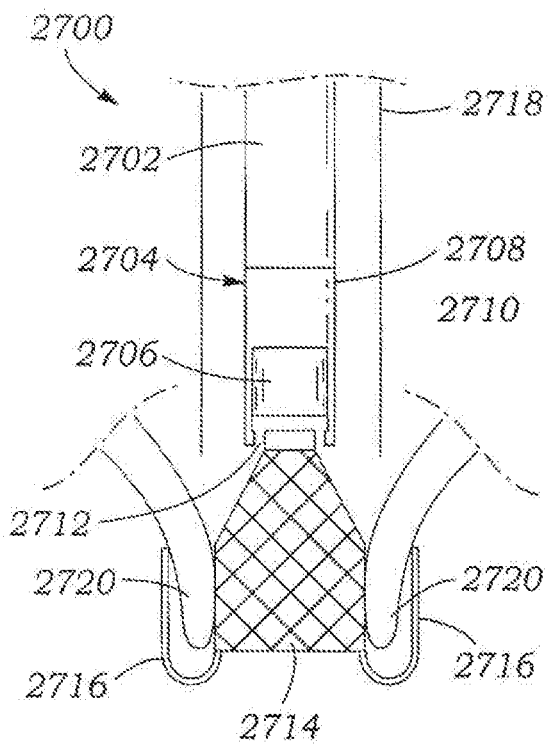
Figure 110:
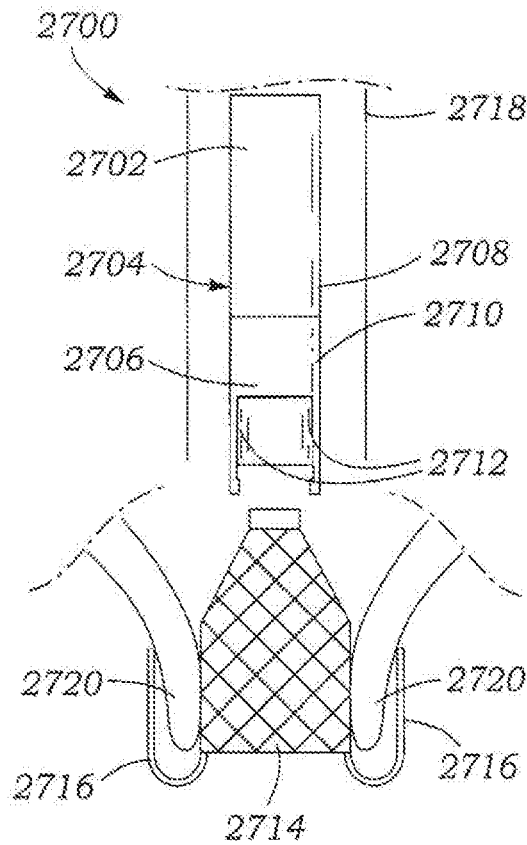

FIGS. 107-110 show an exemplary prosthetic implant delivery device 2700, similar to delivery device 2400, according to one embodiment. The delivery device 2700 comprises an outer shaft 2702, an annular collar or collet 2704, and an inner shaft 2706, as best shown in FIGS. 109-110. The collet 2704 can be fixedly secured or coupled to the distal end of the outer shaft 2702, and the inner shaft 2706 can extend co-axially through the outer shaft 2702 and the collet 2704. The inner shaft 2706 can be axially moveable (i.e., distally or proximally) relative to the outer shaft 2702 and the collet 2704.

The collet 2704 of the delivery device 2700 can comprise a sleeve portion 2708 located at the proximal end of the collet 2704 and a plurality of prongs or tines 2710 (two in the illustrated embodiment) which extend axially away (i.e., distally) from the distal end of the sleeve portion 2708. The tines 2710 can each comprise a respective projection 2712, the projections 2712 being disposed at or near the distal end of the tines 2710 and extending radially inwardly from the tines 2710. The projections 2712 of the tines 2710 can be configured to connect to the proximal end of a prosthetic spacer device. For example, a prosthetic spacer device can have a proximally disposed annular collar (similar to collar 112) comprising a plurality of radial openings configured to receive the projections 2712 of the delivery device 2700, thereby connecting the prosthetic spacer to the delivery device 2700.

The collet 2704 of the delivery device 2700 can be formed from a material that allows the tines 2710 to be elastically expandable and compressible in the radial direction. For example, the collet 2704 can be formed from stainless steel. When formed from an elastically expandable and compressible material, the tines 2710 can radially expand from an attached, delivery configuration (FIGS. 107-108) to a released configuration (FIG. 109-110) and vice versa, as further described below.

The delivery device 2700 can be used to deliver a prosthetic spacer device 2714 percutaneously to a native heart valve (e.g., the mitral valve), as shown in FIGS. 107-110. The prosthetic spacer 2714 can include anchors 2716 and an annular collar 2718. The delivery device 2700 can, for example, be used as part of a delivery apparatus including an outer catheter (not shown, but similar to outer catheter 212), middle or guide catheter (not fully shown, but similar to guide catheters 1300, 1400), and the delivery device 2700.

The outer catheter can, for example, be used to cross the septal wall, the outer catheter opening into the left atrium of the heart. The middle or guide catheter comprising an implant cover or sheath 2718 can, for example, be advanced through the outer catheter with the delivery catheter 2700 and into the mitral valve such that the anchors 2716 are in the left ventricle, as shown in FIG. 107. The spacer 2714 can then be deployed from within the sheath 2718 by advancing the delivery catheter 2700 distally, relative to the sheath 2718, or retracting the sheath proximally relative to the delivery catheter, as shown in FIG. 108. The delivery device 2700 can be used to desirably position the spacer 2714 relative to the native leaflets 2720. For example, the spacer 2714 can be torqued or rotated and/or moved axially by rotating or torquing and/or advancing or retracting the outer shaft 2702, respectively.

Once the spacer 2714 is desirable positioned and secured to the native leaflets, the spacer 2714 can be released from the delivery device 2700. The spacer 2714 can be released from the delivery device 2700 by advancing the inner shaft 2706 distally relative to the collet 2704 and the outer shaft 2702, causing the tines 2710 to radially expand and the projections 2712 to move radially outwardly away from the spacer 2714 such that the projections 2712 disengage from the spacer 2714, as shown in FIG. 109. With the projections 2712 disconnected from the spacer 2714, the spacer 2714 is released, and the delivery device 2700 and the sheath 2718 can be retracted through the outer catheter, as shown in FIG. 110.

If, however, the physician would like to reposition the spacer 2714 after releasing the delivery device 2700, the physician can re-attach the delivery device 2700 to the spacer 2714 by reversing the above-described steps for releasing the spacer 2714.

Figure 111:
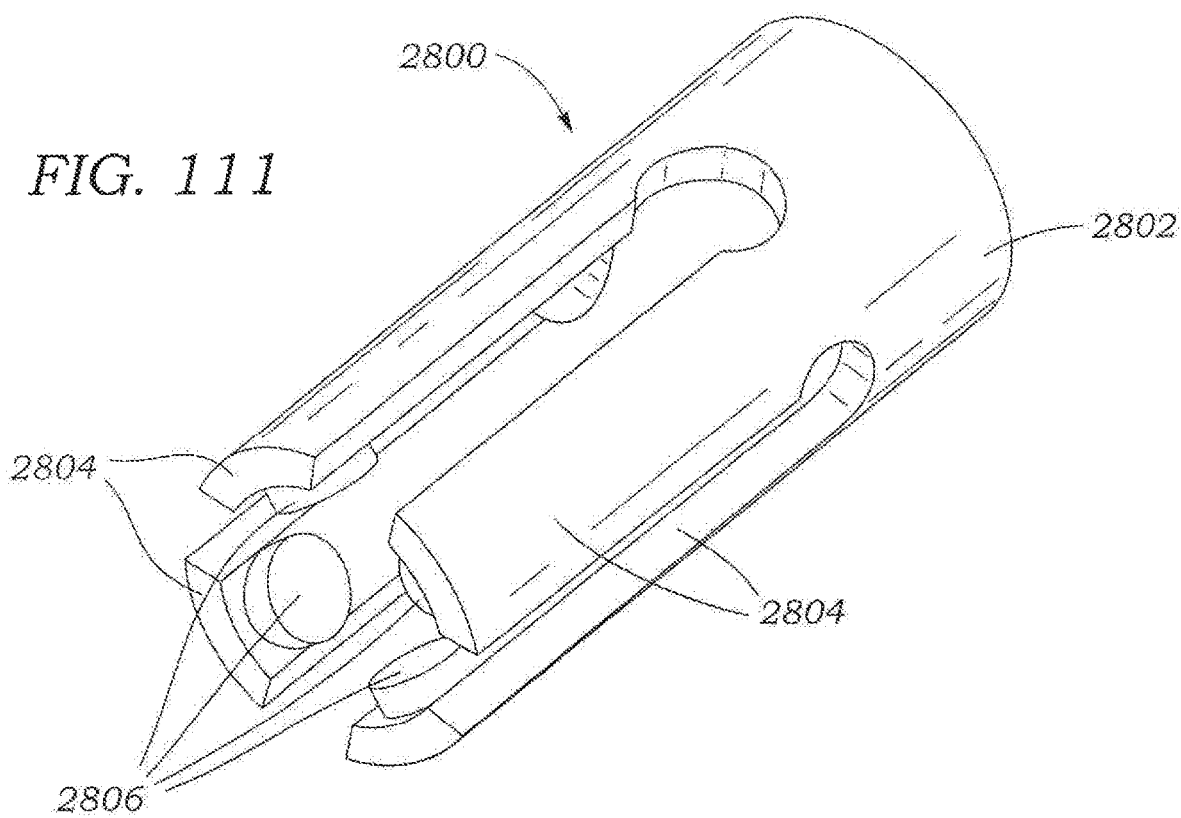
FIG. 111 is a perspective view of an exemplary collet/prosthetic-device-retaining-mechanism that can be incorporated in the delivery device of FIGS. 107-110.

FIG. 111 shows an exemplary embodiment of an annular collar or collet 2800 which is similar to collet 2704 of the delivery device 2700. The collet 2800 can comprise a sleeve 2802 and a plurality of tines 2804 (four in the illustrated embodiment) extending axially away from the distal portion of the sleeve 2802. As shown, each tine 2804 can comprise a projection 2806 extending radially inward from the distal end of a respective tine 2804. The collet 2800 can function and be used in a manner substantially similar to collet 2704 of delivery device 2700.

Figure 112:
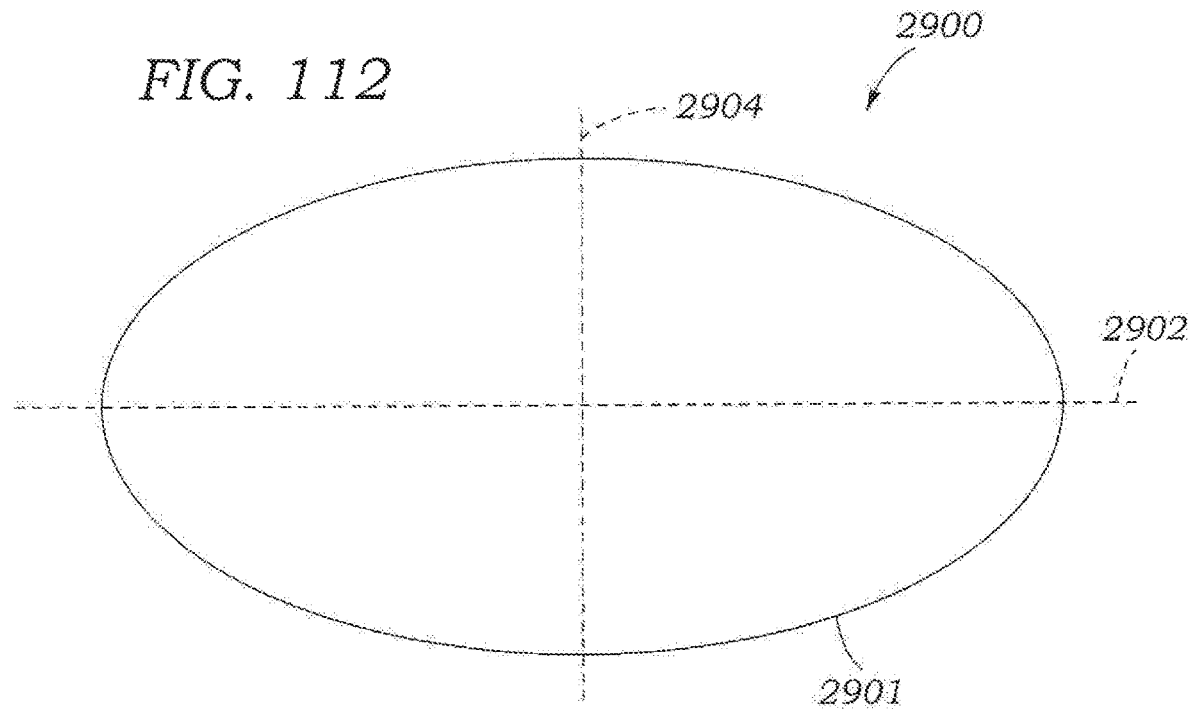
FIG. 112 is a cross-sectional view of an exemplary embodiment of a non-circular shaft of a delivery device.

FIG. 112 shows a cross-sectional view of an exemplary non-circular shaft 2901 of a delivery device 2900, according to one embodiment. As shown, the shaft 2901 can comprise a non-circular cross-sectional profile in a plane perpendicular to the longitudinal axis of the shaft. For example, the shaft 2901 comprises an elliptically-shaped cross-sectional profile, including a major axis (represented by dashed-line 2902) and a minor axis (represented by dashed-line 2904). Due to the elliptical cross-sectional shape, the delivery system 2900 can, for example, flex more easily around the major axis 2902 than the minor axis 2904. In this manner, the delivery device 2900 can be advanced through a tortuous pathway (e.g., vasculature) by rotating the catheter as needed at each successive bend in the pathway such that the major axis is generally perpendicular to the direction of the bend in the pathway.

Figure 113:
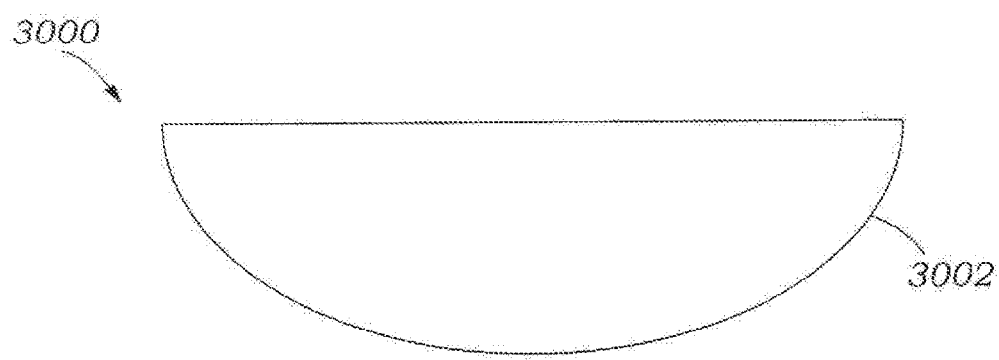
FIG. 113 is a cross-sectional view of another exemplary embodiment of a non-circular shaft of a delivery device.

FIG. 113 shows a cross-sectional view of an exemplary non-circular delivery device 3000, according to another embodiment. As shown, the delivery device 3000 can comprise a shaft 3002 comprising a "D"-shaped cross-sectional profile.

Using a non-circular delivery device (e.g., devices 2900, 3000) with a non-circular prosthetic device (a prosthetic device having a non-circular cross-sectional profile in a plane perpendicular to the longitudinal axis of the prosthetic device) can advantageously, for example, allow for more controlled deployment due to more uniform deployment forces. For example, pairing an elliptically-shaped prosthesis with an elliptically-shaped delivery system allows the deployment forces to be more uniform in the radial direction with respect to the circumference of the prosthesis. This uniformity can, for example, provide more predictability and thus control during a deployment procedure.

It should be noted that the delivery devices 2900, 3000 can, for example, comprise a non-circular catheter and/or a non-circular delivery sheath. It should also be noted that delivery devices 2900, 3000 can be used, for example, with both circular and non-circular implantable prosthetic devices.

FIGS. 114-127F show various embodiments of implantable prosthetic devices that have supplemental anchoring members to enhance the engagement of the anchors of the device against native leaflets.

Figure 114:
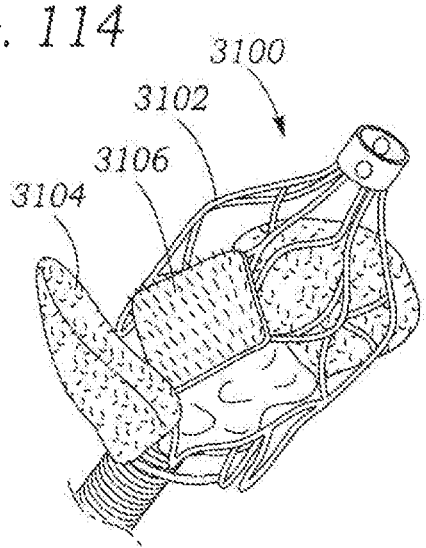
FIG. 114 shows another exemplary embodiment of an implantable prosthetic device.

FIG. 114 shows a prosthetic device 3100 comprising an annular main body 3102 and anchors 3104 extending from the main body. Pieces of friction-enhancing material 3106 can be mounted on the outside of the main body 3102 at locations opposite the anchors 3104. In particular embodiments, the friction-enhancing material 3106 can comprise, for example, the plastic hook material of a hook-and-loop fastener (e.g., Velcro®). When implanted within a native valve, the anchors 3104 can compress the native leaflets against the friction-enhancing material 3106, enhancing the retention force of the anchors. In the illustrated embodiment, the friction-enhancing material 3106 is shown mounted (e.g., with sutures) directly to the frame of the main body. In particular embodiments, the main body can be covered with a blood-impermeable cover (e.g., a fabric) and the friction-enhancing material 3106 can be mounted on the outside of the cover.

Figure 115:
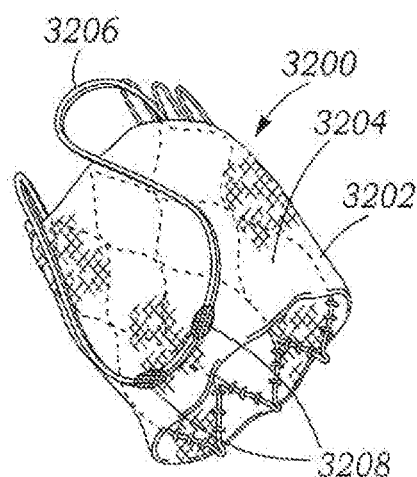
FIG. 115 shows another exemplary embodiment of an implantable prosthetic device.

FIG. 115 shows a prosthetic device 3200 comprising an annular main body 3202, a fabric cover 3204, and anchors 3104 extending from the main body. Mounted on each anchor 3206 can be one or more projections 3208 formed of suture material wrapped around the anchor, glue or other adhesive applied to the anchor, or a bead or ball of polymeric material molded or otherwise secured to the anchor. When implanted within a native valve, the anchors 3206 can urge the projections 3208 against the native leaflets, enhancing the retention force of the anchors.

Figure 116:
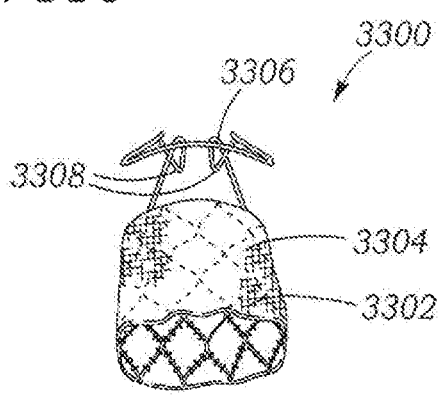
FIG. 116 shows another exemplary embodiment of an implantable prosthetic device.

FIG. 116 shows a prosthetic device 3300 comprising an annular main body 3302, a fabric cover 3304, and anchors 3306 extending from the main body. Mounted on each anchor 3306 can be one or more projections 3308 formed of metal wire secured to the ends of the anchor. When implanted within a native valve, the anchors 3306 can urge the projections 3308 against the native leaflets 3308, enhancing the retention force of the anchors.

Figure 117:
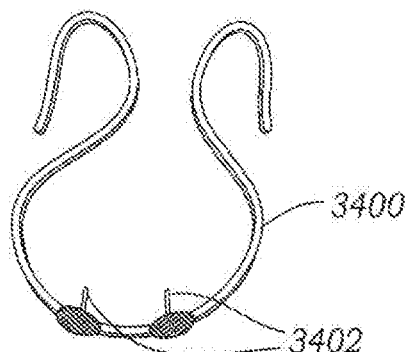
FIG. 117 shows an exemplary embodiment of an anchor that can be incorporated in an implantable prosthetic device.

FIG. 117 shows an exemplary anchor 3400 that can be secured to the main body of a prosthetic device (any of the prosthetic devices disclosed herein). The anchor 3400 can comprise one or more barbs or projections 3402 that can engage, and optionally penetrate a leaflet when implanted, enhancing the retention force of the anchor.

Figure 118:
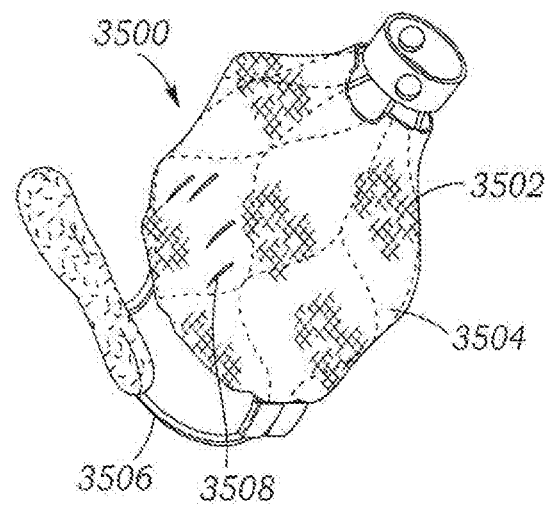
FIG. 118 shows another exemplary embodiment of an implantable prosthetic device.

FIG. 118 shows a prosthetic device 3500 comprising an annular main body 3502, a fabric cover 3504, and anchors 3506 extending from the main body. Mounted on the frame of the main body can be one or more barbs or projections 3508 that extend through the cover 3504. When implanted within a native valve, the anchors 3506 can compress the native leaflets against the projections 3508 (which can optionally penetrate the leaflets), enhancing the retention force of the anchors.

FIGS. 119A-119F show a prosthetic device 3600 comprising an annular main body 3602, a fabric cover (not shown), and anchors 3604 extending from the main body. The ends of each anchor 3604 can be coupled to respective struts of the main body 3602 by respective sleeves 3606 that can be crimped around the end portions of the anchor and the struts of the main body. Mounted on the frame of the main body can be one or more barbs or projections 3608. The free ends of the projections 3608 in the illustrated embodiment are configured to reside generally within the main body and do not necessarily extend through the fabric cover (as is shown in FIG. 118). Nonetheless, the projections 3608 can exert a retaining force against the native leaflets by virtue of the anchors 3604, which are shaped to force the native leaflets inwardly into the main body in the area below the free ends of the anchors 3604 when the anchors are moved from an open position (FIGS. 119E and 119F) to a closed position (FIGS. 119A-119D).

Figure 120A:
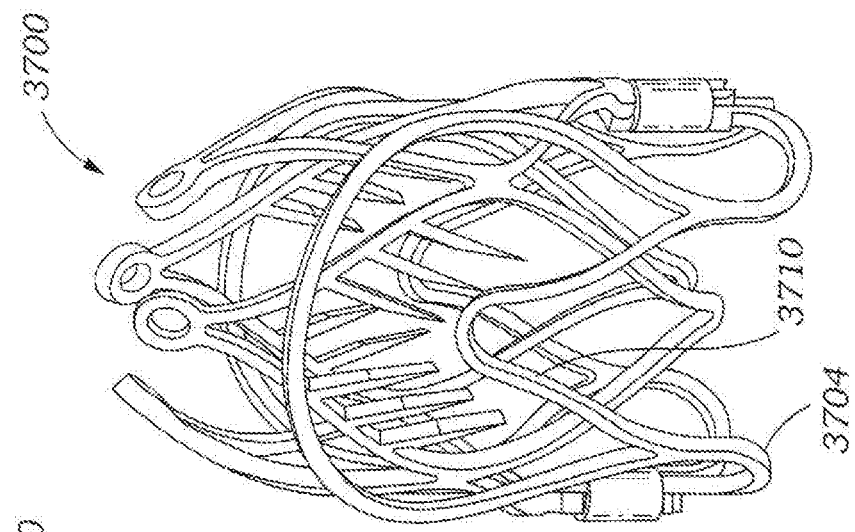
FIGS. 120A-120C show another exemplary embodiment of an implantable prosthetic device.
Figure 120B:
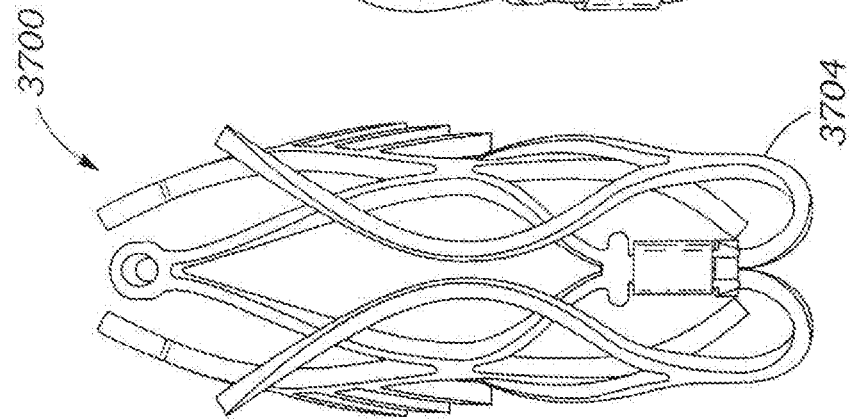
Figure 120C:
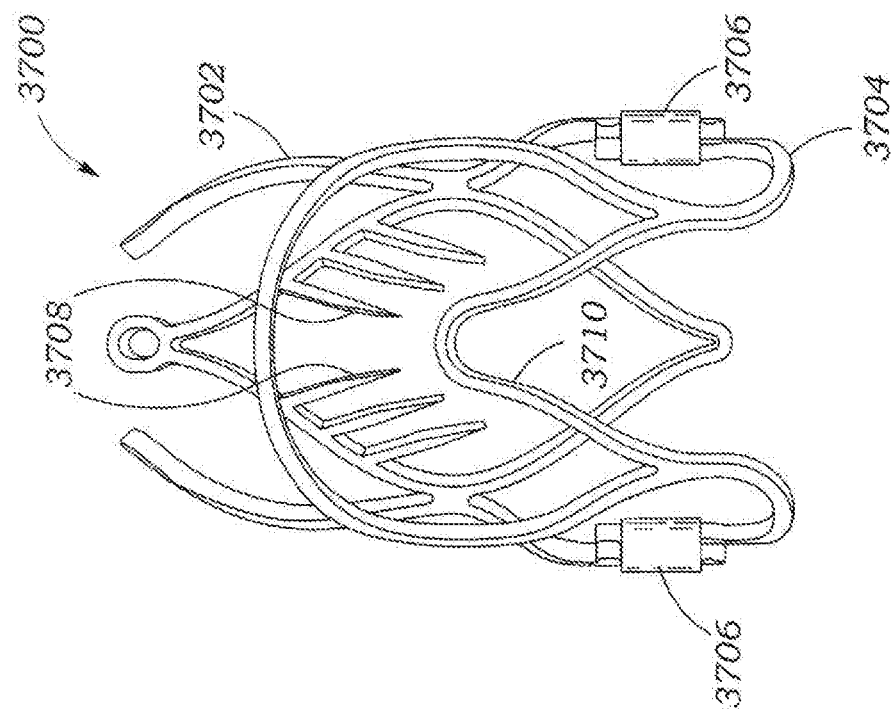
Figure 122B:
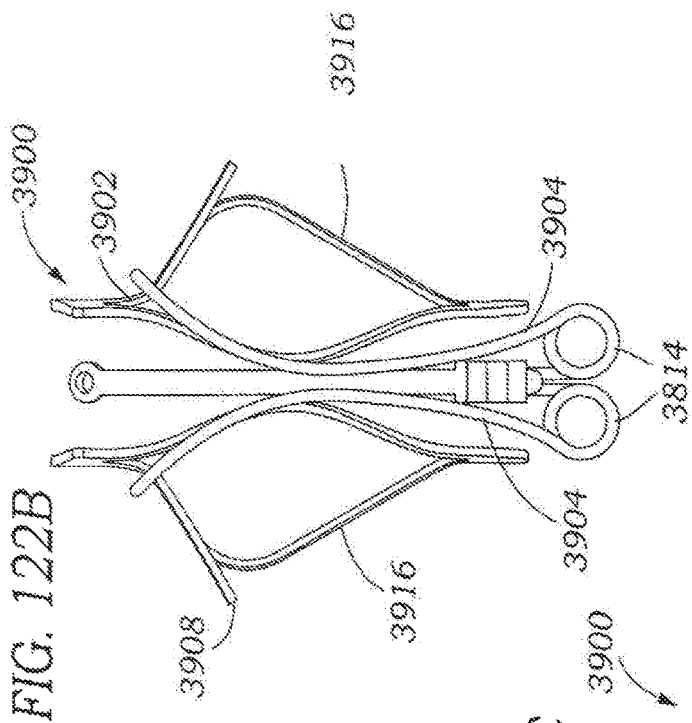
FIGS. 122A-122D show another exemplary embodiment of an implantable prosthetic device.
Figure 122D:
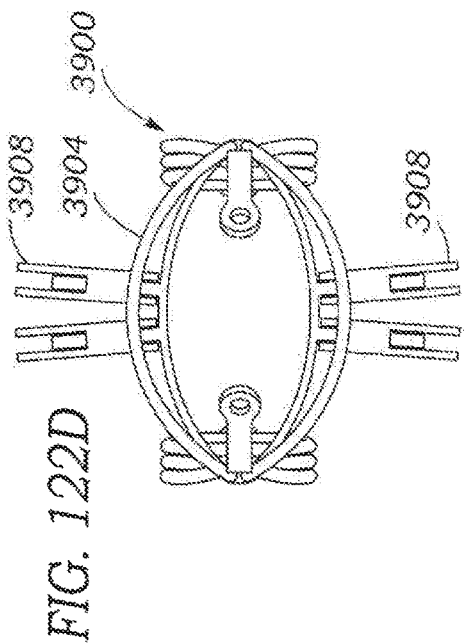
Figure 122C:
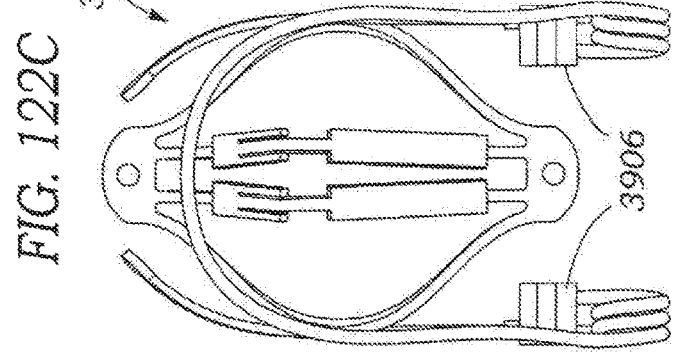
Figure 122A:
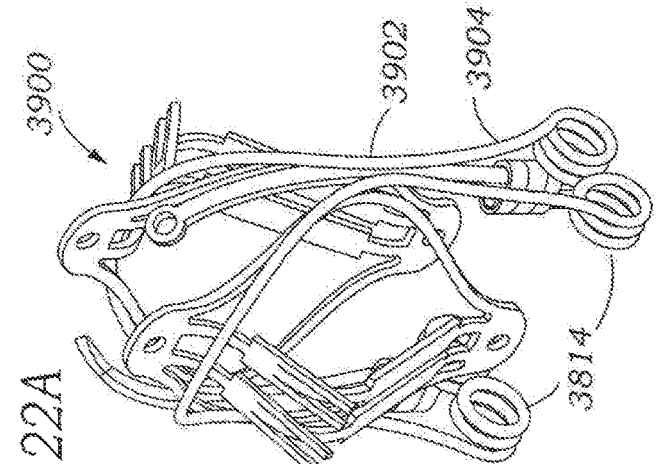
Figure 123C:
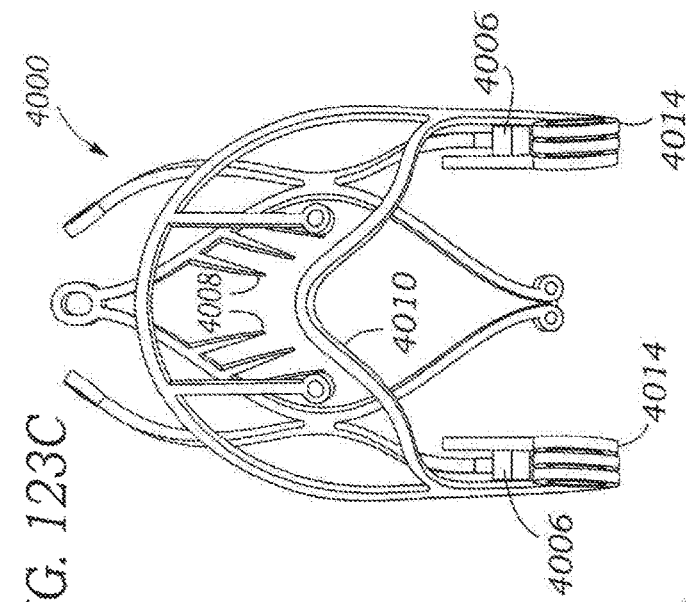
FIGS. 123A-123D show another exemplary embodiment of an implantable prosthetic device.
Figure 123D:
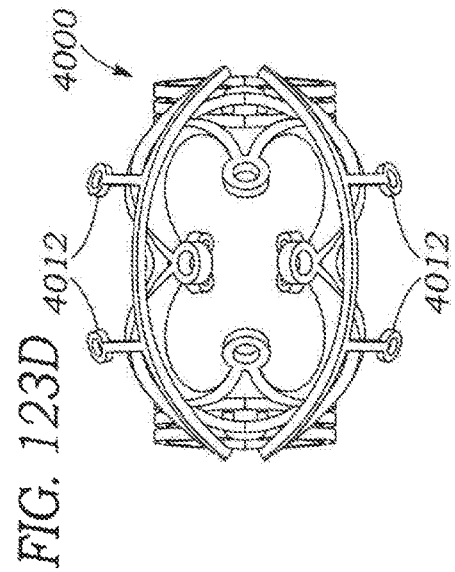
Figure 123B:
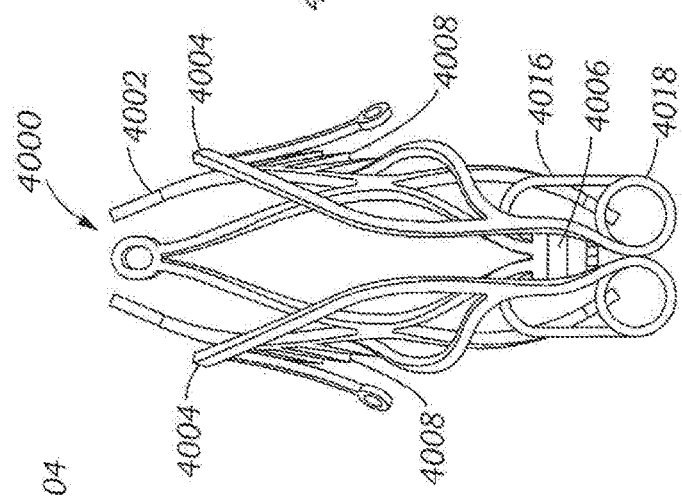
Figure 123A:
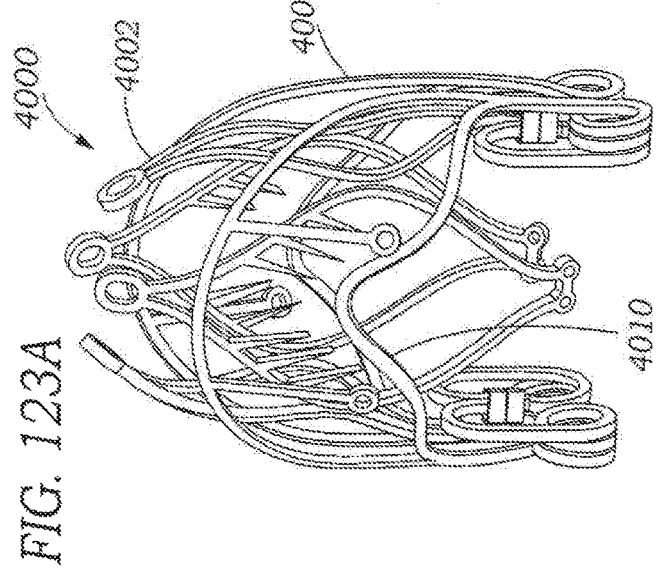
Figure 124E:
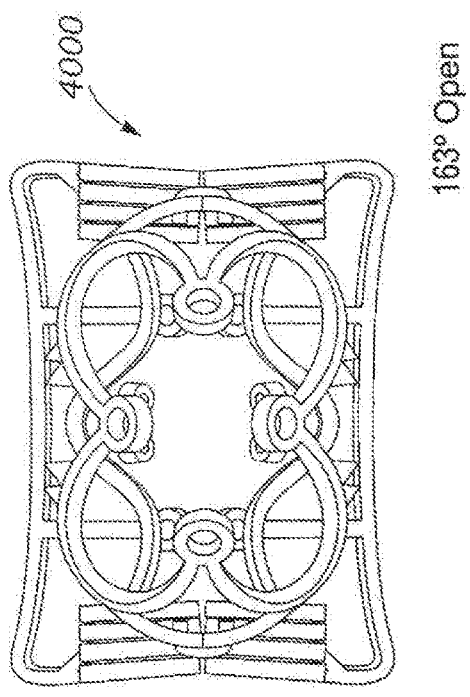
Figure 124F:
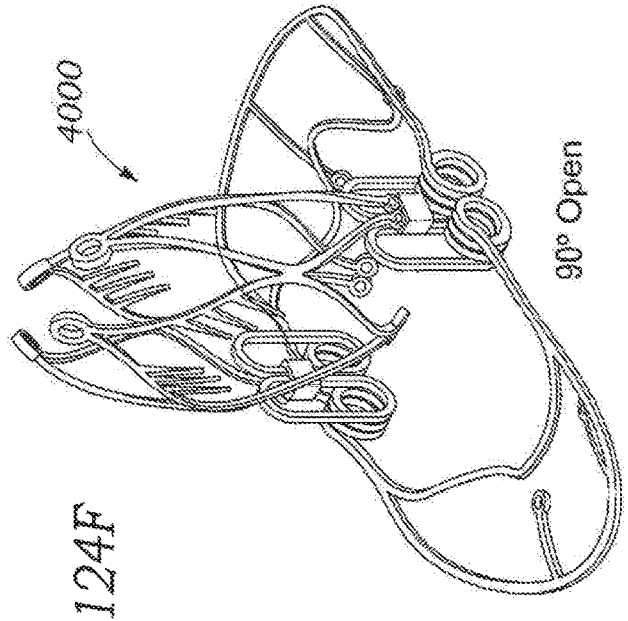

FIGS. 120A-120C show a prosthetic device 3700 comprising an annular main body 3702, a fabric cover (not shown), anchors 3704 extending from the main body, sleeves 3706 coupling the anchors to the main body, and projections 3708 extending from the main body. The device 3700 is similar to device 3600 except that the anchors 3704 comprise intermediate portions 3710 that are shaped to extend inwardly into the area below the projections 3708 when the anchors are in the closed position, as shown in the figures. In this manner, the intermediate portions 3710 assist in pushing the native leaflets inwardly against the projections 3710, thereby enhancing the engagement of the device within the native leaflets.

FIGS. 121A-121D show a prosthetic device 3800 comprising an annular main body 3802, a fabric cover (not shown), anchors 3804 extending from the main body, sleeves 3806 coupling the anchors to the main body, and projections 3808 extending from the main body. The anchors 3804 comprise intermediate portions 3810 that press the native leaflets inwardly against the projections 3808 and outwardly extending projections 3812 that press the native leaflets against the main body in the area above the projections. The opposing lower legs of the anchors 3804 in the illustrated embodiment comprise coil springs 3814 that function as spring hinges that allow the anchors to be splayed apart from the main body yet provide a spring force that biases the anchors against the body when the opening force is removed from the anchors.

FIGS. 122A-122D show a prosthetic device 3900 comprising an annular main body 3902, a fabric cover (not shown), anchors 3904 extending from the main body, sleeves 3906 coupling the anchors to the main body, and projections 3908 extending from the main body. Similar to device 3800, the lower legs of the anchors 3904 can comprise coil springs 3814 that function as spring hinges for opening and closing the anchors. Unlike previous embodiments, the projections 3908 extend radially outwardly and downwardly toward the ventricular end of the main body and are mounted on outwardly curved strut members 3916 of the main body that protrude outwardly through the anchors 3908 when pivoted to the closed position.

FIGS. 123A-123D show a prosthetic device 4000 comprising an annular main body 4002, a fabric cover (not shown), anchors 4004 extending from the main body, sleeves 4006 coupling the anchors to the main body, and projections 4008 extending from the main body. The anchors 4004 comprise intermediate portions 4010 that press the native leaflets inwardly against the projections 4008 and outwardly extending projections 4012 that press the native leaflets against the main body in the area above the projections. The opposing lower legs of the anchors 4004 in the illustrated embodiment comprise coil springs 4014 that function as spring hinges for opening and closing the anchors. The device 4000 is similar to the device 3800 except that each of the springs 4014 has a respective end portion 4016 that extends upwardly from a coil portion 4018 and curves back downwardly where it is connected to a strut of the main body by one or more sleeves 4006. FIGS. 124A-124F are various views the device 4000 showing the anchors in the closed position (FIG. 124A), in the fully open position (FIG. 124D), and various partially opened positions (FIGS. 124B-124C, 124E, and 124F).

Figure 125B:
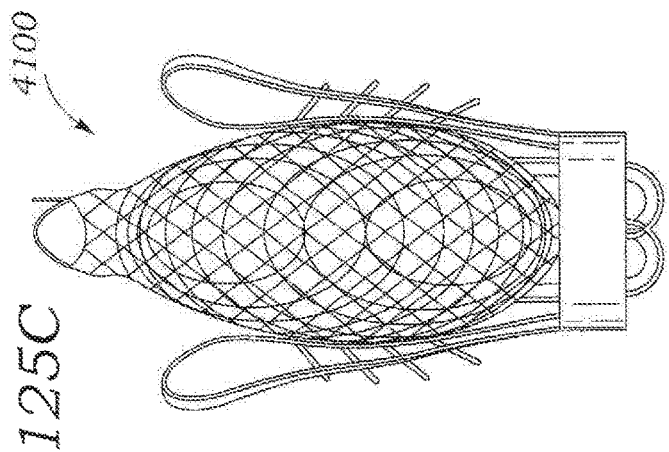
FIGS. 125A-125E show another exemplary embodiment of an implantable prosthetic device.
Figure 125C:
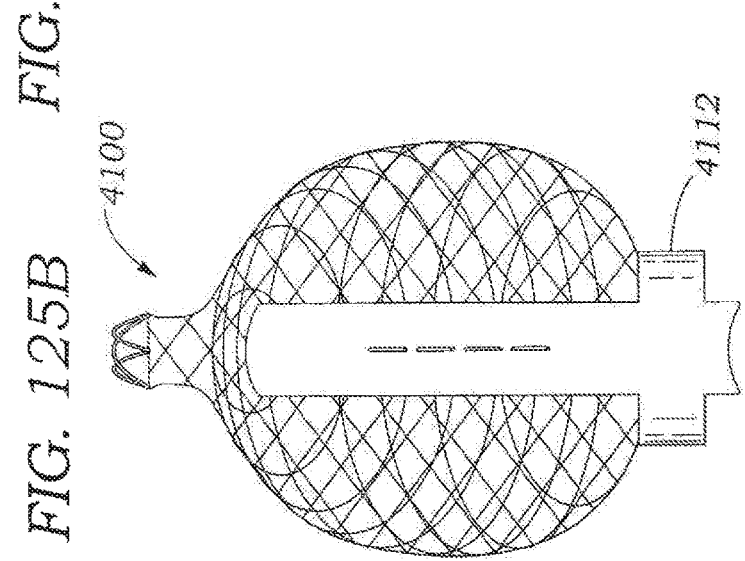
Figure 125A:
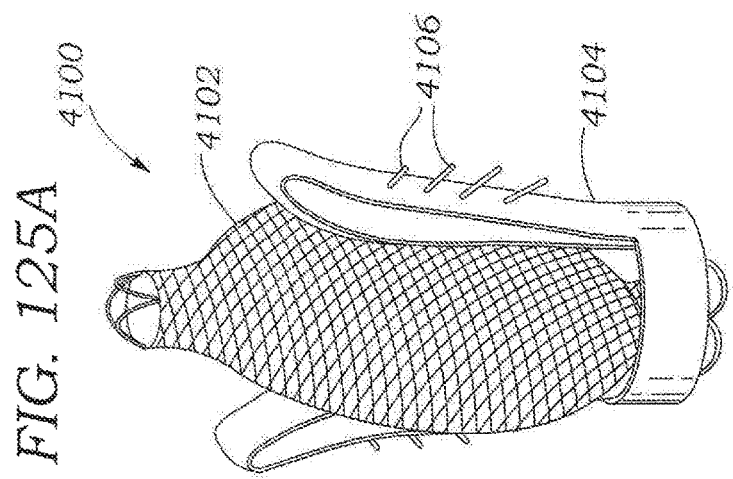
Figure 125D:
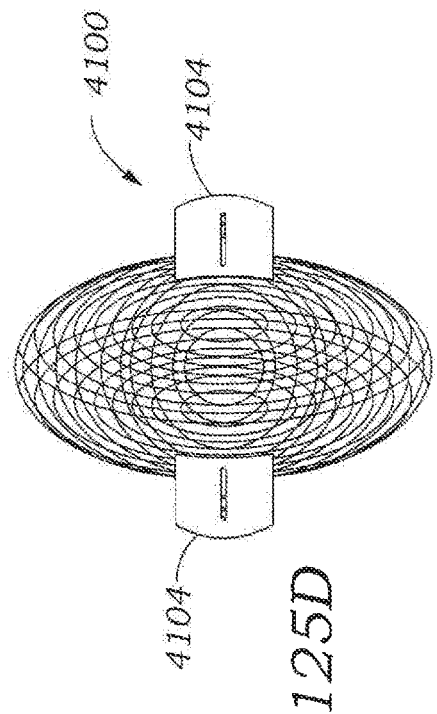
Figure 125E:
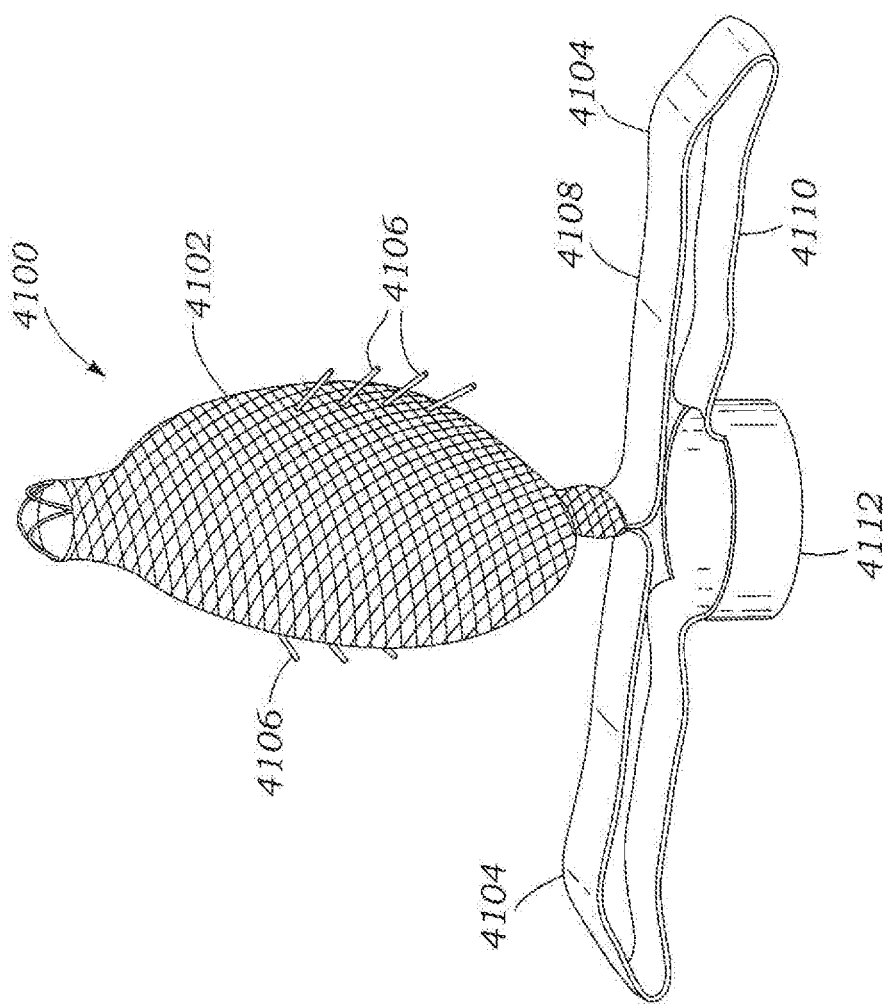

FIGS. 125A-125E show a prosthetic device 4100 comprising a generally spherical or bulbous main body 4102, anchors 4104 coupled to the main body, and projections 4106 extending outwardly from the main body. In particular embodiments, the main body 4102 and the anchors 4104 can comprise a braided or weaved structure, such as a metal braid or weave, as described in embodiments above. As best shown in FIG. 125E (which shows the anchors in a partially deployed position), each anchor 4104 comprises a first foldable portion 4108 having one end connected to the ventricular end of the main body and a second foldable portion 4110 having one end connected to a lower ring 4112. When the device 4100 is fully deployed, the foldable portions 4108, 4110 are folded upwardly alongside the main body 4102 such that the native leaflets are captured between the main body and the foldable portions 4108 with the projections 4106 engaging the native leaflets. As shown in FIGS. 125A-125D, the ring 4112 is moved upwardly around the lower end portions of foldable portions 4108, 4110 to resist movement of the anchors away from the closed position, thereby retaining the device in place against the native leaflets. Although not shown, the anchors can be completely unfolded to a delivery configuration by moving the ring 4212 further axially away from the main body 4202 relative to the partially folded stub shown in FIG. 126A.

Figure 126G:
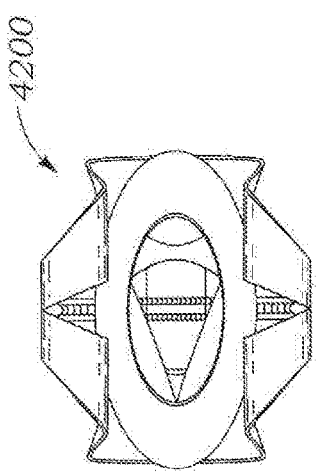
Figure 126J:
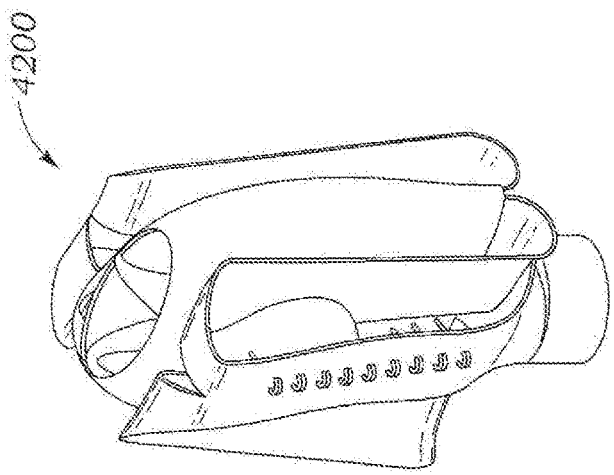
Figure 126H:
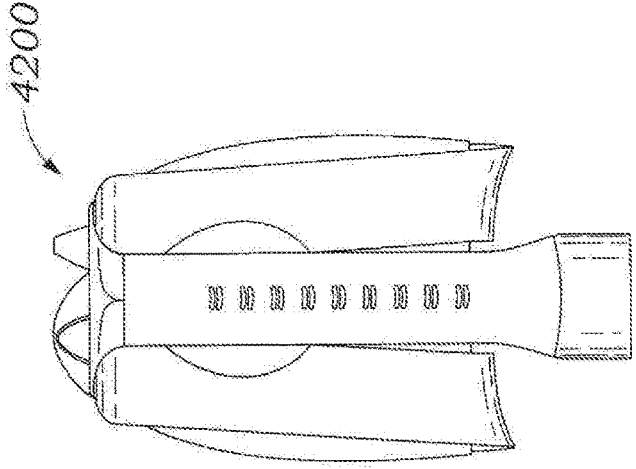
Figure 126I:
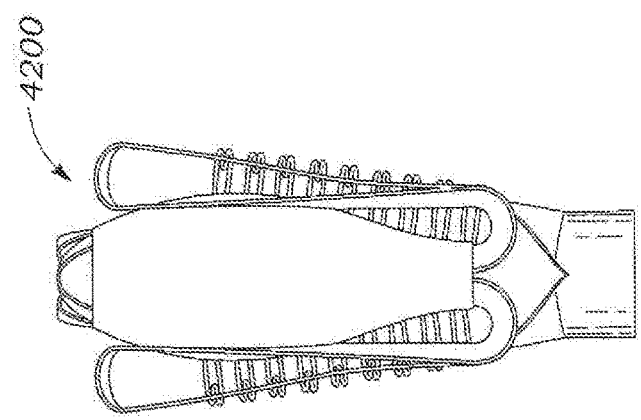

FIGS. 126A-126J show a prosthetic device 4200. The device 4200 is similar to the device 4100 in that it includes a generally spherical or bulbous main body 4202 and anchors 4204 coupled to the main body. The main body 4202 and the anchors 4204 can comprise a braided or weaved structure, such as a metal braid or weave, as described in embodiments above. Each anchor 4204 can comprise a first foldable portion 4208 having one end connected to the ventricular end of the main body and a second foldable portion 4210 having one end connected to a lower ring 4212. Unlike the device 4100, the projections 4206 are mounted to the inner surfaces of the second foldable portions 4210 and the first foldable portions 4208 can be formed with slots or openings 4214 that allow the projections 4206 to extend through the openings and engage the native leaflets when the anchors 4204 are moved to the closed, fully deployed position. FIG. 126A shows the anchors 4204 in a partially deployed state in which the anchors are partially folded. FIG. 126B shows a detail view of a portion of the main body 4202, as indicated in FIG. 126A. FIGS. 126C-126F show the anchors in a further partially deployed state in which the anchors are further folded from the position shown in FIG. 126A. FIGS. 126G-126J show the anchors in a fully deployed, folded and closed state alongside the main body 4202 with the projections 4206 extending through the openings in the first foldable portions 4208 to engage the native leaflets.

Figure 127E:
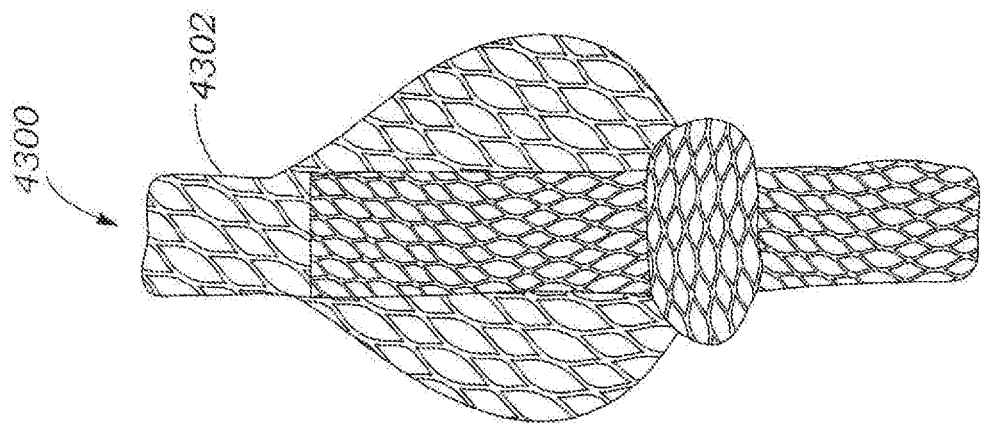
Figure 127F:
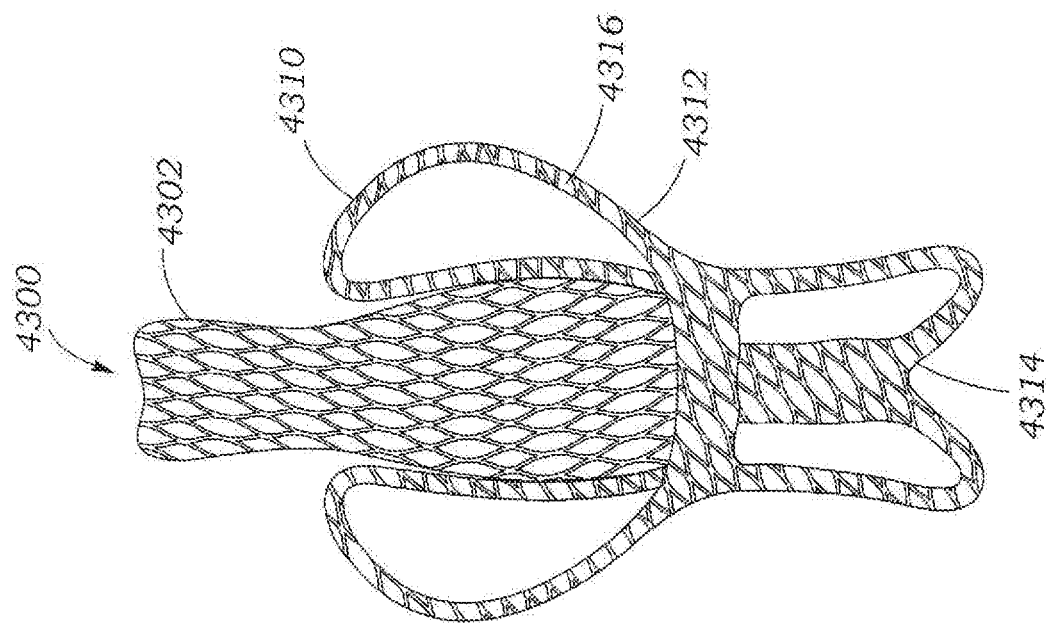

FIGS. 127A-127F show a prosthetic device 4300. The device 4300 is similar to the device 4100 in that it includes a generally spherical or bulbous main body 4302 and anchors 4304 coupled to the main body. The main body 4302 and the anchors 4304 can comprise a braided or weaved structure, such as a metal braid or weave, as described in embodiments above and as best shown in FIGS. 127E and 127F. The device 4300 comprises a lower ring or sleeve 4312. Each anchor 4304 can comprise a first, inner foldable portion 4308 that is connected at one end to the lower end 4314 of the main body 4302 and a second, outer foldable portion 4310 that is connected at one end to the upper end 4316 of the lower ring 4212. The first foldable portion 4308 extends upwardly from the lower end 4314 of the main body 4302, through an opening in the second foldable portion 4310, and then curves outwardly and downwardly where it is connected to the upper end of the second foldable portion 4310.

During delivery the lower sleeve 4312 is spaced from the main body such that the lower sleeve does not overlap the anchors and the foldable portions of the anchors are folded away from the main body (similar to FIG. 126A). As the device is deployed, the native leaflets are placed on opposite sides of the main body, and the anchors are folded upwardly toward the main body to the fully deployed position (FIG. 127A) in which to the native leaflets are engaged between the main body 4302 and the first foldable portions 4308. Folding of the anchors causes the sleeve 4312 to be pulled over the lower end portions of the first foldable portions 4308 to retain the anchors in the fully deployed position.

By incorporating the supplemental anchoring members as shown in FIGS. 114-127F, the structural components of the prosthetic device (e.g., the metal frame of the main body and/or the anchors) can be made relatively thinner and/or more flexible. As a result, the device is more easily crimped for loading into a delivery sheath and exhibits greater flexibility for tracking through small radius turns as it is advanced toward the implantation site.

Figure 128:
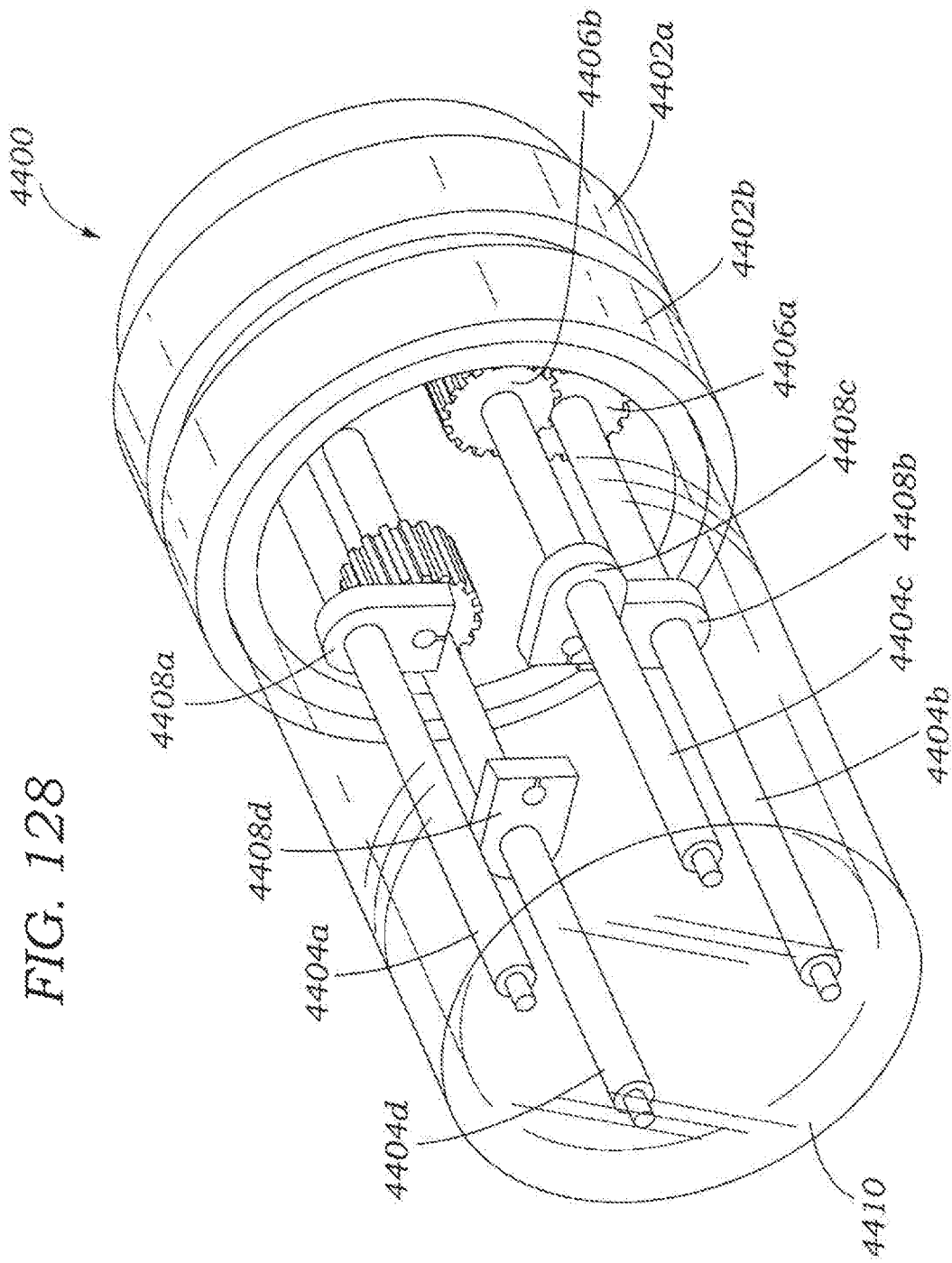
FIG. 128 shows an alternative embodiment of a steering control mechanism for a delivery device.

FIG. 128 shows an alternative embodiment of a steering control mechanism 4400 that can be incorporated in any of the delivery devices described above (e.g., delivery device 1300) to control the deflection of the distal end portion of the delivery device. The control mechanism 4400 comprises in the illustrated embodiment a proximal control knob 4402a, a distal control knob 4402b, first and second shafts 4404a, 4404b, respectively, operatively coupled to the proximal control knob 4402a, and third and fourth shafts 4404c, 4404d, respectively, operatively coupled to the distal control knob 4402b. A housing 4410 (illustrated as transparent in FIG. 128) can house the shafts, and the control knobs can be movably coupled to the housing 4410.

The first and second shafts 4404a, 4404b are coupled to the proximal control knob 4402a by respective gears 4406a mounted on the proximal ends of the shafts. The third and fourth shafts 4404c, 4404d are coupled to the distal control knob 4402b by respective gears 4406b mounted on the proximal ends of the shafts. In this manner, rotation of the proximal control knob 4402a causes corresponding rotational movement of the first and second shafts 4404a, 4404b, and rotation of the distal control knob 4402b causes corresponding rotational movement of the third and fourth shafts 4404c, 4404d.

Mounted on the shafts are respective pull wire retainers 4408a, 4408b, 4408c, and 4408d. The proximal ends of four pull wires (not shown) are fixedly secured to the pull wire retainers. Each of the pull wire retainers 4408a, 4408b, 4408c, 4408d have internal threads that engage externals threads of their respective shafts 4404a, 4404b, 4404c, 4404d and are fixed against rotational movement such that rotation of the shafts cause the pull wire retainers to move axially along the shafts upon rotational movement of the control knobs 4402a, 4402b. The first and second shafts 4404a, 4404b are threaded in opposite directions, while the third and fourth shafts 4404c, 4404d are threaded in opposite directions. In this manner, rotation of the proximal control knob 4402a causes the pull wire retainers 4408a, 4408b to move axially in opposite directions and rotation of the distal control knob 4402b causes the pull wire retainers 4408c, 4408d to move axially in opposite directions.

For example, if proximal control knob 4402a is rotated to move the first pull wire retainer 4408a proximally and the second pull wire retainer 4408b distally, the pull wire attached to the first pull wire retainer 4408a is tensioned and the pull wire attached to the second pull wire retainer is slackened, causing the delivery device to bend or deflect under the tension of the pull wire attached to the first pull wire retainer (upwardly in the illustrated embodiment). Conversely, rotating the proximal control in the opposite direction will causes the delivery device to deflect under the tension of the pull wire attached to the second pull wire retainer 4408b (downwardly in the illustrated embodiment). Similarly, rotating the distal control knob 4402b causes the delivery device to deflect sideways to the left or the right under the tension of the pull wire attached to the pull wire retainer 4408c or 4408d, depending upon the direction of rotation of the distal control knob. Rotation of both the proximal and distal control knobs 4402a, 4402b causes the delivery device to deflect under the tension of two of the pull wires. Thus, as can be appreciated, the delivery device can be deflected upwardly, downwardly, sideways (to the left or the right), or in any direction in between (e.g., downwardly to the left or the right or upwardly to the left or the right).

Figure 129:
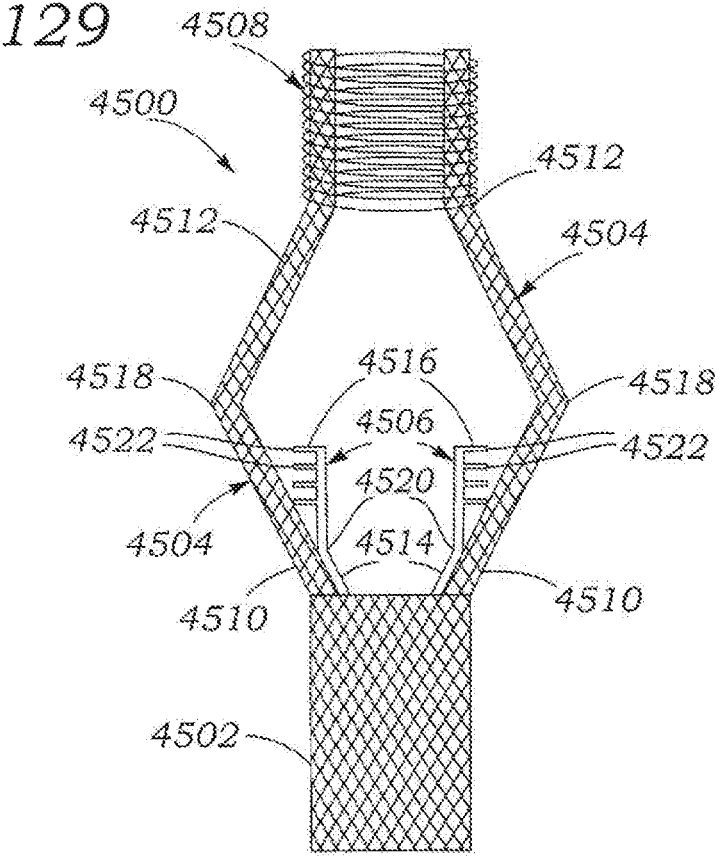
FIGS. 129-130 show another exemplary embodiment of an implantable prosthetic device.
Figure 130:
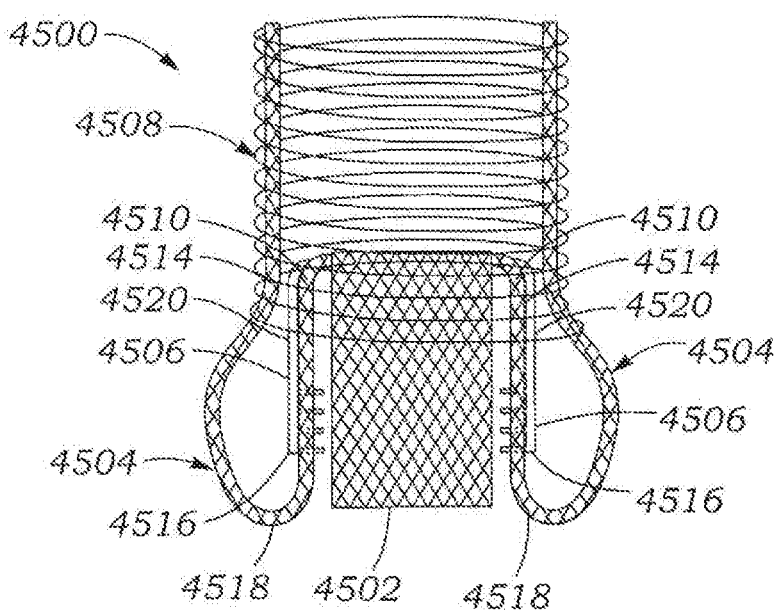

FIGS. 129-130 show an exemplary embodiment of an implantable prosthetic device 4500, similar to the prosthetic device 600. The prosthetic device 4500 can comprise a spacer body 4502, a plurality of anchors 4504 (e.g., two in the illustrated embodiment), a plurality of securing members 4506 (e.g., two in the illustrated embodiment) and a locking element 4508. As best shown in FIG. 129 (which shows the prosthetic device 4500 in a radially compressed configuration), proximal end portions 4510 of the anchors 4504 can be coupled to the spacer body 4502, and distal end portions 4512 of the anchors 4504 can be coupled to the locking element 4508. Proximal end portions 4514 of the securing members 4506 can be coupled to the proximal end portions 4510 of the anchors 4504, and the securing members 4506 can extend distally from the proximal end portions 4514 to free, distal end portions 4516 of the securing members 4506.

In other embodiments, the prosthetic device 4500 can comprise greater or fewer anchors 4504 and/or securing members 4506. For example, in some embodiments, the prosthetic device 4500 can comprise three anchors 4504 and three securing members 4506. In some embodiments, the number of securing members 4506 can be less than or greater than the number of anchors 4504.

As shown, the spacer body 4502, the anchors 4504, and/or the locking element 4508 can, for example, be formed from a braided material. In such embodiments, the spacer body 4502, the anchors 4504, and/or the locking element 4508 can be covered with a blood-impervious material and/or coating.

In some embodiments, two or more of the spacer body 4502, the anchors 4504, and/or the locking element 4508 can be formed from a single unitary piece of material. In other embodiments, the spacer body 4502, the anchors 4504, and/or the locking element 4508 can be formed from separate piece of material that are coupled together (e.g., by welding, an adhesive, fasteners, etc.).

The spacer body 4502 of the prosthetic device 4500 can be configured to reduce and/or prevent regurgitation between native heart valve leaflets (e.g., native mitral valve leaflets) in a manner similar the spacer body 612 of the prosthetic device 600.

As noted above, the anchors 4504 can comprise the proximal and distal end portions 4510, 4512. The anchors 4504 of the prosthetic device 4500 can also each include a joint portion 4518 disposed between a respective proximal and distal end portion 4510, 4512. As such, the anchors 4504 can be configured to move from a first configuration (e.g., a resting or undeflected configuration, as shown in FIG. 129) to a second configuration (e.g., a deflected configuration, as shown in FIG. 130), and vice versa, by pivoting at the joint portions 4118 with a delivery apparatus (not shown) (e.g., similar to the manner in which the anchors 610 of the prosthetic device 600 can bend at the joints 618 using the delivery apparatus, as shown in FIGS. 27-34).

As also noted above, the securing members 4506 can include the proximal and distal end portions 4514, 4516. The securing members 4506 can also each include a hinge portion 4520 and a plurality of projections 4522. The hinge portions 4520 can be disposed between the proximal and distal end portions 4514, 4516. The projections 4522 can be coupled to and extend radially (i.e., radially outwardly as depicted in FIG. 129 and radially inwardly as depicted in FIG. 130) from the distal end portions 4516.

The securing members 4506 can be configured to pivot at the hinge portions 4520 such that the delivery apparatus can be used to move the securing members 4506 from a first configuration (e.g., a resting or undeflected configuration, as shown in FIG. 129) to a second configuration (e.g., a compressed configuration, as shown in FIG. 130), and vice versa, as further described below.

In the first configuration, the securing members 4506 can be angled at the hinge portions 4520 such that the projections 4522 of the securing members 4506 do not extend into and/or through the respective proximal end portions 4510 of the anchors 4504. In other words, the projections 4522 are disposed radially inwardly (i.e., as depicted in FIG. 129) relative to the proximal end portions 4510 of the anchors 4504. This configuration can reduce and/or prevent the projections 4522 of the securing members 4506 from engaging (e.g., snagging) a delivery cylinder of a delivery apparatus (not shown) and/or a patient's native tissue (not shown) as the prosthetic device 4500 is loaded, positioned, and/or recaptured (e.g., during an implantation procedure).

This can be accomplished, for example, by forming the securing members 4506 from a relatively elastic material (e.g., Nitinol) and shape-setting the securing members 4506 such that an angle between the proximal and distal end portions 4514, 4516 at the hinge portions 4520 is less than about 180 degrees. In some embodiments, the angle can be about 135 degrees to about 175 degrees, and in one particular embodiment, the angle can be about 155 degrees.

As noted above, the securing members 4506 can be moved from the first configuration to the second configuration using the delivery apparatus. The delivery apparatus can axially move the locking element 4508 and the spacer body 4502 toward each other such that the anchors 4504 pivot at the joints 4518 and the locking element 4508 slides over and radially overlaps the securing members 4506 at and/or distal to the hinge portions 4520 of the securing members 4506, as shown in FIG. 130. The locking element 4508 and the securing members 4506 can be configured such that the locking element 4508 presses against the securing members 4506, thus causing the securing members 4506 to pivot radially inwardly at the hinge portions 4520 to the second configuration, as shown in FIG. 130. The locking element 4508 can be configured to slightly radially expand as it is slid over the securing members 4506 when moved to the second configuration.

In the second configuration, the securing members 4506 can be angled at the hinge portions 4520 such that the projections 4522 at distal end portions 4516 of the securing members 4506 extend into and through the respective proximal end portions 4510 of the anchors 4504, as shown in FIG. 130. In other words, the projections 4522 can extend radially inwardly (i.e., as depicted in FIG. 130) beyond the proximal end portions 4510 of the anchors 4504. This configuration allows the projections 4522 to engage native tissue to secure the prosthetic device 4500 at an implantation location. For example, the projections 4522 can engage and/or penetrate native leaflets that are disposed radially between the spacer body 4502 and the anchors 4504 (e.g., similar to the positioning of prosthetic device 300 shown in FIG. 17).

Once the prosthetic device 4500 is desirably positioned, the locking element 4508 can be secured relative to the spacer body 4502, the anchors 4504, and the securing members 4506. This secures the prosthetic device 4500 relative to the native tissue. The prosthetic device 4500 can then be released from the delivery apparatus by actuating the delivery apparatus.

Prior to releasing the prosthetic device 4500, the prosthetic device 4500 can be repositioned and/or retrieved with the delivery apparatus by moving the locking element 4508 relative to the securing members 4506 such that the locking element 4508 is axially separated from the securing members 4506. This allows the securing members 4506 to disengage the native tissue and to move from the second configuration back to the first position. The prosthetic device can then be moved relative to the native tissue and/or retrieved into the delivery cylinder of the delivery apparatus with a reduced likelihood that the projections 4522 will engage native tissue and/or the delivery cylinder.

Prosthetic Valves

Figure 131:
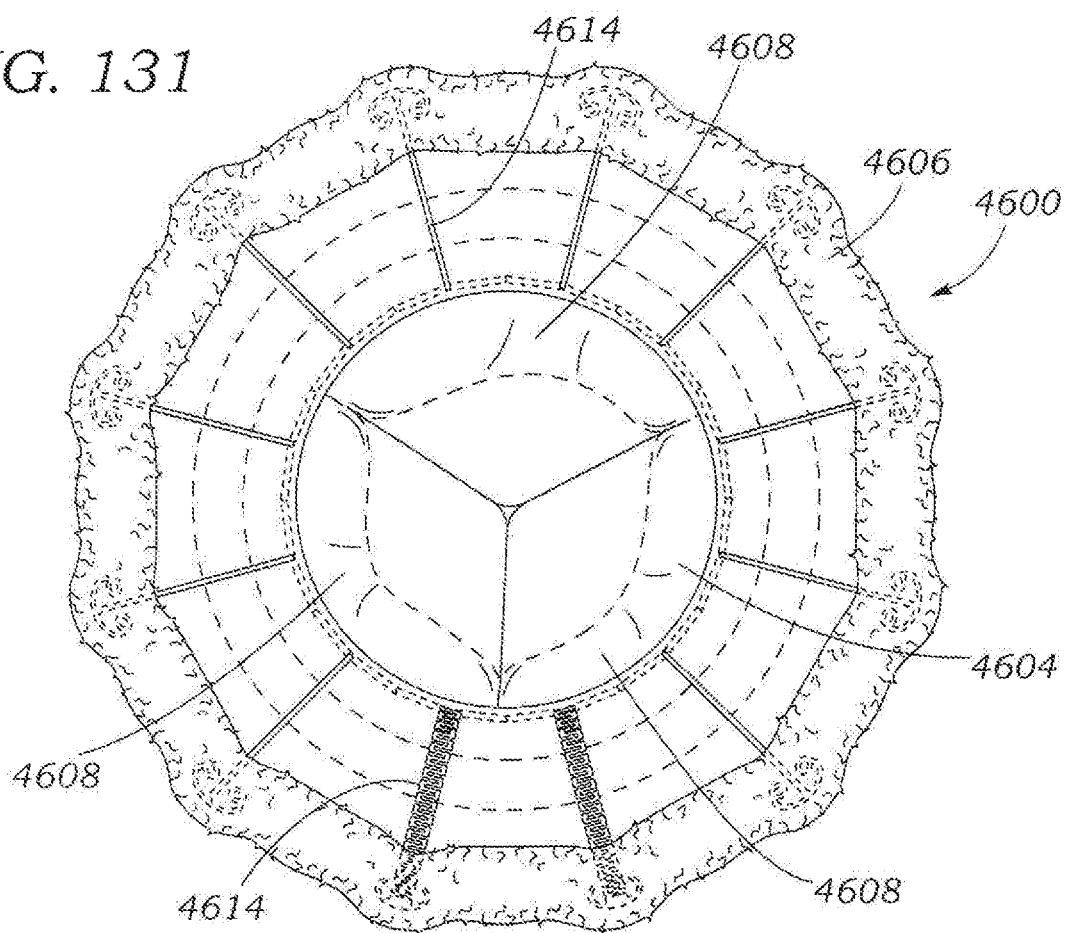
FIGS. 131-133 show an exemplary embodiment of an implantable prosthetic heart valve.
Figure 132:
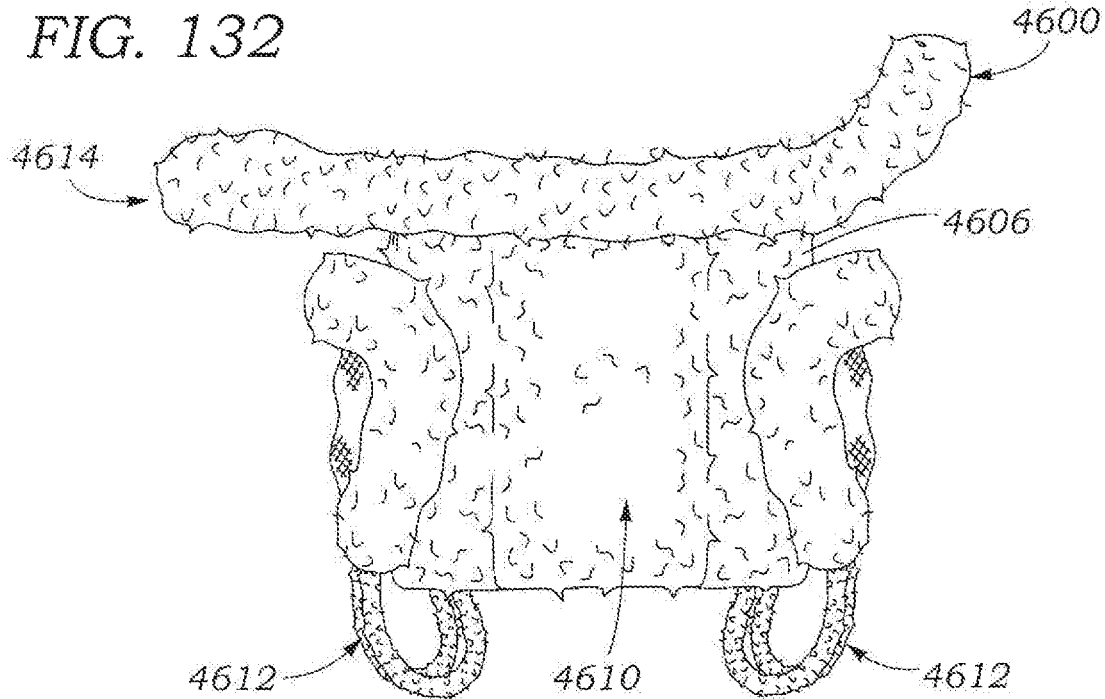
Figure 133:
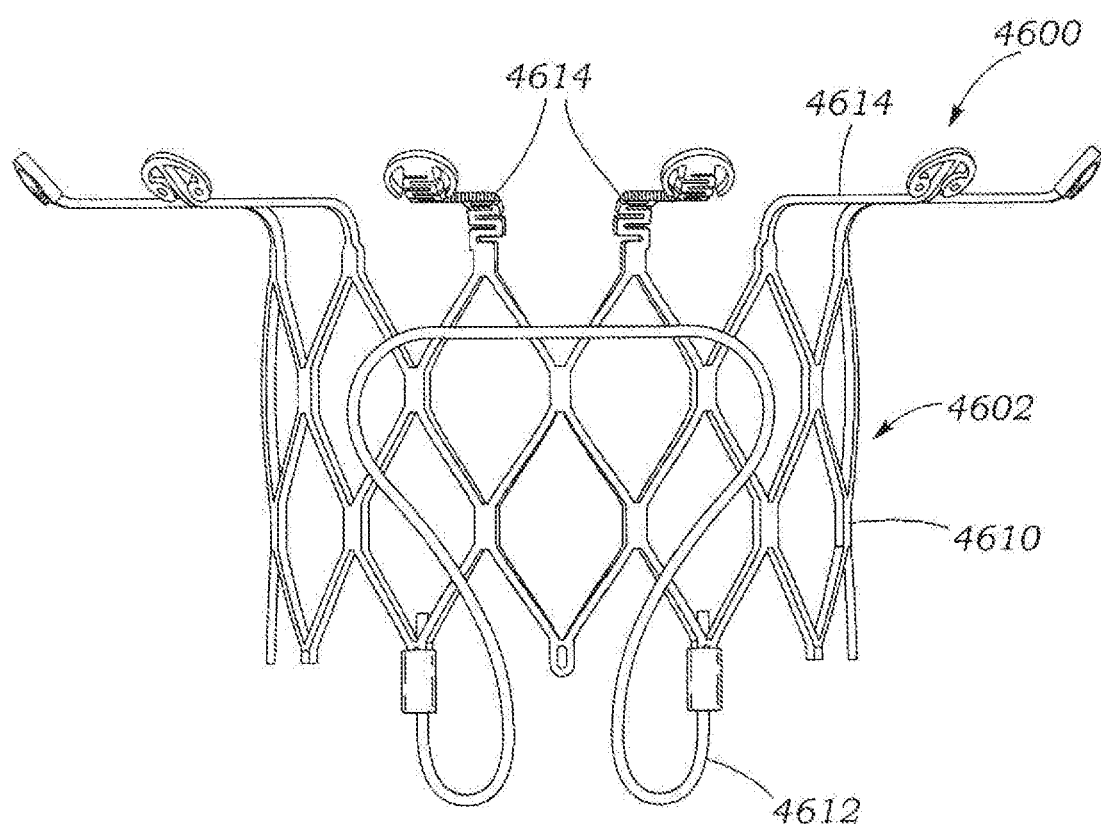

FIGS. 131-133 show an exemplary embodiment of a prosthetic heart valve 4600. The prosthetic valve 100 can comprise a stent or frame 4602 (FIG. 133), a leaflet assembly 4604 supported by and secured inside the frame 4602 and a cover 4606 covering portions of the frame 4602. The leaflet assembly 4604 can comprise one or more tissue leaflets 4608 (three in the illustrated embodiment) made of biological material (e.g., pericardial tissue, such as bovine, porcine or equine pericardial tissue) or synthetic material (e.g., polyurethane). The leaflets 4608 are configured to allow blood to flow through the prosthetic valve 4600 in one direction and block the flow of blood in the opposite direction. In FIG. 131, the leaflets 4608 are shown in solid lines, depicting the closed position for blocking the flow of blood, and in dashed lines, depicting the open position allowing blood to flow through the prosthetic valve 4600.

FIG. 133 shows the frame 4602 without the leaflet assembly 4604 or cover 4604. The frame 4602 can comprise an annular main body 4610 (which houses the leaflet assembly 4604), one or more first anchors 4612 extending from one end of the main body 4610, and one or more second anchors 4614 extending from the opposite end of the main body 4610. In the illustrated example, the prosthetic valve 4600 comprises a prosthetic mitral valve that is implantable in the native mitral valve annulus, the first anchors 4612 comprise ventricular anchors that are deployed behind the native mitral valve leaflets within the left ventricle, and the second anchors 4614 comprise atrial anchors that are deployed against the native mitral valve annulus within the left ventricle. The illustrated prosthetic mitral valve 4600 comprises two ventricular anchors 4612 positioned on diametrically opposite sides of outflow end of the main body 4610 and twelve atrial anchors 4614. In other embodiments, the prosthetic valve 4600 can include greater or fewer number of ventricular anchors 4612 and/or atrial anchors 4614.

The frame 4602 can comprise a shape-memory material, such as nitinol (a nickel-titanium alloy) for example, to enable self-expansion from a radially compressed state to an expanded state. Although not shown, when constructed of a self-expanding material, the prosthetic valve 4600 can be crimped to the radially compressed state using the crimping apparatus and loaded into a sheath of a delivery catheter for delivery to an implantation site. When released from the sheath, the prosthetic valve 4600 can self-expand to the expanded state at the implantation site (e.g., the native mitral valve). In alternative embodiments, the frame 4602 can be plastically expandable from a radially compressed state to an expanded state by an expansion device, such as an inflatable balloon (not shown), for example. Such plastically expandable frames can comprise stainless steel, chromium alloys, and/or other suitable materials. When constructed of a plastically expandable material, the prosthetic valve 4600 can be crimped using the crimping apparatus to a radially compressed state onto or adjacent a balloon (or other expansion device) of a delivery catheter. Additional details regarding crimping the prosthetic heart valve 4600 and crimping devices can be found, for example, in U.S. Patent Application Publication No. 2015/0336150 A1, which is incorporated herein by reference in its entirety.

The cover 4606 can comprise a blood-impermeable fabric and can extend over the outside of the main body 4610, the atrial anchors 4614, and/or portions of the ventricular anchors 4612. The fabric can comprise a polyester material, such as polyethylene terephthalate (PET). Alternatively, the cover can comprise biological matter, such as pericardial tissue or other biological tissue. Further details of the prosthetic valve 4600, for example, construction and assembly, are disclosed in U.S. Pat. No. 8,449,599 and U.S. Patent Application Publication No. 2014/0222136.

In the expanded state, the ventricular anchors 4612 extend along the outer surface of the main body 4610. Thus, once implanted at the native mitral valve, the native mitral valve leaflets can be captured between the main body 4610 and ventricular anchors 4612, thereby anchoring the prosthetic valve 4600 in place against systolic pressure in the left ventricle. The atrial anchors 4614 extend axially and radially outwardly from the inflow end of the main body 4610. Thus, once implanted at the native mitral valve, the atrial anchors 4614 can be disposed in the left atrium against the native mitral valve annulus, thereby anchoring the prosthetic valve 4600 in place against diastolic pressure in the left ventricle.

Figure 134:
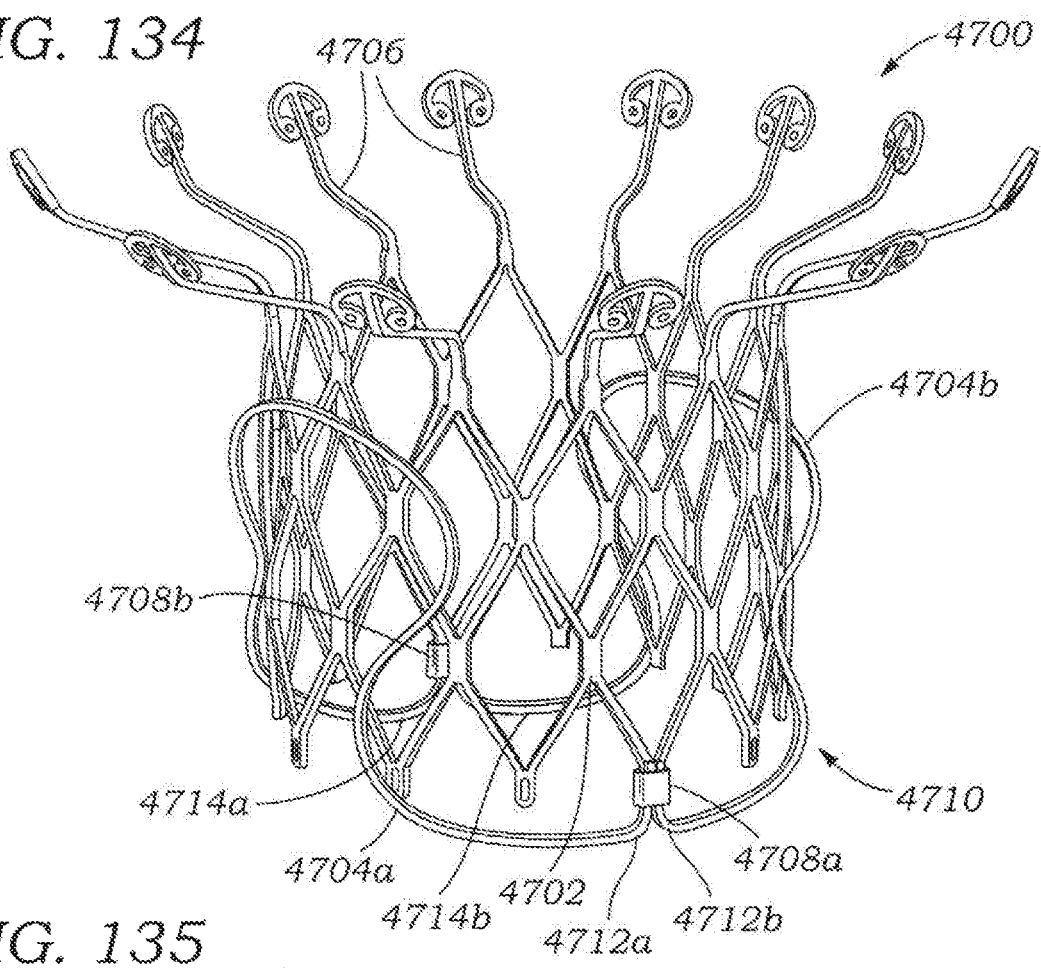
FIGS. 134-135 show an exemplary embodiment of a frame for an implantable prosthetic heart valve.
Figure 135:
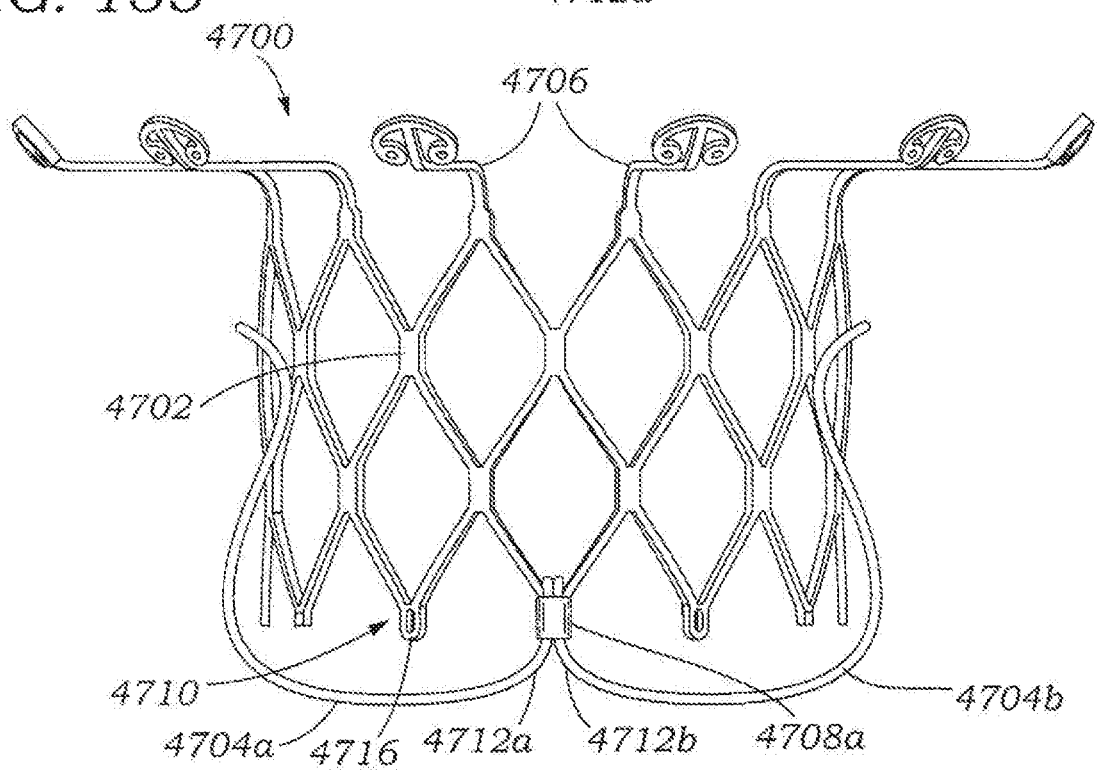

FIGS. 134-135 show a frame 4700 for a prosthetic heart valve. The frame 4700 can be configured similar to the frame 4602 of the prosthetic heart valve 4600 (e.g., for implantation in a native mitral valve annulus) and can, for example, be used with the leaflet assembly 4604 and the cover 4606 of the prosthetic heart valve 4600. The frame 4700 can comprise an annular main body 4702, one or more first anchors 4704 (e.g., two in the illustrated embodiment 4704*a*, 4704*b*, collectively referred to herein as "the first anchors 4704") extending from one end of the main body 4702, and one or more second anchors 4706 (e.g., twelve in the illustrated embodiment) extending from the opposite end of the main body 4702.

In some embodiments, the first anchors 4704 can be coupled to the main body 4702 with a plurality of tabs or sleeves 4708 (e.g., two in the illustrated embodiment 4708*a*, 4708*b*, collectively referred to herein as "the tabs 4708"). The tabs 4708 can be coupled to and/or extend from a first end 4710 (e.g., an outflow end) of the main body 4702 (e.g., on apices or junctions 4716 where two struts of the frame 4700 come together at the frame outflow) and positioned on diametrically opposite sides of the main body 4702 relative to each other. The tabs 4708 can be configured to securely receive end portions of the first anchors 4704. As best shown in FIG. 134, the tab 4708*a* can securely receive first end portions 4712*a*, 4712*b* of the respective first anchors 4704*a*, 4704*b*, and the tab 4708*b* can securely receive second end portions 4714*a*, 4714*b* of the respective first anchors 4704*a*, 4704*b*. The tabs 4708 can be crimped and/or welded to the end portions of the first anchors 4704 and the apices 4716 to enhance the connection between the first anchors 4704 and the main body 4702 of the frame 4700.

Configuring the frame 4700 such that the first anchors 4704 share the tabs 4708 at the first and second end portions 4712, 4714 of the first anchors 4704 advantageously balances the first anchors 4704 relative to the main body 4702. As such, forces that are exerted on the first anchors 4704 during the dynamic heart cycles tend to be equal and opposite of each other, thus canceling each other. This can reduce and/or eliminate the forces that are transferred from the anchors 4704 to the main body 4702 and, thus, reduce and/or prevent the main body 4702 from deflecting radially inwardly at the first end 4710 during the dynamic heart cycles.

The first anchors 4704 can be configured to pivot 180 degrees relative to the main body 4702 from a functional configuration (e.g., FIGS. 134-135) to a compressed, delivery configuration (not shown), and vice versa. In the delivery configuration, the first anchors 4704 can extend axially away from the second anchors 4706, as opposed to toward the second 4706 as shown in FIGS. 134-135. As such, the first anchors 4704 do not increase the radial profile of the frame 4700 because the first anchors 4704 do not radially overlap with the main body 4702. This can be accomplished, for example, by forming the first anchors 4704 from a relatively flexible material such as Nitinol, stainless steel, and/or chromium alloys. A prosthetic valve comprising the frame 4700 can be delivered using a delivery apparatus, such as disclosed in U.S. Patent Application Publication No. 2014/0222136, which can be configured to control pivoting movement of the first anchors 4704 between the delivery configuration and the functional configuration with the native leaflets captured between the anchors of the main body.

The geometry of the first anchors 4704 can comprise various configurations. For example, the shape, the dimensions, etc. can be configured for a particular implantation location (e.g., the native mitral, aortic, pulmonary, and/or tricuspid valve) and/or for a desired crimped and/or functional radial profile.

In other embodiments, the frame 4700 can include greater or fewer number of first anchors 4704 and/or second anchors 4706. For example, the frame 4700 can include three first anchors 4704.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An implantable prosthetic device for connection to native heart valve leaflets, comprising:
    a spacer body that is configured such that the spacer body can (i) be disposed between native valve leaflets of a heart, (ii) block blood flow through the spacer body from an atrial side of the spacer body to a ventricular side of the spacer body, (iii) block blood flow through the spacer body from the ventricular side of the spacer body to the atrial side of the spacer body, and (iv) divide an orifice between a ventricle and an atrium such that the native heart valve leaflets can (a) open at two sides of the spacer body into two orifices during diastole to allow blood flow from the atrium to the ventricle through the two orifices, and (b) coapt to inhibit blood flow from the ventricle to the atrium during systole;
    wherein the spacer body has a proximal end and a distal end;
    wherein the spacer body extends radially outwardly as the spacer body extends away from the distal end toward the proximal end;
    at least one anchor portion coupled to the distal end of the spacer body, wherein the at least one anchor portion is placed against a ventricular surface of a corresponding one of the native heart valve leaflets; and
    a shaft that extends through the spacer body and that is coupled to the at least one anchor portion, wherein the shaft is configured to change the size of the spacer body.

2. The implantable prosthetic device of claim 1 further comprising a cap coupled to the at least one anchor portion.

3. The implantable prosthetic device of claim 1 wherein each of the at least one anchor portion includes an upper leg portion coupled to the distal end of the spacer body and a lower leg portion connected to the upper leg portion by a joint.

4. The implantable prosthetic device of claim 2 wherein each of the at least one anchor portion includes an upper leg portion coupled to the distal end of the spacer body and a lower leg portion connected to the upper leg portion by a joint, wherein a distal end of the lower leg portion is fixedly secured to the cap.

5. The implantable prosthetic device of claim 1 wherein the spacer body and the at least one anchor portion are made from a single piece of braided self-expandable metallic thread.

6. The implantable prosthetic device of claim 3 wherein the spacer body and the at least one anchor portion are made from a single piece of braided self-expandable metallic thread.

7. The implantable prosthetic device of claim 1 wherein the spacer body is covered with a blood impervious material.

8. The implantable prosthetic device of claim 3 wherein the spacer body and the at least one anchor portion are covered with a blood impervious material.

9. The implantable prosthetic device of claim 1 wherein the spacer body is made from braided self-expandable metallic thread.

10. The implantable prosthetic device of claim 1 wherein the spacer body is configured such that compressing ends of the spacer body axially foreshortens the spacer body axially and expands the spacer body radially.

11. An assembly, comprising:
    an implantable prosthetic device having a spacer body, a plurality of anchors, and an end cap; and
    a delivery apparatus having a first shaft and a second shaft;
    wherein the spacer body extends radially outwardly as the spacer body extends from the distal end toward the proximal end and is configured to divide an orifice between a ventricle and an atrium into two orifices;
    wherein the plurality of anchors is coupled to the spacer body;
    wherein the plurality of anchors is coupled to the end cap;
    wherein the plurality of anchors is placed against ventricular surfaces of native heart valve leaflets;
    wherein the first shaft is coupled to the end cap;
    wherein the second shaft is coupled to a proximal end of the spacer body;

wherein movement of the first shaft relative to the second shaft moves the anchors relative to the spacer body.

12. The assembly of claim 11 wherein each of the plurality of anchors includes an upper leg portion coupled to the distal end of the spacer body and a lower leg portion connected to the upper leg portion by a joint.

13. The assembly of claim 11 wherein each of the plurality of anchors includes an upper leg portion coupled to the distal end of the spacer body and a lower leg portion connected to the upper leg portion by a joint, wherein a distal end of the lower leg portion is fixedly secured to the end cap.

14. The assembly of claim 11 wherein the spacer body and at least one of the plurality of anchors are made from a single piece of braided self-expandable metallic thread.

15. The assembly of claim 12 wherein the spacer body and at least one of the plurality of anchors are made from a single piece of braided self-expandable metallic thread.

16. The assembly of claim 11 wherein the spacer body is covered with a blood impervious material.

17. The assembly of claim 11 wherein the spacer body and at least one of the plurality of anchors are covered with a blood impervious material.

18. An assembly, comprising:
   an implantable prosthetic device having a spacer body, a plurality of anchors, and an end cap; and
   a delivery apparatus having a first shaft and a second shaft;
   wherein the spacer body extends radially outwardly as the spacer body extends from the distal end toward the proximal end and is configured to divide an orifice between a ventricle and an atrium into two orifices;
   wherein the plurality of anchors is coupled to the spacer body;
   wherein the plurality of anchors is coupled to the end cap;
   wherein the plurality of anchors is placed against ventricular surfaces of native heart valve leaflets;
   wherein the first shaft is coupled to the end cap;
   wherein the second shaft is coupled to a proximal end of the spacer body;
   wherein movement of the first shaft relative to the second shaft moves the anchors relative to the spacer body;
   wherein each of the plurality of anchors includes an upper leg portion coupled to the distal end of the spacer body and a lower leg portion connected to the upper leg portion by a joint; and
   wherein the spacer body is covered with a material that inhibits blood flow.

* * * * *